United States Patent
Oku et al.

(10) Patent No.: US 7,060,721 B1
(45) Date of Patent: Jun. 13, 2006

(54) IMIDAZOLE COMPOUNDS AND MEDICINAL USE THEREOF

(75) Inventors: Teruo Oku, deceased, late of Tokyo (JP); by Noriko Oku, legal representative, Tokyo (JP); by Chikako Oku, legal representative, Tokyo (JP); by Tomohito Oku, legal representative, Tokyo (JP); Hiroshi Kayakiri, Osaka (JP); Yoshito Abe, Ibaraki (JP); Hitoshi Hamashima, Kyoto (JP); Hitoshi Sawada, Ibaraki (JP); Naoki Ishibashi, Ibaraki (JP); Hiroyuki Setoi, Osaka (JP); Noritsugu Yamasaki, Hyogo (JP); Takafumi Imoto, Niigata (JP); Takahiro Hiramura, Ibaraki (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/869,135

(22) PCT Filed: Dec. 20, 1999

(86) PCT No.: PCT/JP99/07160

§ 371 (c)(1), (2), (4) Date: Oct. 29, 2002

(87) PCT Pub. No.: WO00/39091

PCT Pub. Date: Jul. 6, 2000

(30) Foreign Application Priority Data

Dec. 24, 1998 (JP) ............... 10-367362
Aug. 12, 1999 (JP) ............... 11-228838

(51) Int. Cl.
*A61K 31/4174* (2006.01)
*C07D 233/68* (2006.01)

(52) U.S. Cl. .............. 514/400; 514/341; 514/397; 546/275.1; 548/311.4; 548/338.5

(58) Field of Classification Search ............. 548/311.4, 548/338.5; 546/275.1; 514/341, 397, 400
See application file for complete search history.

(56) References Cited

U.S. PATENT DOCUMENTS 5,215,994 A  6/1993  Oku et al.
6,166,219 A  12/2000  Yamasaki et al.
6,242,474 B1 *  6/2001  Yamasaki et al. ........... 514/400
6,348,474 B1  2/2002  Kayakiri et al.

FOREIGN PATENT DOCUMENTS

EP  0 552 060  7/1993
EP  1 000 932  5/2000
WO  WO 99/359  1/1999

OTHER PUBLICATIONS

W. J. Coates, et al., J. Med. Chem., vol. 36, No. 10, pp. 1987-1392, "Cyclic Nucleotide Phosphodiesterase Inhibiton by Imidazopyridines: Analogues of Sulmazole and Isomazole as Inhibitors of the cGMP Specific Phosphodiesterase", 1993.
S. J. Lee, et al., J. Med. Chem., vol. 38, No. 18, pp. 3547-3557, "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities", 1995.

* cited by examiner

*Primary Examiner*—Laura L. Stockton
(74) *Attorney, Agent, or Firm*—Oblon, Spivak, McClelland, Maier & Neustadt, P.C.

(57) ABSTRACT

Imidazole compounds represented by general formula (I):

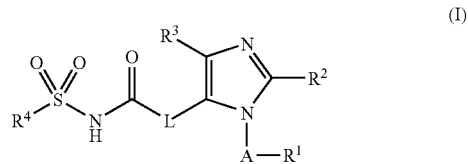

wherein each symbol is as defined in the specification, and salts thereof, and a pharmaceutical composition containing same are provided. These compounds are useful in treating the diseases curable based on a hypoglycemic action, and the diseases curable based on a cGMP-PDE inhibitory action, a smooth muscle relaxing action, a bronchodilating action, a vasodilating action, a smooth muscle cell inhibitory action and an allergy inhibitory action.

6 Claims, No Drawings

IMIDAZOLE COMPOUNDS AND MEDICINAL USE THEREOF

TECHNICAL FIELD

The present invention relates to novel imidazole compounds. More particularly, the present invention relates to novel imidazole compounds and salts thereof having hypoglycemic activity or PDE-V inhibitory activity. The present invention also relates to a method for producing the above-mentioned imidazole compounds and salts thereof. Moreover, the present invention relates to pharmaceutical compositions comprising the above-mentioned imidazole compound or a salt thereof as an active ingredient.

DISCLOSURE OF THE INVENTION

The present invention aims at providing novel imidazole compounds, pharmaceutically acceptable salts thereof and pharmaceutical preparations comprising the above-mentioned imidazole compound or a pharmaceutically acceptable salt thereof as an active ingredient, which are used as an agent for the prophylaxis and/or treatment of impaired glucose tolerance disorder, diabetes (e.g., type II diabetes), gestational diabetes, diabetic complications (e.g., diabetic gangrene, diabetic arthropathy, diabetic osteopenia, diabetic glomerulosclerosis, diabetic nephropathy, diabetic dermatopathy, diabetic neuropathy, diabetic cataract, diabetic retinopathy and the like), insulin resistance syndrome (e.g., insulin receptor abnormality, Rabson-Mendenhall syndrome, leprechaunism, Kobberling-Dunnigan syndrome, Seip syndrome, Lawrence syndrome, Cushing syndrome, acromegaly and the like), polycystic ovary syndrome, hyperlipidemia, atherosclerosis, cardiovascular diseases (e.g., stenocardia, cardiac failure and the like), hyperglycemia (e.g., those characterized by abnormal saccharometabolism such as eating disorders), pancreatitis, osteoporosis, hyperuricemia, hypertension, inflammatory bowel diseases, and skin disorders related to an anomaly of differentiation of epidermic cells; and, which, based on the cGMP-PDE (particularly PDE-V) inhibitory action, smooth muscle relaxing action, bronchodilating action, vasodilating action, smooth muscle cell inhibitory action, allergy suppressing action and the like, are used as an agent for the prophylaxis and/or treatment of angina pectoris, hypertension, pulmonary hypertension, congestive heart failure, glomerulopathy (e.g., diabetic glomerulosclerosis), tubulointerstitial disorders (e.g., kidney diseases induced by FK506, cyclosporin and the like), renal failure, atherosclerosis, angiostenosis (e.g., after percutaneous arterioplasty), peripheral vascular diseases, cerebral apoplexy, chronic reversible obstructive impairment (e.g., bronchitis, asthma inclusive of chronic asthma and allergic asthma), autoimmune diseases, allergic rhinitis, urticaria, glaucoma, diseases characterized by impaired intestinal motility (e.g., irritable bowel syndrome), impotence (e.g., organic impotence, psychic impotence and the like), nephritis, cancer cachexia, restenosis after PTCA, cachexia (e.g., progressive weight loss due to lipolysis, myolysis, anemia, edema, anorexia and the like in chronic diseases such as cancer, tuberculosis, endocrine diseases and AIDS), and the like.

The imidazole compound [hereinafter to be also referred to as the objective compound (I)], which is the novel compound of the present invention, has the formula (I):

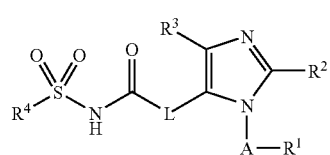

wherein $R^1$ is an aryl or heterocyclic group substituted by substituent(s) selected from the group consisting of (1) aryl, (2) heterocyclic group, (3) halogen, (4) halo(lower)alkyl, (5) lower alkylthio, (6) nitro, (7) lower alkenyl optionally substituted by aryl, (8) lower alkynyl optionally substituted by aryl, (9) lower alkoxy optionally substituted by cyclo(lower)alkyl or aryl, (10) aryloxy and (11) amino optionally substituted by protected carboxy or lower alkyl;

$R^2$ is a lower alkyl;

$R^3$ is a hydrogen, halogen, lower alkyl or nitro;

$R^4$ is (1) a lower alkenyl optionally substituted by aryl or heterocyclic group, (2) aryl optionally substituted by lower alkenyl, (3) lower alkyl, or (4) heterocyclic group optionally substituted by halogen;

A is a lower alkylene; and

L is a single bond, lower alkenylene or lower alkylene optionally substituted by aryl or heterocyclic group, or —X—CH$_2$— wherein X is —O—, NR$^5$ wherein R$^5$ is hydrogen or lower alkyl, or —S—.

Preferred salts of the objective compound (I) are conventional salts that are non-toxic and acceptable for use as pharmaceuticals. Examples thereof include salts with alkali metal such as sodium and potassium, salts with alkaline earth metal such as calcium and magnesium, salts with inorganic base such as ammonium salt, salts with organic amine such as triethylamine, pyridine, picoline, ethanolamine and triethanolamine, salts with inorganic acid such as hydrochloric acid, hydrobromic acid, sulfuric acid and phosphoric acid, salts with organic carboxylic acid such as formic acid, acetic acid, trifluoroacetic acid, maleic acid and tartaric acid, addition salts with sulfonic acid such as methanesulfonic acid, benzenesulfonic acid and p-toluenesulfonic acid, and salts or addition salts with base such as basic or acidic amino acid such as arginine, aspartic acid and glutamic acid.

The objective compound (I) and a salt thereof of the present invention can be produced by the method shown by the following reaction formulas.

Production Method 1:

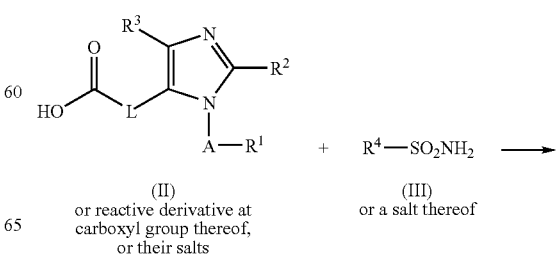

(II)
or reactive derivative at
carboxyl group thereof,
or their salts (III)
or a salt thereof -continued

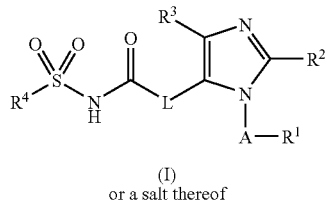

(I)
or a salt thereof wherein each symbol in the formulas is as defined above.

Various definitions in the above- and below-mentioned herein are explained in detail in the following.

"Lower" means 1 to 6 carbon atoms, unless otherwise specified.

"Alkyl" and "alkyl moiety" are each preferably linear or branched alkyl. Preferable specific examples include methyl, ethyl, 1-propyl, i-propyl, 1-butyl, i-butyl, t-butyl, sec-butyl, 1-pentyl, i-pentyl, sec-pentyl, t-pentyl, methylbutyl, 1,1-dimethylpropyl, 1-hexyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 2,2-dimethylbutyl, 3,3-dimethylbutyl, 1-ethyl-1-methylpropyl, 1-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 4-ethylpentyl, 1,1-dimethylpentyl, 2,2-dimethylpentyl, 3,3-dimethylpentyl, 4,4-dimethylpentyl, 1-propylbutyl, 1-octyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 4-ethylhexyl, 5-ethylhexyl, 1,1-dimethylhexyl, 2,2-dimethylhexyl, 3,3-dimethylhexyl, 4,4-dimethylhexyl, 5,5-dimethylhexyl, 1-propylpentyl, 2-propylpentyl and the like.

Of these, particularly preferred is alkyl having 1 to 0.6 carbon atoms.

"Alkenyl" and "alkenyl moiety" are preferably exemplified by linear or branched alkenyl, such as ethenyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl and the like.

Of these, preferred is alkenyl having 2 to 6 carbon atoms, and more preferably ethenyl.

"Cyclo(lower)alkyl" is cycloalkyl having 3 to 10, preferably 3 to 7, carbon atoms. Preferable examples thereof include cyclopropyl, cyclobutyl, cyclopentyl, cyclohexyl and cycloheptyl, with more preference given to cyclopropyl, cyclobutyl, cyclopentyl and cyclohexyl.

Examples of preferable "lower alkylene" include methylene, ethylene, propylene, butylene, pentylene, hexylene and the like, with particular preference given to alkylene having up to 4 carbon atoms. Of these, particularly preferred is methylene.

Examples of preferable "lower alkynyl" include linear or branched alkynyl, such as ethynyl, 1-propynyl, 2-propynyl, 1-butynyl, 2-butynyl, 3-butynyl, 1-pentynyl, 2-pentynyl, 3-pentynyl, 4-pentynyl, 2-methyl-3-butynyl, 1,1-dimethyl-2-butynyl, 1-hexynyl, 5-hexynyl and the like.

Of these, particularly preferred is alkynyl having 2 to 6 carbon atoms, which is more preferably ethynyl.

Examples of preferable "lower alkenylene" include linear or branched alkenylene, such as ethenylene, 1-propenylene, 2-propenylene, 1-butenylene, 2-butenylene, 3-butenylene, 1-pentenylene, 2-pentenylene, 3-pentenylene, 4-pentenylene, 1-hexenylene, 2-hexenylene, 3-hexenylene, 4-hexenylene, 5-hexenylene, methyl ethenylene, ethyl ethenylene, 1-pentyl ethenylene and the like.

Of these, particularly preferred is alkenylene having up to 4 carbon atoms, more preferably ethenylene.

"Lower alkoxy" is linear or branched alkyloxy having up to 6 carbon atoms. Preferable examples thereof include methoxy, ethoxy, 1-propyloxy, i-propyloxy, 1-butyloxy, i-butyloxy, sec-butyloxy, t-butyloxy, 1-pentyloxy, i-pentyloxy, sec-pentyloxy, t-pentyloxy, 2-methylbutoxy, 1-hexyloxy, i-hexyloxy, t-hexyloxy, sec-hexyloxy, 2-methylpentyloxy, 3-methylpentyloxy, 1-ethylbutyloxy, 2-ethylbutyloxy, 1,1-dimethylbutyloxy, 2,2-dimethylbutyloxy, 3,3-dimethylbutyloxy, 1-ethyl-1-methylpropyloxy, and the like.

More preferred is alkoxy having up to 5 carbon atoms, such as methoxy, ethoxy, 1-propyloxy, i-propyloxy, 1-butyloxy, i-butyloxy, sec-butyloxy, t-butyloxy, 1-pentyloxy and the like.

"Halogen" is exemplified by fluorine atom, chlorine atom, bromine atom and iodine atom.

"Halo(lower)alkyl" is a linear or branched alkyl having up to 6 carbon atoms, which is substituted by fluorine atom, chlorine atom, bromine atom or iodine atom, and is preferably exemplified by a linear or branched alkyl having up to 6 carbon atoms, which is substituted by fluorine atom, chlorine atom or bromine atom. Examples thereof include fluoromethyl, difluoromethyl, trifluoromethyl, chloromethyl, dichloromethyl, trichloromethyl, bromomethyl, dibromomethyl, tribromomethyl, 1-fluoroethyl, 1-chloroethyl, 1-bromoethyl, 2-fluoroethyl, 2-chloroethyl, 2-bromoethyl, 1,2-difluoroethyl, 1,2-dichloroethyl, 1,2-dibromoethyl, 2,2,2-trifluoroethyl, heptafluoroethyl, 1-fluoropropyl, 1-chloropropyl, 1-bromopropyl, 2-fluoropropyl, 2-chloropropyl, 2-bromopropyl, 3-fluoropropyl, 3-chloropropyl, 3-bromopropyl, 1,2-difluoropropyl, 1,2-dichloropropyl, 1,2-dibromopropyl, 2,3-difluoropropyl, 2,3-dichloropropyl, 2,3-dibromopropyl, 3,3,3-trifluoropropyl, 2,2,3,3,3-pentafluoropropyl, 2-fluorobutyl, 2-chlorobutyl, 2-bromobutyl, 4-fluorobutyl, 4-chlorobutyl, 4-bromobutyl, 4,4,4-trifluorobutyl, 2,2,3,3,4,4,4-heptafluorobutyl, perfluorobutyl, 2-fluoropentyl, 2-chloropentyl, 2-bromopentyl, 5-fluoropentyl, 5-chloropentyl, 5-bromopentyl, perfluoropentyl, 2-fluorohexyl, 2-chlorohexyl, 2-bromohexyl, 6-fluorohexyl, 6-chlorohexyl, 6-bromohexyl, perfluorohexyl and the like.

"Lower alkylthio" is a linear or branched alkylthio having up to 6 carbon atoms, which is preferably exemplified by methylthio, ethylthio, n-propylthio, i-propylthio, n-butylthio, i-butylthio, sec-butylthio, t-butylthio, n-pentylthio, i-pentylthio, sec-pentylthio, t-pentylthio, 2-methylbutylthio, n-hexylthio, i-hexylthio, t-hexylthio, sec-hexylthio, 2-methylpentylthio, 3-methylpentylthio, 1-ethylbutylthio, 2-ethylbutylthio, 1,1-dimethylbutylthio, 2,2-dimethylbutylthio, 3,3-dimethylbutylthio, 1-ethyl-1-methylpropylthio and the like.

More preferably, alkylthio having up to 4 carbon atoms, such as methylthio, ethylthio, n-propylthio, i-propylthio, n-butylthio, i-butylthio, sec-butylthio, t-butylthio and the like, is exemplified.

In the present specification, "aryl" and "aryl moiety" are each unsubstituted aryl or alkyl-substituted aryl. Examples of preferable unsubstituted aryl include $C_6$–$C_{10}$ aryl, such as phenyl, naphthyl and pentalenyl. Of these, preferred are phenyl and naphthyl.

"Alkyl-substituted aryl" means aryl substituted by at least one alkyl. The number of alkyl substituents is preferably 1 to 4. The aryl moiety of "alkyl-substituted aryl" is the same as for the aforementioned unsubstituted aryl, and the "alkyl moiety" is as defined above, which is preferably lower alkyl. Specific examples of preferable alkyl-substituted aryl include tolyl, xylyl, mesityl, ethylphenyl, propylphenyl and the like, with more preference given to p-tolyl.

"Heterocyclic group" is a saturated or unsaturated, heteromonocyclic or heteropolycyclic group having at least one hetero atom, such as oxygen atom, sulfur atom, nitrogen atom and selenium atom. Of these, unsaturated heteromonocyclic group is preferable. More preferred are the heterocyclic groups described in the below-mentioned (1), (7) and (9), which are particularly preferably pyridyl, thienyl and furyl.

Heteromonocyclic group includes the following.

(1) Unsaturated 3 to 8-membered (more preferably 5- or 6-membered) heteromonocyclic group having 1 to 4 nitrogen atoms, such as pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl and 2H-1,2,3-triazolyl), tetrazolyl (e.g., 1H-tetrazolyl and 2H-tetrazolyl) and the like.

(2) Saturated 3 to 8-membered (more preferably 5- or 6-membered) heteromonocyclic group having 1 to 4 nitrogen atoms, such as pyrrolidinyl, imidazolidinyl, piperidyl, pyperazinyl and the like.

(3) Unsaturated 3 to 8-membered (more preferably 5- or 6-membered) heteromonocyclic group having 1 or 2 oxygen atoms and 1 to 3 nitrogen atoms, such as oxazolyl, isoxazolyl, oxadiazolyl (e.g., 1,2,4-oxadiazolyl, 1,3,4-oxadiazolyl and 1,2,5-oxadiazolyl) and the like.

(4) Saturated 3 to 8-membered (more preferably 5- or 6-membered) heteromonocyclic group having 1 or 2 oxygen atoms and 1 to 3 nitrogen atoms, such as morpholinyl, sydnonyl and the like.

(5) Unsaturated 3 to 8-membered (more preferably 5- or 6-membered) heteromonocyclic group having 1 or 2 sulfur atoms and 1 to 3 nitrogen atoms, such as thiazolyl, isothiazolyl, thiadiazolyl (e.g., 1,2,3-thiadiazolyl, 1,2,4-thiadiazolyl, 1,3,4-thiadiazolyl and 1,2,5-thiadiazolyl), dihydrothiazinyl and the like.

(6) Saturated 3 to 8-membered (more preferably 5- or 6-membered) heteromonocyclic group having 1 or 2 sulfur atoms and 1 to 3 nitrogen atoms, such as thiazolidinyl and the like.

(7) Unsaturated 3 to 8-membered (more preferably 5- or 6-membered) heteromonocyclic group having 1 or 2 sulfur atoms, such as thienyl, dihydrodithinyl, dihydrodithionyl and the like.

(8) Saturated 3 to 8-membered (more preferably 5- or 6-membered) heteromonocyclic group having 1 or 2 oxygen atoms, such as tetrahydrofuryl, tetrahydropyranyl and the like.

(9) Unsaturated 3 to 8-membered (more preferably 5- or 6-membered) heteromonocyclic group having one oxygen atom, such as furyl and the like.

(10) Spiroheterocyclic group having 1 or 2 oxygen atoms, such as dioxaspiroundecanyl (e.g., 1,5-dioxaspiro[5,5]undecanyl) and the like.

(11) Unsaturated 3 to 8-membered (more preferably 5- or 6-membered) heteromonocyclic group having one oxygen atom and 1 or 2 sulfur atoms, such as dihydroxathinyl.

Examples of heteropolycyclic group include the following.

(12) Saturated or unsaturated 7 to 12-membered (more preferably 8 to 10-membered) heteropolycyclic (more preferably heterodicyclic) group having 1 to 4 nitrogen atoms.

Specific examples thereof include benzimidazolyl, indolyl, 2,3-dihydrobenzimidazolyl, pyrazolopyrimidinyl (e.g., pyrazolo[1,5-a]pyrimidinyl), tetrahydropyrazolopyrimidinyl (e.g., 4,5,6,7-tetrahydropyrazolo[1,5-a]pyrimidinyl), imidazopyrazolyl (e.g., 4H-imidazo[1,2-b]pyrazolyl), dihydroimidazopyrazolyl (e.g., 2,3-dihydroimidazo[1,2-b]pyrazolyl), imidazopyridyl (e.g., imidazo[1,5-a](or [1,2-a]or [3,4-a])pyridyl, 1H (or 3H)-imidazo[4,5-b](or [4,5-c])pyridyl), pyrrolopyridyl (e.g., 1H-pyrrolo[3,2-b]pyridyl), pyrazolopyridyl (e.g., pyrazolo[1,5-a](or [2,3-a]pyridyl, 1H (or 2H)-pyrazolo[4,3-b]pyridyl), benzopyrazolyl (e.g., 1H (or 2H)-benzo[c]pyrazolyl), dihydrobenzimidazolyl, benzotriazolyl (e.g., benzo[d][1H-1,2,3]triazolyl), indolidinyl, isoindolyl (e.g., 1H-isoindolyl), indazolyl (e.g., 1H (or 2H or 3H)-indazolyl), indolinyl, isoindolinyl, purinyl, quinolidinyl (e.g., 4H-quinolidinyl), isoquinolyl, quinolyl, phthaladinyl, naphthalidinyl (e.g., 1,8-naphthalidinyl), quinoxalinyl, dihydroquinoxalinyl (e.g., 1,2-dihydroquinoxalinyl), tetrahydroquinoxalinyl (e.g., 1,2,3,4-tetrahydroquinoxalinyl), quinazolinyl, dihydroquinazolinyl (e.g., 1,4 (or 3,4)-dihydroquinazolinyl), tetrahydroquinazolinyl (e.g., 1,2,3,4-tetrahydroquinazolinyl), cinnolinyl, pteridinyl, pyrazinopyridazinyl (e.g., pyrazino[2,3-d]pyridazinyl), imidazotriazinyl (e.g., imidazo[1,2-b][1,2,4]triazinyl), imidazopyrazinyl (e.g., 1H-imidazo[4,5-b]pyrazinyl), imidazopyrimidine (e.g., 3H-purine and imidazo[1,5-a] (or [3,4-a])pyrimidine), imidazopyridazinyl (e.g., imidazo[2,3-b](or [3,4-b])-pyridazinyl), 1H-1-(or 2)pyrimidinyl and the like.

(13) Saturated or unsaturated 7 to 12-membered (more preferably 8 to 10-membered) heteropolycyclic (more preferably heterodicyclic) group having 1 to 3 oxygen atoms.

Specific examples thereof include benzofuranyl (e.g., benzo[b](or [c])furanyl), isobenzofuranyl, furopyridyl, chromenyl (e.g., 2H-chromenyl), chromanyl, isochromanyl, benzoxepinyl (e.g., 3-benzoxepinyl), cyclopentapyranyl (e.g., cyclopenta[b]pyranyl), furopyranyl (e.g., 2H-furo[3,2-b]pyranyl, and the like.

(14) Saturated or unsaturated 7 to 12-membered (more preferably 8 to 10-membered) heteropolycyclic (more preferably heterodicyclic) group having 1 to 3 sulfur atoms.

Specific examples thereof include benzothiophenyl (e.g., benzo[b]thiophenyl), dihydrodithianaphthalenyl (e.g., 4H-1,3-dithianaphthalenyl), dithianaphthalenyl (e.g., 1,4-dithianaphthalenyl) and the like.

(15) Saturated or unsaturated 7 to 12-membered (more preferably 8 to 10-membered) heteropolycyclic (more preferably heterodicyclic) group having 1 to 3 nitrogen atoms and 1 or 2 oxygen atoms.

Specific examples thereof include dioxoloimidazolyl (e.g., 4H-1,3-dioxolo[4,5-d]imidazolyl, benzoxazinyl (e.g., 4H-3,1-benzoxazinyl), pyridooxazinyl (e.g., 5H-pyrido[2,3-d]oxazinyl), pyrazoloxazolyl (e.g., 1H-pyrazolo[4,3-d]oxazolyl), furopyridyl, and the like.

(16) Saturated or unsaturated 7 to 12-membered (more preferably 8 to 10-membered) heteropolycyclic (more preferably heterodicyclic) group having 1 to 3 nitrogen atoms and 1 or 2 sulfur atoms.

Specific examples thereof include thienoimidazolyl (e.g., thieno[2,3-d]imidazolyl), thienopyridyl, dithiadiazaindanyl (e.g., 2,3-dithia-1,5-diazaindanyl) and the like.

(17) Saturated or unsaturated 7 to 12-membered (more preferably 8 to 10-membered) heteropolycyclic (more preferably heterodicyclic) group having 1 to 3 oxygen atoms and 1 or 2 sulfur atoms.

Specific examples thereof include thienofuranyl (e.g., thieno[2,3-b]furanyl) and the like.

(18) Saturated or unsaturated 7 to 12-membered (more preferably 8 to 10-membered) heteropolycyclic (more preferably heterodicyclic) group having 1 nitrogen atom, 1 oxygen atom and 1 sulfur atom.

Specific examples thereof include oxathiolopyrrolyl (e.g., 4H[1,3]-oxathiolo[5,4-b]pyrrolyl) and the like.

(19) Saturated or unsaturated 7 to 12-membered (more preferably 8 to 10-membered) heteropolycyclic (more preferably heterodicyclic) group having 1 or 2 selenium atoms.

Preferable examples thereof include benzoselenophenyl (e.g., benzo[b](or [c])selenophenyl) and the like.

(20) Saturated or unsaturated 7 to 12-membered (more preferably 8 to 10-membered) heteropolycyclic (more preferably heterodicyclic) group having 1 or 2 selenium atoms and 1 to 3 nitrogen atoms.

Specific examples thereof include selenopyridyl (e.g., seleno[3,2-b]pyridyl) and the like.

The preferable "aryl moiety" of "aryloxy" is the above-mentioned "aryl moiety", which is more preferably phenyl.

"Protected carboxy" is preferably esterified carboxy.

Examples of preferable ester moiety of the esterified carboxy include:

lower alkyl esters, such as methyl ester, ethyl ester, propyl ester, isopropyl ester, butyl ester, isobutyl ester, t-butyl ester, pentyl ester and hexyl ester, optionally having at least one appropriate substituent, which is exemplified by lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 1 (or 2)-acetoxyethyl ester, 1 (or 2 or 3)-acetoxypropyl ester, 1 (or 2, 3 or 4)-acetoxybutyl ester, 1 (or 2)-propionyloxyethyl ester, 1 (or 2 or 3)-propionyloxypropyl ester, 1 (or 2)-butyryloxyethyl ester, 1 (or 2)-isobutyryloxyethyl ester, 1 (or 2)-pivaloyloxyethyl ester, 1 (or 2)-hexanoyloxyethyl ester, isobutyryloxymethyl ester, 2-ethylbutyryloxymethyl ester, 3,3-dimethylbutyryloxymethyl ester, 1 (or 2)-pentanoyloxyethyl ester), lower alkanesulfonyl(lower)alkyl ester (e.g., 2-mesylethyl ester), mono- (or di- or tri-)-halo(lower)alkyl ester (e.g., 2-iodoethyl ester and 2,2,2-trichloroethyl ester), lower alkoxycarbonyloxy (lower)alkyl ester (e.g., methoxycarbonyloxymethyl ester, ethoxycarbonyloxymethyl ester, 2-methoxycarbonyloxyethyl ester, 1-ethoxycarbonyloxyethyl ester and 1-isopropoxycarbonyloxyethyl ester), phthalidilidene(lower)alkyl ester and (5-lower alkyl-2-oxo-1,3-dioxol- 4-yl)(lower)alkyl ester (e.g., (5-methyl-2-oxo-1,3-dioxol-4-yl)methyl ester, (5-ethyl-2-oxo-1,3-dioxol-4-yl)methyl ester and (5-propyl-2-oxo-1,3-dioxol-4-yl)ethyl ester);

lower alkenyl ester (e.g., vinyl ester and allyl ester);

lower alkynyl ester (e.g., ethynyl ester and propynyl ester);

aryl(lower)alkyl ester optionally having at least one suitable substituent, such as mono- (or di- or tri-)phenyl(lower)alkyl ester optionally having at least one suitable substituent, which is exemplified by benzyl ester, 4-methoxybenzyl ester, 4-nitrobenzyl ester, phenylethyl ester, trityl ester, benzhydryl ester, bis(methoxyphenyl)methyl ester, 3,4-dimethoxybenzyl ester and 4-hydroxy-3,5-di-t-butylbenzyl ester;

aryl ester optionally having at least one suitable substituent, such as phenyl ester, 4-chlorophenyl ester, tolyl ester, t-butylphenyl ester, xylyl ester, mesityl ester and cumenyl ester; cyclo(lower)alkyl ester (e.g., cyclohexyl ester);

phthalidyl ester; and the like.

When the above-mentioned substituents are substituted, the number of the substituents is preferably 1 to 4, unless particularly specified.

Preferable examples of the objective compound (I) is a compound of the formula (IA):

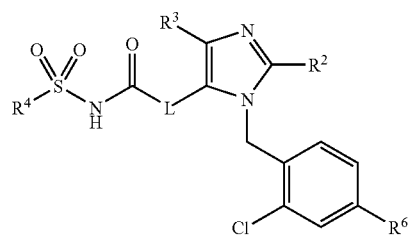

(IA)

wherein

R$^2$ is methyl;

R$^3$ is chlorine;

R$^4$ is (1) lower alkenyl optionally substituted by aryl, (2) aryl, (3) lower alkyl, or (4) heterocyclic group optionally substituted by halogen;

R$^6$ is (1) aryl, (2) heterocyclic group, (3) bromine, (4) halo(lower)alkyl, (5) lower alkylthio, (6) nitro, (7) lower alkenyl substituted by aryl, (8) lower alkynyl substituted by aryl, (9) lower alkoxy optionally substituted by cyclo(lower)alkyl or aryl, (10) lower alkyl optionally substituted by aryloxy, or (11) amino optionally substituted by protected carboxy or lower alkyl; and L is ethenylene and a salt thereof.

Of the above-mentioned compounds (IA), a compound wherein R$^4$ is aryl or lower alkenyl optionally substituted by aryl, R$^6$ is bromine, lower alkenyl substituted by aryl, lower alkynyl substituted by aryl or lower alkoxy optionally substituted by cyclo(lower)alkyl and a salt thereof are particularly preferable.

Of the above-mentioned compounds (I), a compound wherein R is heterocyclic group substituted by a substituent selected from the group consisting of (1) aryl, (2) heterocyclic group, (3) halogen, (4) halo(lower)alkyl, (5) lower alkylthio, (6) nitro, (7) lower alkenyl optionally substituted by aryl, (8) lower alkynyl optionally substituted by aryl, (9) lower alkoxy optionally substituted by cyclo(lower)alkyl or aryl, (10) aryloxy and (11) amino optionally substituted by protected carboxy or lower alkyl, and a salt thereof are more preferable.

Of these, particularly preferable groups are specifically exemplified by the following.

R$^1$: 2-chloro-4-(2-furyl)phenyl, 2-chloro-4-(2-thienyl)phenyl, 2-chloro-4-(phenylethynyl)phenyl, 4-bromo-2-chlorophenyl, 3-chloro-4-biphenylyl, 2-chloro-4-(1-propoxy) phenyl, 2-chloro-4-(1-pentyloxy)phenyl, 2-chloro-4-((cyclopentyl)methyloxy)phenyl, 2-chloro-4-((cyclohexyl)methyloxy)phenyl, 4-benzyloxy-2-chlorophenyl, 2-chloro-4-(methylthio)phenyl, 2-chloro-4-(trifluoromethyl)phenyl, 2-chloro-4-(phenoxymethyl)

phenyl, 2-chloro-4-nitrophenyl, 2-chloro-4-((E)-2-phenylethenyl)phenyl, 1-bromo-2-naphthyl, $R^2$: methyl, $R^3$: chlorine, $R^4$: p-tolyl, (E)-2-phenylethenyl, pentyl, phenyl, 5-chloro-2-thienyl, 5-bromo-2-thienyl, $R^6$: 2-furyl, 2-thienyl, phenylethynyl, bromine, phenyl, 1-propoxy, 1-pentyloxy, (cyclopentyl)methyloxy, (cyclohexyl)methyloxy, benzyloxy, methylthio, trifluoromethyl, phenoxymethyl, nitro, (E)-2-phenylethenyl, A: methylene, L: ethenylene.

Preferable specific compounds as the objective compound (I) are exemplified by the following.

(1) (E)-3-(4-chloro-1-(2-chloro-4-(2-furyl)benzyl)-2-methylimidazol-5-yl)-N-((4-methylbenzene)sulfonyl)-2-propenamide, (2) (2E)-3-(4-chloro-1-(2-chloro-4-(2-furyl)benzyl)-2-methylimidazol-5-yl)-N-(((E)-2-phenylethenyl)sulfonyl)-2-propenamide, (3) (E)-3-(4-chloro-1-(2-chloro-4-(2-thienyl)benzyl)-2-methylimidazol-5-yl)-N-((4-methylbenzene)sulfonyl)-2-propenamide, (4) (2E)-3-(4-chloro-1-(2-chloro-4-(2-thienyl)benzyl)-2-methylimidazol-5-yl)-N-(((E)-2-phenylethenyl)sulfonyl)-2-propenamide, (5) (E)-3-(4-chloro-1-(2-chloro-4-(phenylethynyl)benzyl)-2-methylimidazol-5-yl)-N-((4-methylbenzene)sulfonyl)-2-propenamide, (6) (2E)-3-(4-chloro-1-(2-chloro-4-(phenylethynyl)benzyl)-2-methylimidazol-5-yl)-N-(((E)-2-phenylethenyl)sulfonyl)-2-propenamide, (7) (E)-3-(1-(4-bromo-2-chlorobenzyl)-4-chloro-2-methylimidazol-5-yl)-N-((4-methylbenzene)sulfonyl)-2-propenamide, (8) (E)-3-(1-(4-bromo-2-chlorobenzyl)-4-chloro-2-methylimidazol-5-yl)-N-(((E)-2-phenylethenyl)sulfonyl)-2-propenamide, (9) (E)-3-[4-chloro-1-(2-chloro-4-phenylbenzyl)-2-methylimidazol-5-yl]-N-(1-pentanesulfonyl)-2-propenamide,

(10) (E)-N-benzenesulfonyl-3-[4-chloro-1-(2-chloro-4-phenylbenzyl)-2-methylimidazol-5-yl]-2-propenamide,

(11) (E)-3-[4-chloro-1-(2-chloro-4-phenylbenzyl)-2-methylimidazol-5-yl]-N-((4-methylbenzene)sulfonyl)-2-propenamide,

(12) (E)-3-(4-chloro-1-(2-chloro-4-phenylbenzyl)-2-methylimidazol-5-yl)-N-(((E)-2-phenylethenyl)sulfonyl)-2-propenamide,

(13) (E)-3-(4-chloro-1-(2-chloro-4-phenylbenzyl)-2-methylimidazol-5-yl)-N-((5-chloro-2-thienyl)sulfonyl)-2-propenamide,

(14) (E)-N-((5-bromo-2-thienyl)sulfonyl)-3-(4-chloro-1-(2-chloro-4-phenylbenzyl)-2-methylimidazol-5-yl)-2-propenamide,

(15) (E)-3-((4-chloro-1-(2-chloro-4-(1-propoxy)benzyl)-2-methylimidazol-5-yl)-N-((4-methylbenzene)sulfonyl)-2-propenamide,

(16) (E)-3-(4-chloro-1-(2-chloro-4-(1-propoxy)benzyl)-2-methylimidazol-5-yl)-N-(((E)-2-phenylethenyl)sulfonyl)-2-propenamide,

(17) (E)-3-(4-chloro-1-(2-chloro-4-(1-pentyloxy)benzyl)-2-methylimidazol-5-yl)-N-((4-methylbenzene)sulfonyl)-2-propenamide,

(18) (E)-3-(4-chloro-1-(2-chloro-4-(1-pentyloxy)benzyl)-2-methylimidazol-5-yl)-N-(((E)-2-phenylethenyl)sulfonyl)-2-propenamide,

(19) (E)-3-(4-chloro-1-(2-chloro-4-((cyclopentyl)methyloxy)-benzyl)-2-methylimidazol-5-yl)-N-(1-pentanesulfonyl)-2-propenamide,

(20) (E)-3-(4-chloro-1-(2-chloro-4-((cyclopentyl)methyloxy)-benzyl)-2-methylimidazol-5-yl)-N-((4-methylbenzene)sulfonyl)-2-propenamide,

(21) (2E)-3-(4-chloro-1-(2-chloro-4-((cyclopentyl)methyloxy)-benzyl)-2-methylimidazol-5-yl)-N-(((E)-2-phenylethenyl)sulfonyl)-2-propenamide,

(22) (E)-3-(4-chloro-1-(2-chloro-4-((cyclohexyl)methyloxy)-benzyl)-2-methylimidazol-5-yl)-N-((4-methylbenzene)sulfonyl)-2-propenamide,

(23) (2E)-3-(4-chloro-1-(2-chloro-4-((cyclohexyl)methyloxy)-benzyl)-2-methylimidazol-5-yl)-N-(((E)-2-phenylethenyl)sulfonyl)-2-propenamide,

(24) (E)-3-(1-(4-benzyloxy-2-chlorobenzyl)-4-chloro-2-methylimidazol-5-yl)-N-((4-methylbenzene)sulfonyl)-2-propenamide,

(25) (E)-3-(1-(4-benzyloxy-2-chlorobenzyl)-4-chloro-2-methylimidazol-5-yl)-N-(((E)-2-phenylethenyl)sulfonyl)-2-propenamide,

(26) (E)-3-(4-chloro-1-(2-chloro-4-(methylthio)benzyl)-2-methylimidazol-5-yl)-N-((4-methylbenzene)sulfonyl)-2-propenamide,

(27) (E)-3-(4-chloro-1-(2-chloro-4-(methylthio)benzyl)-2-methylimidazol-5-yl)-N-(((E)-2-phenylethenyl)sulfonyl)-2-propenamide,

(28) (E)-3-(4-chloro-1-(2-chloro-4-(trifluoromethyl)benzyl)-2-methylimidazol-5-yl)-N-((4-methylbenzene)sulfonyl)-2-propenamide,

(29) (E)-3-(4-chloro-1-(2-chloro-4-(trifluoromethyl)benzyl)-2-methylimidazol-5-yl)-N-(((E)-2-phenylethenyl)sulfonyl)-2-propenamide,

(30) (E)-3-(4-chloro-1-(2-chloro-4-(phenoxymethyl)benzyl)-2-methylimidazol-5-yl)-N-((4-methylbenzene)sulfonyl)-2-propenamide,

(31) (E)-3-(4-chloro-1-(2-chloro-4-(phenoxymethyl)benzyl)-2-methylimidazol-5-yl)-N-(((E)-2-phenylethenyl)sulfonyl)-2-propenamide,

(32) (E)-3-(4-chloro-1-(2-chloro-4-nitrobenzyl)-2-methylimidazol-5-yl)-N-((4-methylbenzene)sulfonyl)-2-propenamide,

(33) (E)-3-(4-chloro-1-(2-chloro-4-nitrobenzyl)-2-methylimidazol-5-yl)-N-(((E)-2-phenylethenyl)sulfonyl)-2-propenamide,

(34) (E)-3-(4-chloro-1-(2-chloro-4-((E)-2-phenylethenyl)benzyl)-2-methylimidazol-5-yl)-N-((4-methylbenzene)sulfonyl)-2-propenamide,

(35) (E)-3-(4-chloro-1-(2-chloro-4-((E)-2-phenylethenyl)benzyl)-2-methylimidazol-5-yl)-N-(((E)-2-phenylethenyl)sulfonyl)-2-propenamide,

(36) (E)-3-(1-(1-bromo-2-naphthyl)-4-chloro-2-methylimidazol-5-yl)-N-((4-methylbenzene)sulfonyl)-2-propenamide,

(37) (E)-3-(1-(1-bromo-2-naphthyl)-4-chloro-2-methylimidazol-5-yl)-N-(((E)-2-phenylethenyl)sulfonyl)-2-propenamide,

(38) (E)-3-(4-chloro-1-(2-chloro-4-(1-pentyloxy)benzyl)-2-methylimidazol-5-yl)-N-(1-pentanesulfonyl)-2-propenamide,

(39) (E)-3-(4-chloro-1-(2-chloro-4-(1-pentyloxy)benzyl)-2-methylimidazol-5-yl)-N-((E)-1-penten-1-ylsulfonyl)-2-propenamide,

(40) (E)-N-(1-butanesulfonyl)-3-(4-chloro-1-(2-chloro-4-(1-pentyloxy)benzyl)-2-methylimidazol-5-yl)-2-propenamide,

(41) (E)-3-(4-chloro-1-(2-chloro-4-((E)-2-phenylethenyl) benzyl)-2-methylimidazol-5-yl)-N-(1-pentanesulfonyl)-2-propenamide,

(42) (E)-(3-(4-chloro-1-(2-chloro-4-((E)-2-phenylethenyl) benzyl)-2-methylimidazol-5-yl)-N-((E)-1-penten-1-ylsulfonyl)-2-propenamide,

(43) (E)-N-(1-butanesulfonyl)-3-(4-chloro-1-(2-chloro-4-(((E)-2-phenylethenyl)benzyl)-2-methylimidazol-5-yl)-2-propenamide,

(44) (E)-3-(4-chloro-1-(2-chloro-4-(phenylethynyl)benzyl)-2-methylimidazol-5-yl)-N-(1-pentanesulfonyl)-2-propenamide,

(45) (E)-3-(4-chloro-1-(2-chloro-4-(phenylethynyl)benzyl)-2-methylimidazol-5-yl)-N-((E)-1-penten-1-ylsulfonyl)-2-propenamide,

(46) (E)-N-(1-butanesulfonyl)-3-(4-chloro-1-(2-chloro-4-(2-phenylethynyl)benzyl)-2-methylimidazol-5-yl)-2-propenamide,

(47) (E)-3-(4-chloro-1-((3-chloro-5-(trifluoromethyl)pyridin-2-yl)methyl)-2-methylimidazol-5-yl)-N-((E)-2-phenylethenylsulfonyl)-2-propenamide,

(48) (E)-3-(4-chloro-1-((3-chloro-5-(trifluoromethyl)pyridin-2-yl)methyl)-2-methylimidazol-5-yl)-N-((4-methylbenzene)sulfonyl)-2-propenamide,

(49) (E)-3-(1-(4-(tert-butoxycarbonylamino)-2-chlorobenzyl)-4-chloro-2-methylimidazol-5-yl)-N-(1-pentanesulfonyl)-2-propenamide,

(50) (E)-3-(1-(4-(tert-butoxycarbonylamino)-2-chlorobenzyl)-4-chloro-2-methylimidazol-5-yl)-N-((E)-1-penten-1-ylsulfonyl)-2-propenamide,

(51) (E)-3-(1-(4-(tert-butoxycarbonylamino)-2-chlorobenzyl)-4-chloro- 2-methylimidazol-5-yl)-N-(((E)-2-phenylethenyl)sulfonyl)-2-propenamide,

(52) (E)-3-(4-chloro-1-(2-chloro-4-(1-pentyloxy)benzyl)-2-ethylimidazol-5-yl)-N-((E)-2-phenylethenesulfonyl)-2-propenamide,

(53) (E)-3-(1-(4-bromo-2-chlorobenzyl)-4-chloro-2-ethylimidazol-5-yl)-N-((E)-2-phenylethenesulfonyl)-2-propenamide,

(54) (E)-3-(4-chloro-1-(2-chloro-4-(phenylethynyl)benzyl)-2-ethylimidazol-5-yl)-N-((E)-2-phenylethenesulfonyl)-2-propenamide,

(55) (E)-3-(4-chloro-1-(2-chloro-4-(phenylethynyl)benzyl)-2-ethylimidazol-5-yl)-N-((4-methylbenzene)sulfonyl)-2-propenamide,

(56) (E)-N-(1-butanesulfonyl)-3-(4-chloro-1-(2-chloro-4-(phenylethynyl)benzyl)-2-ethylimidazol-5-yl)-2-propenamide,

(57) (E)-3-(4-chloro-1-(2-chloro-4-(phenylethynyl)benzyl)-2-ethylimidazol-5-yl)-N-(1-pentanesulfonyl)-2-propenamide,

(58) (E)-3-(4-chloro-1-(2-chloro-4-(phenylethynyl)benzyl)-2-ethylimidazol-5-yl)-N-((E)-1-penten-1-ylsulfonyl)-2-propenamide,

(59) (E)-3-(4-chloro-1-(2-chloro-4-((E)-2-phenylethenyl) benzyl)-2-ethylimidazol-5-yl)-N-((E)-2-phenylethenesulfonyl)-2-propenamide,

(60) (E)-3-(4-chloro-1-(2-chloro-4-((E)-2-phenylethenyl) benzyl)-2-ethylimidazol-5-yl)-N-(4-methylbenzenesulfonyl)-2-propenamide,

(61) (E)-N-(1-butanesulfonyl)-3-(4-chloro-1-(2-chloro-4-((E)-2-phenylethenyl)benzyl)-2-ethylimidazol-5-yl)-2-propenamide,

(62) (E)-3-(4-chloro-1-(2-chloro-4-((E)-2-phenylethenyl) benzyl)-2-ethylimidazol-5-yl)-N-(1-pentanesulfonyl)-2-propenamide,

(63) (E)-3-(4-chloro-1-(2-chloro-4-((E)-2-phenylethenyl) benzyl)-2-ethylimidazol-5-yl)-N-((E)-1-penten-1-ylsulfonyl)-2-propenamide,

(64) (E)-3-(1-(4-bromo-2-chlorobenzyl)-2,4-dimethylimidazol-5-yl)-N-((E)-2-phenylethenesulfonyl)-2-propenamide,

(65) (E)-3-(4-bromo-1-(2-chloro-4-(1-pentyloxy)benzyl)-2-methylimidazol-5-yl)-N-((E)-2-phenylethenesulfonyl)-2-propenamide,

(66) (E)-3-(1-(2-chloro-4-(1-pentyloxy)benzyl)-4-ethyl-2-methylimidazol-5-yl)-N-((E)-2-phenylethenesulfonyl)-2-propenamide,

(67) (E)-2-benzyl-3-(1-(2-chloro-4-(1-pentyloxy)benzyl)-2-methylimidazol-5-yl)-N-((E)-2-phenylethenesulfonyl)-2-propenamide,

(68) (E)-3-(1-(2-chloro-4-(1-pentyloxy)benzyl)-2-methylimidazol-5-yl)-2-(1-pentyl)-N-((E)-2-phenylethenesulfonyl)-2-propenamide,

(69) (E)-3-(1-(2-chloro-4-(1-pentyloxy)benzyl)-2-methylimidazol-5-yl)-2-(3-pyridyl)methyl-N-((E)-2-phenylethenesulfonyl)-2-propenamide,

(70) (E)-3-(1-(2-chloro-4-(1-pentyloxy)benzyl)-2-methylimidazol-5-yl)- 2-methyl-N-((E)-2-phenylethenesulfonyl)-2-propenamide,

(71) (E)-3-(4-chloro-1-(2-chloro-4-(1-pentyloxy)benzyl)-2-ethylimidazol-5-yl)-2-methyl-N-((E)-2-phenylethenesulfonyl)-2-propenamide,

(72) 4-chloro-1-(2-chloro-4-(1-pentyloxy)benzyl)-2-methyl-5-((E)-2-phenylethenesulfonylcarbamoyl)-1H-imidazole,

(73) (4-chloro-1-(2-chloro-4-(1-pentyloxy)benzyl)-2-methyl-1H-imidazol-5-yl)methyl N-(4-methylbenzenesulfonyl)carbamate,

(74) 4-chloro-1-(2-chloro-4-(1-pentyloxy)benzyl)-5-((3-(4-methylbenzenesulfonyl)ureido)methyl)-2-methyl-1H-imidazole,

(75) 4-chloro-1-(2-chloro-4-(1-pentyloxy)benzyl)-5-((3-(4-methylbenzenesulfonyl)-1-methylureido)methyl)-2-methyl-1H-imidazole, and

(76) (E)-3-(4-chloro-1-(2-chloro-4-(phenylethynyl)benzyl)-2-ethylimidazol-5-yl)-N-((E)-1-penten-1-yl)-1-ylsulfonyl)-2-propenamide and sodium salt thereof.

The production methods of the objective compound (I) are explained in detail in the following.

Production Method 1:

The objective compound (I) and a salt thereof can be produced by reacting compound (II) or reactive derivative at carboxy thereof or a salt thereof with compound (III) or a salt thereof.

Examples of preferable salt of compound (II), reactive derivative at carboxy group thereof and compound (III) include those shown with regard to compound (I).

Preferable reactive derivative at carboxy of compound (II) is acid halide, acid anhydride inclusive of intramolecular acid anhydride, intermolecular acid anhydride and mixed acid anhydride, active amide, active ester and the like. Preferable examples thereof include acid chloride, acid azide, mixed acid anhydride with acid such as substituted phosphoric acid (e.g., dialkylphosphoric acid, phenylphosphoric acid, diphenylphosphoric acid, dibenzylphosphoric acid and halogenated phosphoric acid), dialkylphosphorous acid, sulfurous acid, thiosulfuric acid, sulfuric acid, sulfonic acid (e.g., methanesulfonic acid), aliphatic carboxylic acid (e.g., acetic acid, propionic acid, butyric acid, isobutyric acid, pivalic acid, pentanoic acid, isopentanoic acid, 2-ethylbutyric acid and trichloroacetic acid), aromatic carboxylic acid (e.g., benzoic acid) and the like; symmetric acid anhydride; active amide with imidazole, 4-substituted imidazole, dimethylpyrazole, triazole or tetrazole; active ester (e.g., cyanomethyl ester, methoxymethyl ester, dimethyliminomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthio ester, p-nitrophenylthio ester, p-cresylthio ester, carboxymethylthio ester, pyranyl ester, pyridyl ester, piperidyl ester and 8-quinolylthio ester); esters with N-hydroxy compound (e.g., N,N-dimethylhydroxylamine, 1-hydroxy-2-1H-pyridone, N-hydroxysuccinimide and 1-hydroxy-1H-benzotriazole); and the like. These reactive derivatives can be appropriately selected according to the kind of compound (II) to be used.

The reaction generally proceeds in a conventional solvent such as water, alcohol (e.g., methanol and ethanol), acetone, dioxane, acetonitrile, chloroform, methylene chloride, ethylene chloride, tetrahydrofuran, ethyl acetate, N,N-dimethylformamide and pyridine, or a mixture thereof, or in any other solvent which does not adversely affect the reaction. These conventional solvents may be used alone or in combination.

When compound (II) is used in the form of a free acid or a salt thereof in this reaction, the reaction is preferably carried out in the presence of a conventional condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylamino-propyl)carbodiimide, N,N'-carbonylbis(2-methylimidazole), pentamethyleneketen-N-cyclohexylimine, diphenylketene-N-cyclohexylimine, ethoxyacetylene, 1-alkoxy-1-chloroethylene, trialkyl phosphite, ethyl polyphosphate, isopropyl polyphosphate, phosphorous oxychloride (phosphoryl chloride), phosphorus trichloride, diphenylphosphoryl azide, diphenyl chlorophosphate, diphenylphosphinic chloride, thionyl chloride, oxaryl chloride, lower alkyl haloformate (e.g., ethyl chloroformate and isopropyl chloroformate), triphenylphosphine, 2-ethyl-7-hydroxybenzisoxazorium salt, intramolecular salt of 2-ethyl-5-(m-sulfophenyl)isoxazorium hydroxide, 1-(p-chlorobenzene-sulfonyloxy)-6-chloro-1H-benzotriazole, so-called Vilsmeier reagent(prepared by the reaction of N,N-dimethylformamide with thionyl chloride, phosgene, trichloromethyl chloroformate, phosphorous oxychloride, and so on), and the like.

The reaction can be carried out in the presence of an inorganic or organic base such as alkali metal bicarbonate, tri(lower)alkylamine, pyridine, 4-dimethylaminopyridine, N-(lower)alkylmorpholine, N,N-di(lower)alkylaniline (e.g., N,N-dimethylaniline), N,N-di(lower)alkylbenzylamine and the like.

The reaction temperature is not particularly limited, and the reaction is generally carried out under cooling to heating.

The aforementioned compounds can be converted to preferable salts as necessary by a conventional method. All of them can be purified as necessary according to a conventional method for purifying an organic compound (i.e., recrystallization, column chromatography, thin layer chromatography, high performance liquid chromatography and the like). The compound can be identified by NMR spectrum analysis, mass spectrum analysis, IR spectrum analysis, elemental anlysis, melting point measurement and the like.

The compound of the present invention may have one or more chiral centers and, therefore, may be present as enantiomers and diastereomers. Some compounds having alkenyl may be present as a cis or trans isomer. In any case, the present invention encompasses such mixtures and respective isomers.

The inventive compound and a salt thereof may be in the form of a solvate, which is also encompassed in the present invention. The solvate is preferably exemplified by hydrate and ethanol solvate.

The pharmaceutical data of compound (I) are shown in the following to demonstrate the utility of the objective compound (I).

EXPERIMENTAL EXAMPLE 1

(Blood Sugar Level Depressing Activity in db/db Mice)

Test Compound

Compound A:
(E)-3-[4-chloro-1-(2-chloro-4-phenylbenzyl)-2-methylimidazol-5-yl]-N-((4-methylbenzene)sulfonyl)-2-propenamide (compound of Example 11)

Animal
Female C57BL/KsJ-dbm db+/db+, C57BL/KsJ-dbm +m/+m (Jackson Laboratory) mice (5 weeks old) were purchased and subjected to the test after 2–3 weeks of acclimating period.

Drug Administration
The test drug was mixed with a powder diet (CE-2, Clea Japan, Inc.) in a mortar. In the case of administration in 100 mg/kg, the mixing proportion was 0.1%, in the case of 30 mg/kg, the proportion was 0.03% and in the case of 10 mg/kg, the proportion was 0.01%. The diet was changed twice a week for each group. The amount of the diet given and the amount left were recorded and the diet intake was calculated by determining the difference.

Test Schedule
The female db/db mice were grouped according to body weight, blood sugar level and triglyceride concentration in plasma. Then, the drug-mixed diet was given for 14 days, during which period the mice were 8 to 10 weeks of age. At day 7 and day 14 in the morning, blood was taken from orbital venous plexus using a heparinized glass capillary tube (Chase Heparinized Capillary Tube), and centrifuged to give plasma fractions. The blood sugar value, triglyceride concentration in plasma and insulin concentration in plasma were measured at day 0 and day 14, and blood sugar value and triglyceride concentration in plasma were measured at day 7. Body weight was measured at day 0, day 7 and day 14. After final blood sampling, the mice were sacrificed with $CO_2$ gas.

Measurement Method
Blood sugar value was measured using 10–15 µl of plasma and in accord with glucose oxidase method (glucose CII-Test Wako, Wako Pure Chemicals Co., Ltd.). The triglyceride concentration in plasma was measured using 10–15 µl of plasma and in accord with GPO-p-chlorophenol method (triglyceride G-Test Wako) or GPO-DAOS method (triglyceride E-Test Wako). The measurement was done promptly after blood sampling. The insulin concentration in plasma was measured using 20 µl of plasma (preservable at −20° C.) and in accord with an antibody method (Phadesef Insulin RIA kit, Kabi Pharmacia).

Result
Using the difference between db/db mice control group and +/+mice in blood sugar value and triglyceride concentration in plasma as 100%, the proportion (%) of decrease in the blood sugar value and triglyceride concentration in plasma of the group administered with the test drug was determined. The results are shown in Table 1.

TABLE 1

| Test compound | Dose (mg/kg) | Blood sugar decrease (%) |
| --- | --- | --- |
| Compound A | 3.2 | 63 |

The compound (I) of the present invention can be used for therapeutic purposes in the form of a pharmaceutical preparation. This pharmaceutical preparation contains any one of the compounds (I) as an active ingredient in admixture with a pharmaceutically acceptable organic or inorganic excipient which is a solid, semi-solid or liquid and which is suitable for oral, parenteral or external (local) administration. Examples of the pharmaceutical reparation include capsules, tablets, sugar coating tablets, granules, suppositories, liquid, lotion, suspension, emulsion, ointment, gel and the like. When desired, these preparations may contain adjuvant, auxiliary substance, stabilizer, moistening agent, emulsifier, buffering agent, and other conventional additives. While the dose of the compound (I) varies depending on the age and symptom of patients, for the therapy of the above-mentioned diseases, an average single dose amount of about 0.1 mg, 1 mg, 10 mg, 50 mg, 100 mg, 250 mg, 500 mg or 1000 mg of the compound (I) would be effective. In general, its daily dose is from 0.1 mg/patient to about 1000 mg/patient.

The present invention is described in more detail by way of the following Preparation Examples and Examples.

PREPARATION EXAMPLE 1-1

4,5-Dibromo-2-methylimidazole (4.91 g) was dissolved in N,N-dimethylformamide (50 ml), and 60% sodium hydride (901 mg) was added gradually under ice-cooling. After stirring at room temperature for 1 hour, 2-(trimethylsilyl)ethoxymethyl chloride (3.75 g) was gradually added dropwise under ice-cooling, and the mixture was stirred overnight at room temperature. The solvent was evaporated under reduced pressure and ethyl acetate was added to the residue. The reaction mixture was washed with saturated aqueous sodium hydrogencarbonate solution and brine. The organic layer was dried over anhydrous magnesium sulfate and the solvent was evaporated under reduced pressure. The residue was purified by silica gel column chromatography (hexane/ethyl acetate=3/1) to give 4,5-dibromo-2-methyl-1-((2-(trimethylsilyl)ethoxy)methyl)imidazole (7.6 g) as a colorless oil.

$^1$H-NMR(CDCl$_3$): 0.00(9H, s), 0.92(2H, t, J=8 Hz), 2.47 (3H, s), 3.55(2H, t, J=8 Hz), 5.24(2H, s).

PREPARATION EXAMPLE 1-2

4,5-Dibromo-2-methyl-1-((2-(trimethylsilyl)ethoxy)methyl)imidazole (29.2 g) was dissolved in tetrahydrofuran (250 ml), and 1.63N 1-butyl lithium/hexane solution (58.1 ml) was added dropwise over 20 min at from −55° C. to −60° C. The mixture was stirred at −60° C. for 30 min and N,N-dimethylformamide (58 g) was gradually added dropwise at from −55° C. to −60° C. The mixture was stirred at room temperature for 1 hr. Saturated brine was added and the mixture was extracted with ethyl acetate. The organic layer was dried over anhydrous sodium sulfate and the solvent was evaporated under reduced pressure. The residue was purified by silica gel column chromatography (hexane/ethyl acetate=3/1) to give 4-bromo-2-methyl-1-((2-(trimethylsilyl)ethoxy)methyl)-imidazole-5-carbaldehyde (18.5 g) as a pale-yellow oil.

$^1$H-NMR(CDCl$_3$): 0.00(9H, s), 0.91(2H, t, J=8 Hz), 2.52 (3H, s), 3.58(2H, t, J=8 Hz), 5.70(2H, s), 9.71(1H, s).

PREPARATION EXAMPLE 1-3

4-Bromo-2-methyl-1-((2-(trimethylsilyl)ethoxy)methyl) imidazole-5-carbaldehyde (18.5 g) was dissolved in ethanol (80 ml) and 6N hydrochloric acid (80 ml) was added. The mixture was refluxed under heating for 1 hr. The solvent was evaporated under reduced pressure and saturated aqueous sodium hydrogencarbonate solution was added under ice-cooling until the mixture assumed weak alkalinity. The precipitated crystals were collected by filtration, and the crystals were washed with methanol and heat-dried under reduced pressure to give 5-bromo-2-methylimidazole-4-carbaldehyde (9.17 g) as white crystals.

$^1$H-NMR(CDCl$_3$): 2.45(3H, s), 9.53(1H, s).

PREPARATION EXAMPLE 1-4

5-Bromo-2-methylimidazole-4-carbaldehyde (400 mg) was dissolved in conc. hydrochloric acid (6 ml), and the mixture was refluxed under heating for 24 hr. Saturated aqueous sodium hydrogencarbonate solution was added under ice-cooling until the mixture assumed weak alkalinity and the mixture was extracted twice with ethyl acetate. The organic layer was washed with saturated aqueous sodium hydrogencarbonate solution and then brine. The organic layer was dried over anhydrous magnesium sulfate and the solvent was evaporated under reduced pressure. Hexane was added to the residue and the crystals were collected by filtration to give 5-chloro-2-methylimidazole-4-carbaldehyde (222 mg) as yellow crystals.

$^1$H-NMR(CDCl$_3$): 2.45(3H, s), 9.58(1H, s).

PREPARATION EXAMPLE 2

To a solution of 2-chloro-4-iodotoluene (7.59 g) in carbon tetrachloride (76 ml) were added N-bromosuccinimide (5.89 g) and 2,2'-azobis(4-methoxy-2,4-dimethylvaleronitrile) (Wako V-70, 281 mg) at room temperature and the mixture was stirred at 55° C. for 3.5 hr. The reaction mixture was allowed to cool to room temperature and thereto was added hexane (76 ml). Insoluble matter was filtered off. The filtrate was concentrated and the residue was again dissolved in hexane. The mixture washed successively with water, 5% aqueous sodium thiosulfate solution, saturated aqueous sodium hydrogencarbonate solution and saturated brine, and dried over anhydrous magnesium sulfate. The solvent was evaporated to give 2-chloro-4-iodobenzyl bromide (8.45 g) as an oil.

$^1$H-NMR(CDCl$_3$): 4.52(2H, s), 7.16(1H, d, J=8 Hz), 7.59(1H, dd, J=8 and 2 Hz), 7.76(1H, d, J=2 Hz).

PREPARATION EXAMPLE 3-1

To a suspension of tetrakis(triphenylphosphine)palladium (213 mg) in toluene (7 ml) was added 2-chloro-4-iodotoluene (2.33 g) at room temperature. The mixture was stirred at room temperature for 30 min, and thereto were added a solution of phenylboronic acid (1.35 g) in EtOH (2 ml) and 2M aqueous sodium carbonate solution (9.25 ml), and the mixture was refluxed under heating. After 3 hr, the reaction mixture was cooled and the organic layer was separated. The aqueous layer was extracted with hexane (4 ml). The organic layers were combined, washed with saturated aqueous sodium hydrogencarbonate solution (4 ml) and saturated brine (4 ml), and dried over anhydrous magnesium sulfate. After filtration, the filtrate was concentrated, and hexane (10 ml) and silica gel (4 g) were added to the residue (2.11 g). The mixture was stirred at room temperature for 1 hr. Silica gel was filtered off and the filtrate was concentrated to give 2-chloro-4-phenyltoluene as a pale-brown oil (1.86 g, 99.4%).

$^1$H-NMR(CDCl$_3$): 2.40(3H, s), 7.23–7.60(8H, m).

PREPARATION EXAMPLE 3-2

In the same manner as in the aforementioned Preparation Example 2,2-chloro-4-phenylbenzyl bromide was obtained as colorless crystals (3.22 g) from 2-chloro-4-phenyltoluene (3.6 g).

$^1$H-NMR(CDCl$_3$): 4.64(2H, s), 7.35–7.63(8H, m). m.p. 73–74° C.

PREPARATION EXAMPLE 4-1

2-Chloro-4-iodotoluene (22.0 g) was dissolved in N,N-dimethylformamide (110 ml), and copper(I) iodide (49.8 g), ethyl chlorodifluoroacetate (37.8 g) and potassium fluoride (15.2 g) were added. The mixture was stirred at internal temperature of 116° C. for 70 hr. The reaction mixture was filtered through celite. Water (11 ml) and diethyl ether (110 ml) were added to the filtrate under ice-cooling and the mixture was filtered through celite. The filtrate was separated and the aqueous layer was extracted again with diethyl ether (110 ml). The organic layers were combined and washed with saturated brine (110 ml), dried over anhydrous magnesium sulfate, and concentrated under reduced pressure to give 2-chloro-4-trifluoromethyltoluene (23.0 g) as a brown oil.

$^1$H-NMR(CDCl$_3$): 2.43(3H, s), 7.34(1H, d, J=8 Hz), 7.42(1H, d, J=8 Hz), 7.60(1H, s).

PREPARATION EXAMPLE 4-2

In the same manner as in the aforementioned Preparation Example 2,2-chloro-4-(trifluoromethyl)benzyl bromide (6.20 g) was obtained as a pale-yellow oil from 2-chloro-4-trifluoromethyltoluene (10.0 g).

$^1$H-NMR(CDCl$_3$): 4.59(2H, s), 7.52(1H, d, J=8 Hz), 7.57(1H, d, J=8 Hz), 7.67(1H, s).

PREPARATION EXAMPLE 5-1

3-Chloro-4-methylphenol (2.00 g) was dissolved in N,N-dimethylformamide (10.0 ml), and potassium carbonate (2.91 g) and 1-propyl iodide (2.62 g) were added. The mixture was stirred at room temperature for 20 hr, and the reaction mixture was concentrated under reduced pressure. Water was added, and the mixture was extracted with AcOEt. The organic layer was washed successively with water and saturated brine, dried over anhydrous magnesium sulfate and concentrated under reduced pressure. The residue was applied to silica gel column chromatography and eluted with hexane:ethyl acetate=5:1. The objective fraction was concentrated under reduced pressure to give 2-chloro-4-(1-propoxy)toluene (2.18 g) as a colorless oil.

$^1$H-NMR(CDCl$_3$): 1.02(3H, t, J=7 Hz), 1.72–1.85(2H, m), 2.29(3H, s), 3.88(2H, t, J=7 Hz), 6.71(1H, dd, J=8, 2 Hz), 6.90(1H, d, J=2 Hz), 7.09(1H, d, J=8 Hz).

PREPARATION EXAMPLE 5-2

In the same manner as in the aforementioned Preparation example 2,2-chloro-4-(1-propoxy)benzyl bromide (2.26 g) was obtained as a pale-yellow oil from 2-chloro-4-(1-propoxy)toluene (2.14 g).

$^1$H-NMR(CDCl$_3$): 1.03(3H, t, J=7 Hz), 1.75–1.87(2H, m), 3.90(2H, t, J=7 Hz), 4.59(2H, s), 6.78(1H, dd, J=8, 2 Hz), 6.93(1H, d, J=2 Hz), 7.32(1H, d, J=8 Hz).

PREPARATION EXAMPLE 6-1

In the same manner as in the aforementioned Preparation Example 5–1,2-chloro-4-(1-pentyloxy)toluene (16.3 g) was obtained as a pale-brown oil from 2-chloro-4-methylphenol (10.0 g).

$^1$H-NMR(CDCl$_3$): 0.93(3H, t, J=6 Hz), 1.40(4H, m), 1.76(2H, m), 2.29(2H, s), 3.90(2H, t, J=6 Hz), 6.70(1H, dd, J=8, 2 Hz), 6.90(1H, d, J=2 Hz), 7.10(1H, d, J=8 Hz).

PREPARATION EXAMPLE 6-2

In the same manner as in the aforementioned Preparation Example 2,2-chloro-4-(1-pentyloxy)benzyl bromide (21.9 g) was obtained as a pale-yellow solid from 2-chloro-4-(1-pentyloxy)toluene (16.2 g).

$^1$H-NMR(CDCl$_3$): 0.93(3H, t, J=6 Hz), 1.40(4H, m), 1.76(2H, m), 3.93(2H, t, J=6 Hz), 4.58(2H, s), 6.77(1H, dd, J=8, 2 Hz), 6.92(1H, d, J=2 Hz), 7.32(1H, d, J=8 Hz).

PREPARATION EXAMPLE 7-1

To a solution of 3-chloro-4-methylphenol (1.00 g) in N,N-dimethylformamide (8 ml) was added potassium carbonate powder (1.44 g) and the mixture was heated to 80° C. Thereto was added cyclopentylmethyl methanesulfonate (1.57 g) and the mixture was stirred at 120° C. for 3 hr. The reaction mixture was cooled to room temperature. Water was added and the mixture was extracted 3 times with hexane. The organic layers were combined and washed successively with 1N aqueous sodium hydroxide solution, water and saturated brine and dried over anhydrous magnesium sulfate. The solvent was evaporated and the residue was purified by column chromatography (silica gel, hexane) to give 2-chloro-4-((cyclopentyl)methyloxy)toluene (1.46 g) as a colorless oil.

$^1$H-NMR(CDCl$_3$): 1.22–1.93(8H, m), 2.29(3H, s), 2.34 (1H, sept, J=7 Hz), 3.78(2H, d, J=7 Hz), 6.71(1H, dd, J=8 and 2 Hz), 6.91(1H, d, J=2 Hz), 7.09(1H, d, J=8 Hz).

PREPARATION EXAMPLE 7-2

In the same manner as in the aforementioned Preparation Example 2,2-chloro-4-((cyclopentyl)methyloxy)benzyl bromide (2.06 g) was obtained as an oil from 2-chloro-4-((cyclopentyl)methyloxy)toluene (1.45 g).

$^1$H-NMR(CDCl$_3$): 1.23–1.92(8H, m), 2.34(1H, sept, J=7 Hz), 3.81(2H, d, J=7 Hz), 4.59(2H, s), 6.78(1H, dd, J=9 and 2 Hz), 6.93(1H, d, J=2 Hz), 7.32(1H, d, J=9 Hz).

PREPARATION EXAMPLE 8-1

In the same manner as in the aforementioned Preparation Example 5-1,2-chloro-4-((cyclohexyl)methyloxy)toluene (1.41 g) was obtained as colorless crystals from 3-chloro-4-methylphenol (926 mg).

$^1$H-NMR(CDCl$_3$): 0.95–1.40 (5H), 1.64–1.90(6H), 2.29 (3H, s), 3.70(2H, d, J=6 Hz), 6.70(1H, dd, J=8, 2 Hz), 6.89(1H, d, J=2 Hz), 7.08(1H, d, J=8 Hz).

PREPARATION EXAMPLE 8-2

In the same manner as in the aforementioned Preparation Example 2,2-chloro-4-((cyclohexyl)methyloxy)benzyl bromide (1.35 g) was obtained as a pale-yellow solid from 2-chloro-425 ((cyclohexyl)methyloxy)toluene (1.00 g).

$^1$H-NMR(CDCl$_3$): 0.94–1.40(5H), 1.63–1.94(6H), 3.73 (2H, d, J=6 Hz), 4.59(2H, s), 6.79(1H, dd, J=8, 2 Hz), 6.93(1H, d, J=2 Hz), 7.32(1H, d, J=8 Hz).

PREPARATION EXAMPLE 9

To a solution of 4-bromo-2-chlorobenzyl alcohol (3.56 g) and anhydrous triethylamine (3 ml) in anhydrous dichloromethane (36 ml) was added dropwise methanesulfonyl chloride (1.4 ml) under ice-cooling in a nitrogen atmosphere. The mixture was stirred for 1 hr, and the reaction mixture was washed with water, saturated aqueous sodium hydrogencarbonate solution and saturated brine, and dried over anhydrous magnesium sulfate. The filtrate was concentrated to give 4-bromo-2-chloro-1-((methanesulfonyloxy)methyl)benzene as a pale-brown solid (4.77 g).

$^1$H-NMR(CDCl$_3$): 3.03(3H, s), 5.29(2H, s), 7.37(1H, d, J=8 Hz), 7.47(1H, dd, J=8, 1 Hz), 7.60(1H, d, J=1 Hz). Mass(ESI): m/z 298(M−1).

PREPARATION EXAMPLE 10-1

To a solution of methyl 4-bromo-2-chlorobenzoate (1.25 g) in N,N-dimethylformamide (10 ml) was added sodium thiomethoxide (459 mg) under ice-cooling and the mixture was stirred for 2 hr. To the reaction mixture was added 1N hydrochloric acid and the resulting product was extracted 3 times with diethyl ether. The organic layers were combined, washed successively with water and saturated brine and dried over anhydrous magnesium sulfate. The solvent was evaporated and the residue was applied to silica gel column chromatography (hexane/ethyl acetate=10/1) to give methyl 2-chloro-4-(methylthio)benzoate (835 mg) as a colorless oil.

$^1$H-NMR(CDCl$_3$): 2.49(3H, s), 3.90(3H, s), 7.11(1H, d, J=8 Hz), 7.23(1H, s), 7.78(1H, d, J=8 Hz).

PREPARATION EXAMPLE 10-2

To a suspension of lithium aluminum hydride (139 mg) in tetrahydrofuran (8 ml) was added dropwise methyl 2-chloro-4-(methylthio)benzoate (806 mg) under ice-cooling, and the mixture was stirred for 1 hr. The reaction mixture was diluted with diethyl ether and 1N hydrochloric acid (10 ml) was added dropwise. The resulting product was extracted 3 times with diethyl ether. The organic layers were combined and washed successively with saturated aqueous sodium hydrogencarbonate solution and saturated brine, and dried over anhydrous magnesium sulfate. The solvent was evaporated to give 2-chloro-4-(methylthio)benzyl alcohol (725 mg) as a colorless oil.

$^1$H-NMR(CDCl$_3$): 1.92(1H, br t, J=7 Hz), 2.48(3H, s), 4.73(2H, d, J=7 Hz), 7.15(1H, d, J=8 Hz), 7.23(1H, s), 7.37(1H, d, J=8 Hz).

PREPARATION EXAMPLE 10-3

In the same manner as in the aforementioned Preparation Example 9,2-chloro-1-((methanesulfonyloxy)methyl)-4-(methylthio)benzene (1.02 g) was obtained as a colorless oil from 2-chloro-4-(methylthio)benzyl alcohol (687 mg).

$^1$H-NMR(CDCl$_3$): 2.48(3H, s), 3.00(3H, s), 5.30(2H, s), 7.15(1H, dd, J=8 and 2 Hz), 7.26(1H, d, J=2 Hz), 7.38(1H, d, J=8 Hz).

PREPARATION EXAMPLE 11

In the same manner as in the aforementioned Preparation Example 9,2-chloro-1-((methanesulfonyloxy)methyl)-4-nitrobenzene (3.56 g) was obtained as brown crystals from 2-chloro-440 nitrobenzyl alcohol (2.5 g).

$^1$H-NMR(CDCl$_3$): 3.12(3H, s), 5.40(2H, s), 7.73(1H, d, J=8 Hz), 8.18(1H, dd, J=2, 8 Hz), 8.79(1H, d, J=2 Hz).

PREPARATION EXAMPLE 12-1

4-amino-2-chlorobenzoic acid (10.01 g) was homogeneously dissolved in 12.5% sulfuric acid (400 ml) by heating to 70° C. and ice-cooled. To this suspension was added dropwise aqueous sodium nitrite solution (4.24 g/12 ml of water) at not more than 8° C. over 5 min. After 5 min, this solution was gradually poured into water (500 ml) at 80° C., upon which the solution foamed vigorously and turned into a red solution. The reaction mixture was stirred at 80° C. for 1 hr. After allowing to cool, the resulting product was extracted 3 times with diethyl ether. The organic layers were combined and washed successively with dil. hydrochloric acid, water and saturated brine, and dried over anhydrous magnesium sulfate. The solvent was evaporated and a small amount of diisopropyl ether was added to the residue to allow for crystallization to give 2-chloro-4-hydroxybenzoic acid (6.32 g) as an orange powder.

$^1$H-NMR(DMSO-d$_6$): 6.79(1H, dd, J=8 and 2 Hz), 6.88 (1H, d, J=2 Hz), 7.77(1H, d, J=8 Hz). Mass(ESI): m/e 171(M−H)−.

PREPARATION EXAMPLE 12-2

To a solution of 2-chloro-4-hydroxybenzoic acid (695 mg) in N,N-dimethylformamide (3.5 ml) were added potassium carbonate (1.67 g) and benzyl bromide (1.73 g) and the mixture was stirred at room temperature for 14 hr. To the reaction mixture was added 1N hydrochloric acid and the resulting product was extracted 3 times with diethyl ether. The organic layers were combined and washed successively with water, saturated aqueous sodium hydrogencarbonate solution and saturated brine, and dried over anhydrous magnesium sulfate. The solvent was evaporated and the residue was recrystallized from diisopropyl ether/hexane to give benzyl 4-benzyloxy-2-chlorobenzoate (1.13 g) as a pale-yellow powder.

$^1$H-NMR(CDCl$_3$): 5.09(2H, s), 5.32(2H, s), 6.87(1H, dd, J=8 and 2 Hz), 7.05(1H, d, J=2 Hz), 7.29–7.50(10H, m), 7.91(1H, d, J=8 Hz). Mass(ESI): m/e 353(M+H)+.

PREPARATION EXAMPLE 12-3

To benzyl 4-benzyloxy-2-chlorobenzoate (1.12 g) were added ethanol (8.8 ml), 1,4-dioxane (2.2 ml) and 1N aqueous sodium hydroxide solution (4.7 ml) and the mixture was stirred at 70° C. for 1.5 hr. The solvent was evaporated and water was added to the residue for dissolution, which was washed with diethyl ether. The aqueous layer was acidified with 1N hydrochloric acid and the precipitate was collected by filtration to give 4-benzyloxy-2-chlorobenzoic acid (810 mg) as a pale-yellow powder.

$^1$H-NMR(DMSO-$d_6$): 5.20(2H, s), 7.06(1H, dd, J=8 and 2 Hz), 7.18(1H, d, J=2 Hz), 7.29–7.50(5H, m), 7.82(1H, d, J=8 Hz). Mass(ESI): m/e 261(M–H)–.

PREPARATION EXAMPLE 12-4

To a solution of 4-benzyloxy-2-chlorobenzoic acid (788 mg) in tetrahydrofuran (7.9 ml) was added dropwise borane-dimethylsulfide complex (10.0M, 0.6 ml) at room temperature under a nitrogen atmosphere and the mixture was refluxed under heating for 2.5 hr. The reaction mixture was allowed to cool to room temperature, and 1N hydrochloric acid (1.5 ml) was carefully added dropwise. The mixture was stirred for 30 min. To the reaction mixture was added water and the resulting product was extracted 3 times with ethyl acetate. The organic layers were combined, washed successively with saturated aqueous sodium hydrogencarbonate solution and saturated brine, and dried over anhydrous magnesium sulfate. The solvent was evaporated to give 4-benzyloxy-2-chlorobenzyl alcohol (778 mg) as a white powder.

$^1$H-NMR(CDCl$_3$): 1.83(1H, br t, J=7 Hz), 4.70(2H, d, J=7 Hz), 5.05(2H, s), 6.88(1H, dd, J=8 and 2 Hz), 7.01(1H, d, J=2 Hz), 7.28–7.46(6H, m).

PREPARATION EXAMPLE 12-5

In the same manner as in the aforementioned Preparation Example 9,4-benzyloxy-2-chlorobenzyl chloride (639 mg) was obtained as a colorless oil from 4-benzyloxy-2-chlorobenzyl alcohol (523 mg).

$^1$H-NMR(CDCl$_3$): 4.67(2H, s), 5.05(2H, s), 6.87(1H, dd, J=8 and 2 Hz), 7.02(1H, d, J=2 Hz), 7.28–7.44(6H, m).

PREPARATION EXAMPLE 13-1

To a solution of 4-bromo-2-chlorobenzyl alcohol (14.48 g) in N,N-dimethylformamide (72 ml) were added imidazole (5.34 g) and tert-butylchlorodiphenylsilane (19.8 g) under ice-cooling, and the mixture was stirred for 1 hr. Water was added to the reaction mixture and the resulting product was extracted twice with hexane. The organic layers were combined, washed successively with water, saturated aqueous sodium hydrogencarbonate solution and saturated brine, and dried over anhydrous magnesium sulfate. The solvent was evaporated and the residue was applied to silica gel column chromatography (hexane) to give 4-bromo-1-((tert-butyldiphenylsiloxy)methyl)-2-chlorobenzene (29.22 g) as a colorless oil.

$^1$H-NMR(CDCl$_3$): 1.10(9H, s), 4.75(2H, s), 7.32–7.50 (8H, m), 7.55–7.72(5H, m).

PREPARATION EXAMPLE 13-2

To a solution of 4-bromo-1-((tert-butyldiphenylsiloxy) methyl)-2-chlorobenzene (8.65 g) in tetrahydrofuran (22 ml) was added 1-butyl lithium/hexane solution (1.54M, 13.5 ml) at –75° C. in a nitrogen atmosphere, and the mixture was stirred for 15 min. The reaction mixture was once heated to 10° C. and again cooled to –75° C. and 1-formyl piperidine (2.55 g) was added dropwise over 10 min. The reaction mixture was heated to room temperature over 3 hr. To the reaction mixture was added aqueous ammonium chloride solution and the resulting product was extracted twice with hexane. The organic layers were combined, washed successively with dil. hydrochloric acid, saturated aqueous sodium hydrogencarbonate solution and saturated brine, and dried over anhydrous magnesium sulfate. The solvent was evaporated and the residue was applied to silica gel column chromatography (hexane/ethyl acetate=40/1) to give 4-((tert-butyldiphenylsiloxy)methyl)-3-chlorobenzaldehyde (3.26 g) as a pale-yellow oil.

$^1$H-NMR(CDCl$_3$): 1.14(9H, s), 4.87(2H, s), 7.33–7.51 (6H, m), 7.63–7.75(4H, m), 7.81(1H, d, J=2 Hz), 7.84(1H, dd, J=8 and 2 Hz), 7.97(1H, d, J=8 Hz), 9.97(1H, s).

PREPARATION EXAMPLE 13-3

To a suspension of 4-((tert-butyldiphenylsiloxy)methyl)-3-chlorobenzaldehyde (3.24 g) in ethanol (32 ml) was added sodium borohydride (149 mg) under ice-cooling and the mixture was stirred at room temperature for 3 hr. The reaction mixture was concentrated to about half amount. Water was added and the resulting product was extracted twice with diisopropyl ether. The organic layers were combined, washed successively with saturated aqueous sodium hydrogencarbonate solution and saturated brine, and dried over anhydrous magnesium sulfate. The solvent was evaporated and the residue was purified by silica gel column chromatography (hexane/ethyl acetate=5/1) to give 4-((tert-butyldiphenylsiloxy)methyl)- 3-chlorobenzyl alcohol (3.08 g) as a colorless oil.

$^1$H-NMR(CDCl$_3$): 1.12(9H, s), 1.70(1H, br t, J=5 Hz), 4.69(2H, d, J=5 Hz), 4.83(2H, s), 7.27–7.50(8H, m), 7.65–7.78(5H, m).

PREPARATION EXAMPLE 13-4

In the same manner as in the aforementioned Preparation Example 9,1-((tert-butyldiphenylsiloxy)methyl)-2-chloro-4-((methanesulfonyloxy)methyl)benzene (3.80 g) was obtained as a colorless oil from 4-((tert-butyldiphenylsiloxy) methyl)-3-chlorobenzyl alcohol (3.05 g).

$^1$H-NMR(CDCl$_3$): 1.12(9H, s), 2.97(3H, s), 4.83(2H, s), 5.21(2H, s), 7.33–7.50(8H, m), 7.63–7.75(4H, m), 7.77–7.83(1H, m).

PREPARATION EXAMPLE 13-5

To a solution of phenol (969 mg) in N,N-dimethylformamide (27 ml) was added potassium carbonate powder (1.92 g) and the mixture was stirred at room temperature for 5 min. 1-((tert-Butyldiphenylsiloxy)methyl)-2-chloro-4-((methanesulfonyloxy) methyl)benzene (3.39 g) was added and the mixture was stirred at 100° C. for 3 hr. The reaction mixture was allowed to cool to room temperature. Water was added and the mixture was extracted twice with hexane. The organic layers were combined, washed successively with water and saturated brine, and dried over anhydrous magnesium sulfate. The solvent was evaporated and the residue was purified by column chromatography (silica gel, hexane/ ethyl acetate=50/1) to give 1-((tert-butyldiphenylsiloxy)-methyl)-2-chloro-4-(phenoxymethyl)benzene (2.65 g) as a colorless oil.

¹H-NMR(CDCl₃): 1.12(9H, s), 4.83(2H, s), 5.04(2H, s), 6.93–7.04(3H, m), 7.25–7.50(10H, m), 7.65–7.73(4H, m), 7.73–7.80(1H, m).

PREPARATION EXAMPLE 13-6

To a solution of 1-((tert-butyldiphenylsiloxy)methyl)-2-chloro-4-(phenoxymethyl)benzene (2.84 g) in tetrahydrofuran (14 ml) was added tetrabutyl ammonium fluoride/tetrahydrofuran solution (1.0 M, 7.0 ml) under ice-cooling and the mixture was stirred for 1.5 hr. Water was added to the reaction mixture and the resulting product was extracted twice with ethyl acetate. The organic layers were combined, washed successively with 1N hydrochloric acid, saturated aqueous sodium hydrogencarbonate solution and saturated brine, and dried over anhydrous magnesium sulfate. The solvent was evaporated and the residue was purified by silica gel column chromatography (hexane/ethyl acetate=5/1) to give 2-chloro-4-(phenoxymethyl)benzyl alcohol (1.38 g) as a white powder.
¹H-NMR(CDCl₃): 1.92(1H, br t, J=6 Hz), 4.79(2H, d, J=6 Hz), 5.05(2H, s), 6.88–7.06(3H, m), 7.23–7.40(3H, m), 7.42–7.57(2H, m).

PREPARATION EXAMPLE 13-7

In the same manner as in the aforementioned Preparation Example 9,2-chloro-1-((methanesulfonyloxy)methyl)-4-(phenoxymethyl)benzene (1.83 g) was obtained as an oil from 2-chloro-4-(phenoxymethyl)benzyl alcohol (1.36 g).
¹H-NMR(CDCl₃): 3.03(3H, s), 5.07(2H, s), 5.35(2H, s), 6.91–7.04(3H, m), 7.25–7.42(3H, m), 7.44–7.67(2H, m).

PREPARATION EXAMPLE 14-1

In the same manner as in the aforementioned Preparation Example 12-4,3-chloro-4-methylbenzyl alcohol (23.0 g) was obtained as a colorless oil from 3-chloro-4-methylbenzoic acid (25.0 g).
¹H-NMR(CDCl₃):2.36(3H, s), 4.65(2H, s), 7.14(1H, d, J=8 Hz), 7.23(1H, d, J=8 Hz), 7.36(1H, s).

PREPARATION EXAMPLE 14-2

To a solution of 3-chloro-4-methylbenzyl alcohol (2.00 g) and triethylamine (8.9 ml) in dimethyl sulfoxide (10 ml) was added sulfur trioxide-pyridine complex (4.47 g) under water-cooling. The mixture was stirred at room temperature for 3 hr. The reaction mixture was poured into ice water and the mixture was extracted with diethyl ether. The organic layer was washed with 1N hydrochloric acid, saturated brine and saturated aqueous sodium hydrogencarbonate solution and dried over magnesium sulfate. The residue was concentrated to dryness under reduced pressure to give 3-chloro-4-methylbenzaldehyde (1.40 g) as a pale-yellow oil.
¹H-NMR(CDCl₃):2.46(3H, s), 4.65(2H, s), 7.40(1H, d, J=8 Hz), 7.68(1H, d, J=8 Hz), 9.92(1H, s).

PREPARATION EXAMPLE 14-3

In the same manner as in Preparation Example 15-2 to be mentioned later, (E)-2-chloro-4-(2-phenylethenyl)toluene (1.55 g) was obtained as a white powder from 3-chloro-4-methylbenzaldehyde (1.40 g) and diethyl benzylphosphonate (2.27 g).
¹H-NMR(CDCl₃):2.38(3H, s), 7.00(1H, d, J=16 Hz), 7.08(1H, d, J=1 6 Hz), 7.18–7.53(8H).

PREPARATION EXAMPLE 14-4

In the same manner as in the aforementioned Preparation Example 2, (E)-2-chloro-4-(2-phenylethenyl)benzyl bromide (309 mg) was obtained as a white powder from (E)-2-chloro-4-(2-phenylethenyl)toluene (1.35 g).
¹H-NMR(CDCl₃):4.61(2H, s), 7.01(1H, d, J=16 Hz), 7.14 (1H, d, J=16 Hz), 7.24–7.57(8H).

PREPARATION EXAMPLE 15-1

To a solution of 5-chloro-2-methylimidazole-4-carbaldehyde (433 mg) in N,N-dimethylformamide (4.3 ml) were added potassium carbonate powder (616 mg) and 2-chloro-4-iodobenzyl bromide (1.2 equivalents) under ice-cooling and the mixture was stirred at room temperature for 2.5 hr. To the reaction mixture were added water and saturated brine, and the resulting product was extracted twice with ethyl acetate. The organic layers were combined, washed with saturated brine, and dried over anhydrous magnesium sulfate. The solvent was evaporated and the residue was purified by silica gel column chromatography (hexane/ethyl acetate=5/1) to give 4-chloro-1-(2-chloro-4-iodobenzyl)-2-methylimidazole-5-carbaldehyde (1.01 g) as a white powder.
¹H-NMR(CDCl₃): 2.33(3H, s), 5.56(2H, s), 6.21(1H, d, J=8 Hz), 7.50(1H, dd, J=8 and 2 Hz), 7.78(1H, d, J=2 Hz), 9.75(1H, s). Mass(ESI): m/e 395(M+H)+.

PREPARATION EXAMPLE 15-2

To a solution of 4-chloro-1-(2-chloro-4-iodobenzyl)-2-methylimidazole 5-carbaldehyde (1.01 g) in tetrahydrofuran (10 ml) was added methyl (triphenylphosphoranylidene) acetate (1.27 g) and the mixture was refluxed under heating for 4 hr. The solvent was evaporated and the residue was purified by silica gel column chromatography (hexane/ethyl acetate=3/1) to give methyl (E)-3-(4-chloro-1-(2-chloro-4-iodobenzyl)-2-methylimidazol-5-yl)-2-propenate (974 mg) as a white powder.
¹H-NMR(CDCl₃): 2.33(3H, s), 3.75(3H, s), 5.15(2H, s), 6.17(1H, d, J=8 Hz), 6.49(1H, d, J=16 Hz), 7.28(1H, d, J=16 Hz), 7.53(1H, dd, J=8 and 2 Hz), 7.81(1H, d, J=2 Hz). Mass(ESI): m/e 451(M+H)+.

PREPARATION EXAMPLE 15-3

A mixture of tetrakis(triphenylphosphine)palladium(0) (89 mg), methyl (E)-3-(4-chloro-1-(2-chloro-4-iodobenzyl)-2-methylimidazol-5-yl)-2-propenate (350 mg), 2-furylboronic acid (135 mg), potassium carbonate powder (321 mg) and N,N-dimethylformamide (3.5 ml) was stirred under a nitrogen atmosphere at 80° C. for 4 hr. The reaction mixture was allowed to cool to room temperature and water was added. The precipitate was collected by filtration. The precipitate was dissolved in chloroform, washed successively with saturated aqueous sodium hydrogencarbonate solution and saturated brine, and dried over magnesium sulfate. The solvent was evaporated and the residue was purified by silica gel column chromatography (chloroform/ethyl acetate=10/1) to give methyl (E)-3-(4-chloro-1-(2-chloro-4-(2-furyl) benzyl)-2-methylimidazol-5-yl)-2-propenate (336 mg) as a pale-yellow powder.
¹H-NMR(CDCl₃): 2.36(3H, s), 3.74(3H, s), 5.22(2H, s), 6.44–6.50(2H, m), 6.50(1H, d, J=16 Hz), 6.68(1H, d, J=3 Hz), 7.34(1H, d, J=16 Hz), 7.43–7.50(2H, m), 7.76(1H, d, J=2 Hz). Mass(ESI): m/e 391(M+H)+.

PREPARATION EXAMPLE 15-4

To a suspension of methyl (E)-3-(4-chloro-1-(2-chloro-4-(2-furyl)benzyl)-2-methylimidazol-5-yl)-2-propenate (319 mg) in 1,4-dioxane (1.6 ml) was added 1N aqueous sodium hydroxide solution (1.2 ml) and the mixture was stirred at 50° C. for 1 hr. The reaction mixture was ice-cooled and 1N hydrochloric acid (1.2 ml) was added dropwise to neutralize the mixture. The resulting product was extracted 3 times with chloroform-methanol (4/1). The organic layers were combined, washed with saturated brine, and dried over magnesium sulfate. The solvent was evaporated to give (E)-3-(4-chloro-1-(2-chloro-4-(2-furyl)benzyl)-2-methylimidazol-5-yl)-2-propenic acid (310 mg) as a gray white powder.

$^1$H-NMR(DMSO-d$_6$): 2.34(3H, s), 5.41(2H, s), 6.26(1H, d, J=16 Hz), 6.58(1H, d, J=8 Hz), 6.62(1H, dd, J=3 and 2 Hz), 7.09(1H, d, J=3 Hz), 7.22(1H, d, J=16 Hz), 7.62(1H, dd, J=8 and 2 Hz), 7.79(1H, d, J=2 Hz), 7.88(1H, d, J=2 Hz). Mass(ESI): m/e 375(M−H)−.

PREPARATION EXAMPLE 16-1

In the same manner as in the aforementioned Preparation Example 15-3, methyl (E)-3-(4-chloro-1-(2-chloro-4-(2-thienyl)benzyl)-2-methylimidazol-5-yl)-2-propenate was obtained as a yellow oil (331 mg) from methyl (E)-3-(4-chloro-1-(2-chloro-4-iodobenzyl)-2-methylimidazol-5-yl)-2-propenate (360 mg).

$^1$H-NMR(CDCl$_3$): 2.36(3H, s), 3.74(3H, s), 5.23(2H, s), 6.47(1H, d, J=8 Hz), 6.51(1H, d, J=16 Hz), 7.07–7.11(1H, m), 7.29–7.38(3H, m), 7.41(1H, dd, J=2, 8 Hz), 7.69(1H, d, J=2 Hz). Mass(ESI): m/z 407(M+1).

PREPARATION EXAMPLE 16-2

In the same manner as in the aforementioned Preparation Example 15-4, (E)-3-(4-chloro-1-(2-chloro-4-(2-thienyl)benzyl)-2-methylimidazol-5-yl)-2-propenic acid was obtained as pale-yellow crystals (231 mg) from methyl (E)-3-(4-chloro-1-(2-chloro-4-(2-thienyl)benzyl)-2-methylimidazol-5-yl)-2-propenate (281 mg).

$^1$H-NMR(DMSO-d$_6$): 2.34(3H, s), 5.42(2H, s), 6.27(1H, d, J=16 Hz), 6.55(1H, d, J=8 Hz), 7.12–7.19(1H, m), 7.25(1H, d, J=16 Hz), 7.52–7.62(3H, m), 7.87(1H, d, J=2 Hz). Mass(ESI): m/z 391(M−1).

PREPARATION EXAMPLE 17-1

To a mixture of methyl (E)-3-(4-chloro-1-(2-chloro-4-iodobenzyl)-2-methylimidazol-5-yl)-2-propenate (360 mg), dichlorobis(triphenylphosphine)palladium(II) (28 mg) and copper iodide (7.6 mg) was added a solution of phenylacetylene (326 mg) in diisopropylamine (20 ml) in a nitrogen atmosphere and the mixture was refluxed under heating for 5 hr. The reaction mixture was allowed to cool. Water was added and the mixture was extracted twice with chloroform. The organic layers were combined, washed with saturated aqueous sodium hydrogencarbonate solution and saturated brine, and dried over anhydrous magnesium sulfate. The resultant was filtrated under reduced pressure and concentrated to give a crude product. The product was applied to flash silica gel column chromatography (silica gel 10 g) to give methyl (E)-3-(4-chloro-1-(2-chloro-4-(phenylethynyl)benzyl)-2-methylimidazol-5-yl)-2-propenate as brown amorphous (331 mg) from the eluted fraction of hexane/ethyl acetate=5/1–1-1.

$^1$H-NMR(CDCl$_3$): 2.35(3H, s), 3.75(3H, s), 5.23(2H, s), 6.45(1H, d, J=8 Hz), 6.50(1H, d, J=16 Hz), 7.27–7.40(5H, m), 7.48–7.56(2H, m), 7.63(1H, s). Mass(ESI): m/z 425(M+1).

PREPARATION EXAMPLE 17-2

In the same manner as in the aforementioned Preparation Example 15-4, (E)-3-(4-chloro-1-(2-chloro-4-(phenylethynyl)-benzyl)-2-methylimidazol-5-yl)-2-propenic acid was obtained as pale-ocher crystals (283 mg) from methyl (E)-3-(4-chloro-1-(2-chloro-4-(phenylethynyl)benzyl)-2-methylimidazol-5-yl)-2-propenate (413 mg).

$^1$H-NMR(CDCl$_3$): 2.36(3H, s), 5.23(2H, s), 6.45(1H, d, J=8 Hz), 6.48(1H, d, J-16 Hz), 7.32–7.41(5H, m), 7.48–7.55(2H, m), 7.64(1H, d, J=2 Hz). Mass(ESI): m/z 409(M−1).

PREPARATION EXAMPLE 18-1

In the same manner as in the aforementioned Preparation Example 15-1, 1-(4-bromo-2-chlorobenzyl)-4-chloro-2-methylimidazole-5-carbaldehyde (430 mg) was obtained as pale-yellow crystals from 4-chloro-2-methylimidazole-5-carbaldehyde (200 mg) and 4-bromo-2-chloro-1-((methanesulfonyloxy)methyl)benzene (456 mg).

$^1$H-NMR(CDCl$_3$): 2.33(3H, s), 5.56(2H, s), 6.38(1H, d, J=8 Hz), 7.31(1H, dd, J=8, 2 Hz), 7.60(1H, d, J=2 Hz), 9.75(1H, s).

PREPARATION EXAMPLE 18-2

In the same manner as in the aforementioned Preparation Example 15-2, methyl (E)-3-(1-(4-bromo-2-chlorobenzyl)-4-chloro-2-methylimidazol-5-yl)-2-propenate (372 mg) was obtained as colorless crystals from 1-(4-bromo-2-chlorobenzyl)-4-chloro-2-methylimidazole 5-carbaldehyde (394 mg) and methyl (triphenylphosphoranylidene)acetate (606 mg).

$^1$H-NMR(CDCl$_3$): 2.33(3H, s), 3.75(3H, s), 5.16(2H, s), 6.33(1H, d, J=8 Hz), 6.50(1H, d, J=15 Hz), 7.26(1H, d, J=2 Hz), 7.34(1H, dd, J=8, 2 Hz), 7.63(1H, d, J=2 Hz).

PREPARATION EXAMPLE 18-3

In the same manner as in the aforementioned Preparation Example 15-4, (E)-3-(1-(4-bromo-2-chlorobenzyl)-4-chloro-2-methylimidazol-5-yl)-2-propenic acid (338 mg) was obtained as pale-yellow crystals from methyl (E)-3-(1-(4-bromo-2-chlorobenzyl)-4-chloro-2-methylimidazol-5-yl)-2-propenate (355 mg).

$^1$H-NMR(DMSO-d$_6$): 2.31(3H, s), 5.38(2H, s), 6.26(1H, d, J=15 Hz), 6.45(1H, d, J=8 Hz), 7.21(1H, d, J=15 Hz), 7.53(1H, dd, J=8, 2 Hz), 7.87(1H, d, J=2 Hz).

PREPARATION EXAMPLE 19-1

In the same manner as in the aforementioned Preparation Example 15-1, 4-chloro-1-(2-chloro-4-phenylbenzyl)-2-methylimidazole-5-carbaldehyde (1.23 g) was obtained as a colorless oil from 5-chloro-2-methylimidazole-4-carbaldehyde (600 mg) and 2-chloro-4-phenylbenzyl bromide (1.4 g).

$^1$H-NMR(CDCl$_3$): 2.36(3H, s), 5.67(2H, s), 6.56(1H, d, J=8 Hz), 7.35– 7.55(6H), 7.65(1H, s), 9.80(1H, s).

PREPARATION EXAMPLE 19-2

In the same manner as in the aforementioned Preparation Example 15-2, methyl (E)-3-[4-chloro-1-(2-chloro-4-phenylbenzyl)-2-methylimidazol-5-yl]-2-propenate (1.13 g) was obtained as a white powder from 4-chloro-1-(2-chloro-4-phenylbenzyl)-2-methylimidazole-5-carbaldehyde (1.23 g).

$^1$H-NMR(CDCl$_3$): 2.37(3H, s), 3.74(3H, s), 5.25(2H, s), 6.46–6.57(2H), 7.30–7.55(7H), 7.68(1H, s).

PREPARATION EXAMPLE 19-3

In the same manner as in the aforementioned Preparation Example 15-4, (E)-3-[4-chloro-1-(2-chloro-4-phenylbenzyl)-2-methylimidazol-5-yl]-2-propenic acid (1.18 g) was obtained as a white powder from methyl (E)-3-[4-chloro-1-(2-chloro-4-phenylbenzyl)-2-methylimidazol-5-yl]-2-propenate (1.35 g).

$^1$H-NMR(DMSO-d$_6$): 2.35(3H, s), 5.45(2H,s), 6.30(1H, d, J=16 Hz), 6.58(1H, d, J=8 Hz), 7.25(1H, d, J=16 Hz), 7.36–7.52(3H), 7.62(1H, d, J=8 Hz), 7.69(2H, d, J=8 Hz), 7.86(1H, s).

PREPARATION EXAMPLE 20-1

In the same manner as in the aforementioned Preparation Example 15-1,4-chloro-1-(2-chloro-4-(1-propoxy)benzyl)-2-methylimidazole-5-carbaldehyde (376 mg) was obtained as pale-yellow crystals from 4-chloro-2-methylimidazole-5-carbaldehyde (200 mg) and 2-chloro-4-(1-propoxy)benzyl bromide (474 mg).

$^1$H-NMR(CDCl$_3$): 1.02(3H, t, J=7 Hz), 1.73–1.85(2H, m), 2.32(3H, s), 3.87(2H, t, J=7 Hz), 5.57(2H, s), 6.46(1H, d, J=8 Hz), 6.70(1H, dd, J=8, 2 Hz), 6.96(1H, d, J=2 Hz), 9.77(1H, s).

PREPARATION EXAMPLE 20-2

In the same manner as in the aforementioned Preparation Example 15-2, methyl (E)-3-(4-chloro-1-(2-chloro-4-(1-propoxy)benzyl)-2-methylimidazol-5-yl)-2-propenate (348 mg) was obtained as colorless crystals from 4-chloro-1-(2-chloro-4-(1-propoxy)benzyl)-2-methylimidazole-5-carbaldehyde (356 mg) and methyl (triphenylphosphoranylidene)acetate (546 mg).

$^1$H-NMR(CDCl$_3$): 1.02(3H, t, J=7 Hz), 1.74–1.85(2H, m), 2.34(3H, s), 3.75(3H, s), 3.89(2H, t, J=7 Hz), 5.15(2H, s), 6.37(1H, d, J=8 Hz), 6.49(1H, d, J=15 Hz), 6.71(1H, dd, J=8, 2 Hz), 6.99(1H, d, J=2 Hz), 7.34(1H, d, J=15 Hz).

PREPARATION EXAMPLE 20-3

In the same manner as in the aforementioned Preparation Example 15-4, (E)-3-(4-chloro-1-(2-chloro-4-(1-propoxy)benzyl)-2-methylimidazol-5-yl)-2-propenic acid (305 mg) was obtained as colorless crystals from methyl (E)-3-(4-chloro-1-(2-chloro-4-(1-propoxy)benzyl)-2-methylimidazol-5-yl)-2-propenate (332 mg).

$^1$H-NMR(DMSO-d$_6$): 0.95(3H, t, J=7 Hz), 1.64–1.75(2H, m), 2.32(3H, s), 3.92(2H, t, J=7 Hz), 5.31(2H, s), 6.25(1H, d, J=15 Hz), 6.44(1H, d, J=8 Hz), 6.88(1H, dd, J=8, 2 Hz), 7.13(1H, d, J=2 Hz), 7.23(1H, d, J=15 Hz).

PREPARATION EXAMPLE 21-1

In the same manner as in the aforementioned Preparation Example 15-1,4-chloro-1-[2-chloro-4-(1-pentyloxy)benzyl]-2-methylimidazole-5-carbaldehyde (460 mg) was obtained as a pale-yellow oil from 5-chloro-2-methylimidazole-4-carbaldehyde (200 mg) and 2-chloro-4-(1-pentyloxy)benzyl bromide (378 mg).

$^1$H-NMR(CDCl$_3$): 0.93(3H, t, J=6 Hz), 1.40(4H, m), 1.76(2H, m), 2.32(3H, s), 3.90(2H, t, J=6 Hz), 5.57(2H, s), 6.45(1H, d, J=8 Hz), 6.70(1H, dd, J=8, 2 Hz), 6.95(1H, d, J=2 Hz), 9.76(1H, s).

PREPARATION EXAMPLE 21-2

In the same manner as in the aforementioned Preparation Example 15-2, methyl (E)-3-(4-chloro-1-(2-chloro-4-(1-pentyloxy)benzyl)-2-methylimidazol-5-yl)-2-propenate was obtained as a milky white solid (427 mg) from 4-chloro-1-(2-chloro-4-(1-pentyloxy)benzyl)-2-methylimidazole-5-carbaldehyde (439 mg).

$^1$H-NMR(CDCl$_3$): 0.93(3H, t, J=7 Hz), 1.32–1.49(4H, m), 1.71–1.83(2H, m), 2.34(3H, s), 3.75(3H, s), 3.92(2H, t, J=7 Hz), 5.15(2H, s), 6.37(1H, d, J=8 Hz), 6.49(1H, d, J=16 Hz), 6.70(1H, dd, J=2, 8 Hz), 6.99(1H, d, J=2 Hz), 7.34(1H, d, J=16 Hz). Mass(ESI): m/z 411(M+1).

PREPARATION EXAMPLE 21-3

In the same manner as in the aforementioned Preparation Example 15-4, (E)-3-(4-chloro-1-(2-chloro-4-(1-pentyloxy)benzyl)-2-methylimidazol-5-yl)-2-propenic acid was obtained as thin yellow crystals (370 mg) from methyl (E)-3-(4-chloro-1-(2-chloro-4-(1-pentyloxy)benzyl)-2-methylimidazol-5-yl)-2-propenate (403 mg).

$^1$H-NMR(CDCl$_3$): 0.92(3H, t, J=7 Hz), 1.30–1.50(4H, m), 1.70–1.83(2H, m), 2.36(3H, s), 3.92(2H, t, J=7 Hz), 5.16(2H, s), 6.38(1H, d, J=8 Hz), 6.47(1H, d, J=16 Hz), 6.71(1H, dd, J=2, 8 Hz), 6.99(1H, d, J=2 Hz), 7.40(1H, d, J=16 Hz). Mass(ESI): m/z 395(M−1).

PREPARATION EXAMPLE 22-1

In the same manner as in the aforementioned Preparation Example 15-1,4-chloro-1-(2-chloro-4-((cyclopentyl)methyloxy)benzyl)-2-methylimidazole-5-carbaldehyde (608 mg) was obtained as a colorless oil from 5-chloro-2-methylimidazole-4-carbaldehyde (300 mg) and 2-chloro-4-((cyclopentyl)methyloxy)benzyl bromide (764 mg).

$^1$H-NMR(CDCl$_3$): 1.22–1.92(8H, m), 2.32(3H, s), 2.33 (1H, sept, J=7 Hz), 3.78(2H, d, J=7 Hz), 5.57(2H, s), 6.45(1H, d, J=8 Hz), 6.70(1H, dd, J=9 and 2 Hz), 6.96(1H, d, J=2 Hz), 9.77(1H, s). Mass(ESI): m/e 367(M+H)+.

PREPARATION EXAMPLE 22-2

In the same manner as in the aforementioned Preparation Example 15-2, methyl (E)-3-(4-chloro-1-(2-chloro-4-((cyclopentyl)methyloxy)benzyl)-2-methylimidazol-5-yl)-2-propenate (563 mg) was obtained as a white powder from 4-chloro-1-(2-chloro-4-((cyclopentyl)methyloxy)benzyl)-2-methylimidazole-5-carbaldehyde (577 mg) and methyl (triphenylphosphoranylidene)acetate (788 mg).

$^1$H-NMR(CDCl$_3$): 1.24–1.92(8H, m), 2.34(3H, s), 2.34 (1H, sept, J=7 Hz), 3.74(3H, s), 3.79(2H, d, J=7 Hz), 5.15(2H, s), 6.37(1H, d, J=8 Hz), 6.49(1H, d, J=16 Hz), 6.71(1H, dd, J=8 and 3 Hz), 6.99(1H, d, J=3 Hz), 7.34(1H, d, J=16 Hz). Mass(ESI): m/e 423(M+H)+.

PREPARATION EXAMPLE 22-3

In the same manner as in the aforementioned Preparation Example 15-4, (E)-3-(4-chloro-1-(2-chloro-4-((cyclopentyl)methyloxy)benzyl)-2-methylimidazol-5-yl)-2-propenic acid (532 mg) was obtained as a white powder from methyl (E)-3-(4-chloro-1-(2-chloro-4-((cyclopentyl)methyloxy)benzyl)-2-methylimidazol-5-yl)-2-propenate (535 mg).

$^1$H-NMR(CDCl$_3$): 1.23–1.92(8H, m), 2.33(1H, sept, J=7 Hz), 2.35(3H, s), 3.79(2H, d, J=7 Hz), 5.15(2H, s), 6.37(1H, d, J=8 Hz), 6.46(1H, d, J=16 Hz), 6.71(1H, dd, J=8 and 2 Hz), 6.99(1H, d, J=2 Hz), 7.40(1H, d, J=16 Hz). Mass(ESI): m/e 407(M−H)−.

PREPARATION EXAMPLE 23-1

In the same manner as in the aforementioned Preparation Example 15-1,4-chloro-1-(2-chloro-4-((cyclohexyl)methyloxy)benzyl)-2-methylimidazole-5-carbaldehyde was obtained as a yellow oil (410 mg) from 5-chloro-2-methylimidazole-4-carbaldehyde (200 mg) and 2-chloro-4-((cyclohexyl)methyloxy)benzyl bromide (659 mg).

$^1$H-NMR(CDCl$_3$): 0.95–1.10(2H, m), 1.15–1.39(4H, m), 1.62–1.89(5H, m), 2.32(3H, s), 3.70(2H, d, J=7 Hz), 5.57 (2H, s), 6.45(1H, d, J=8 Hz), 6.69(1H, dd, J=2, 8 Hz), 6.95(1H, d, J=2 Hz), 9.76(1H, s). Mass(ESI): m/z 381(M+1).

PREPARATION EXAMPLE 23-2

In the same manner as in the aforementioned Preparation Example 15-2, methyl (E)-3-(4-chloro-1-(2-chloro-4-((cyclohexyl)methyloxy)benzyl)-2-methylimidazol-5-yl)-2-propenate was obtained as a yellow oil (419 mg) from 4-chloro-1-(2-chloro-4-((cyclohexyl)methyloxy)benzyl)-2-methylimidazole-5-carbaldehyde (405 mg).

$^1$H-NMR(CDCl$_3$): 0.95–1.11(2H, m), 1.15–1.38(4H, m), 1.63–1.89(5H, m), 2.34(3H, s), 3.71(2H, d, J=7 Hz), 3.74 (3H, s), 5.15(2H, s), 6.36(1H, d, J=8 Hz), 6.49(1H, d, J=16 Hz), 6.70(1H, dd, J=2, 8 Hz), 6.98(1H, d, J=2 Hz), 7.34(1H, d, J=16 Hz). Mass(ESI): m/z 437(M+1).

PREPARATION EXAMPLE 23-3

In the same manner as in the aforementioned Preparation Example 15-4, (E)-3-(4-chloro-1-(2-chloro-4-((cyclohexyl)methyloxy)benzyl)-2-methylimidazol-5-yl)-2-propenic acid was obtained as thin yellow crystals (375 mg) from methyl (E)-3-(4-chloro-1-(2-chloro-4-((cyclohexyl)methyloxy)benzyl)-2-methylimidazol-5-yl)-2-propenate (418 mg).

$^1$H-NMR(CDCl$_3$): 0.95–1.10(2H, m), 1.15–1.38(4H, m), 1.64–1.89(5H, m), 2.35(3H, s), 3.71(2H, d, J=7 Hz), 5.16 (2H, s), 6.33(1H, d, J=8 Hz), 6.46(1H, d, J=16 Hz), 6.70(1H, dd, J=2, 8 Hz), 7.00(1H, d, J=2 Hz), 7.40(1H, d, J=16 Hz). Mass(ESI): m/z 421(M−1).

PREPARATION EXAMPLE 24-1

In the same manner as in the aforementioned Preparation Example 15-1,1-(4-benzyloxy-2-chlorobenzyl)-4-chloro-2-methylimidazole-5-carbaldehyde was obtained as a yellow oil (410 mg) from 5-chloro-2-methylimidazole-4-carbaldehyde (200 mg) and 4-benzyloxy-2-chlorobenzyl chloride (480 mg).

$^1$H-NMR(CDCl$_3$): 2.32(3H, s), 5.02(2H, s), 5.57(2H, s), 6.47(1H, d, J=8 Hz), 6.78(1H, dd, J=2, 8 Hz), 7.05(1H, d, J=2 Hz), 7.30–7.45(5H, m), 9.76(1H, s). Mass(ESI): m/z 375(M+1).

PREPARATION EXAMPLE 24-2

In the same manner as in the aforementioned Preparation Example 15-2, methyl (E)-3-(1-(4-benzyloxy-2-chlorobenzyl)-4-chloro-2-methylimidazol-5-yl)-2-propenate was obtained as a colorless oil (384 mg) from 1-(4-benzyloxy-2-chlorobenzyl)-4-chloro-2-methylimidazole-5-carbaldehyde (389 mg).

$^1$H-NMR(CDCl$_3$): 2.33(3H, s), 3.75(3H, s), 5.03(2H, s), 5.15(2H, s), 6.38(1H, d, J=8 Hz), 6.50(1H, d, J=16 Hz), 6.79(1H, dd, J=2, 8 Hz), 7.08(1H, d, J=2 Hz), 7.33(1H, d, J=16 Hz), 7.31–7.43(5H, m). Mass(ESI): m/z 431(M+1).

PREPARATION EXAMPLE 24-3

In the same manner as in the aforementioned Preparation Example 15-4, (E)-3-(1-(4-benzyloxy-2-chlorobenzyl)-4-chloro-2-methylimidazol-5-yl)-2-propenic acid was obtained as yellow crystals (296 mg) from methyl (E)-3-(1-(4-benzyloxy-2-chlorobenzyl)-4-chloro-2-methylimidazol-5-yl)-2-propenate (375 mg).

$^1$H-NMR(CDCl$_3$): 2.35(3H, s), 5.03(2H, s), 5.16(2H, s), 6.40(1H, d, J=8 Hz), 6.47(1H, d, J=16 Hz), 6.80(1H, dd, J=2, 8 Hz), 7.09(1H, d, J=2 Hz), 7.30–7.45(6H, m). Mass (ESI): m/z 415(M−1).

PREPARATION EXAMPLE 25-1

In the same manner as in the aforementioned Preparation Example 15-1,4-chloro-1-(2-chloro-4-(methylthio)benzyl)-2-methylimidazole-5-carbaldehyde was obtained as a colorless oil (344 mg) from 5-chloro-2-methylimidazole-4-carbaldehyde (200 mg) and 2-chloro-1-((methanesulfonyloxy)methyl)-4-(methylthio)benzene (379 mg).

$^1$H-NMR(CDCl$_3$): 2.32(3H, s), 2.46(3H, s), 5.58(2H, s), 6.43(1H, d, J=8 Hz), 7.03(1H, dd, J=2, 8 Hz), 7.26(1H, overlapped with CDCl$_3$), 9.76(1H, s). Mass(ESI): m/z 315 (M+1).

PREPARATION EXAMPLE 25-2

In the same manner as in the aforementioned Preparation Example 15-2, methyl (E)-3-(4-chloro-1-(2-chloro-4-(methylthio)benzyl)-2-methylimidazol-5-yl)-2-propenate was obtained as a yellow oil (384 mg) from 4-chloro-1-(2-chloro-4-(methylthio)benzyl)-2-methylimidazole-5-carbaldehyde (336 mg).

$^1$H-NMR(CDCl$_3$): 2.34(3H, s), 2.47(3H, s), 3.75(3H, s), 5.17(2H, s), 6.36(1H, d, J=8 Hz), 6.49(1H, d, J=16 Hz), 7.04(1H, dd, J=2, 8 Hz), 7.30(1H, d, J=2 Hz), 7.32(1H, d, J=16 Hz). Mass(ESI): m/z 371(M+1).

PREPARATION EXAMPLE 25-3

In the same manner as in the aforementioned Preparation Example 15-4, (E)-3-(4-chloro-1-(2-chloro-4-(methylthio)benzyl)-2-methylimidazol-5-yl)-2-propenic acid was obtained as thin yellow crystals (305 mg) from methyl (E)-3-(4-chloro-1-(2-chloro-4-(methylthio)benzyl)-2-methylimidazol-5-yl)-2-propenate (374 mg).

$^1$H-NMR(CDCl$_3$): 2.35 (3H, s), 2.47(3H, s), 5.18(2H, s), 6.38(1H, d, J=8 Hz), 6.47(1H, d, J=16 Hz), 7.05(1H, dd, J=2, 8 Hz), 7.30(1H, d, J=2 Hz), 7.37(1H, d, J=16 Hz). Mass(ESI): m/z 357(M+1).

PREPARATION EXAMPLE 26-1

In the same manner as in the aforementioned Preparation Example 15-1,4-chloro-1-(2-chloro-4-(trifluoromethyl)benzyl)-2-methylimidazole-5-carbaldehyde (189 mg) was obtained as a pale-yellow solid from 5-chloro-2-methylimidazole-4-carbaldehyde (100 mg) and 2-chloro-4-(trifluoromethyl)benzyl bromide (378 mg).

$^1$H-NMR(CDCl$_3$): 2.35(3H, s), 5.65(2H, s), 6.60(1H, d, J=8 Hz), 7.45(1H, d, J=8 Hz), 7.71(1H, s), 9.76(1H, s). Mass(ESI): m/e 337(M)+.

PREPARATION EXAMPLE 26-2

In the same manner as in the aforementioned Preparation Example 15-2, ethyl (E)-3-[4-chloro-1-(2-chloro-4-(trifluoromethyl)benzyl)-2-methylimidazol-5-yl]-2-propenate (207 mg) was obtained as a colorless oil from 4-chloro-1-(2-chloro-4-(trifluoromethyl)benzyl)-2-methylimidazole-5-carbaldehyde (185 mg).

$^1$H-NMR(CDCl$_3$): 1.30(3H, t, J=6 Hz), 2.35(3H, s), 4.20 (2H, q, J=6 Hz), 5.36(2H, s), 6.54(1H, d, J=16 Hz), 6.59(1H, d, J=8 Hz), 7.26(1H, d, J=16 Hz), 7.48(1H, d, J=8 Hz), 7.75(1H, s). Mass(ESI): m/e 408(M+H)+.

PREPARATION EXAMPLE 26-3

In the same manner as in the aforementioned Preparation Example 15-4, (E)-3-(4-chloro-1-(2-chloro-4-(trifluoromethyl)benzyl)-2-methylimidazol-5-yl)-2-propenic acid was obtained as colorless crystals (144 mg) from ethyl (E)-3-(4-chloro-1-(2-chloro-4-(trifluoromethyl)benzyl)-2-methylimidazol-5-yl)-2-propenate (203 mg).

$^1$H-NMR(CDCl$_3$): 2.36(3H, s), 5.26(2H, s), 6.49(1H, J=16 Hz), 6.60(1H, d, J=8 Hz), 7.33(1H, d, J=16 Hz), 7.49(1H, d, J=8 Hz), 7.75(1H, s). Mass(ESI): m/z 379(M+1).

PREPARATION EXAMPLE 27-1

In the same manner as in the aforementioned Preparation Example 15-1,4-chloro-1-(2-chloro-4-(phenoxymethyl)benzyl)-2-methylimidazole-5-carbaldehyde (482 mg) was obtained as a colorless oil from 5-chloro-2-methylimidazole-4-carbaldehyde (216 mg) and 2-chloro-1-((methanesulfonyloxy)methyl)-4-(phenoxymethyl)benzene (605 mg).

$^1$H-NMR(CDCl$_3$): 2.33(3H, s), 5.01(2H, s), 5.63(2H, s), 6.51(1H, d, J=8 Hz), 6.90–7.03(3H, m), 7.20–7.35(3H, m), 7.53(1H, d, J=2 Hz), 9.77(1H, s). Mass(ESI): m/e 375(M+H)+.

PREPARATION EXAMPLE 27-2

In the same manner as in the aforementioned Preparation Example 15-2, methyl (E)-3-(4-chloro-1-(2-chloro-4-(phenoxymethyl)benzyl)-2-methylimidazol-5-yl)-2-propenate (413 mg) was obtained as a white powder from 4-chloro-1-(2-chloro-4-(phenoxymethyl)benzyl)-2-methylimidazole-5-carbaldehyde (475 mg) and methyl (triphenylphosphoranylidene)acetate (623 mg).

$^1$H-NMR(CDCl$_3$): 2.34(3H, s), 3.74(3H, s), 5.03(2H, s), 5.22(2H, s), 6.47(1H, d, J=8 Hz), 6.50(1H, d, J=16 Hz), 6.91–7.04(3H, m), 7.21–7.34(3H, m), 7.22(1H, d, J=16 Hz), 7.57(1H, d, J=2 Hz). Mass(ESI): m/e 431(M+H)+.

PREPARATION EXAMPLE 27-3

In the same manner as in the aforementioned Preparation Example 15-4, (E)-3-(4-chloro-1-(2-chloro-4-(phenoxymethyl)benzyl)-2-methylimidazol-5-yl)-2-propenic acid (391 mg) was obtained as a white powder from methyl (E)-3-(4-chloro-1-(2-chloro-4-(phenoxymethyl)benzyl)-2-methylimidazol-5-yl)-2-propenate (404 mg).

$^1$H-NMR(CDCl$_3$): 2.34(3H, s), 5.01(2H, s), 5.21(2H, s), 6.46(1H, d, J=16 Hz), 6.47(1H, d, J=9 Hz), 6.89–7.02(3H, m), 7.20–7.34(3H, m), 7.34(1H, d, J=16 Hz), 7.55(1H, d, J=2 Hz). Mass(ESI): m/e 415(M−H)−.

PREPARATION EXAMPLE 28-1

In the same manner as in the aforementioned Preparation Example 15-1,4-chloro-1-(2-chloro-4-nitrobenzyl)-2-methylimidazole-5-carbaldehyde (304 mg) was obtained as pale-yellow crystals from 4-chloro-2-methylimidazole-5-carbaldehyde (200 mg) and 2-chloro-1-((methanesulfonyloxy) methyl)-4-nitrobenzene (404 mg).

$^1$H-NMR(CDCl$_3$): 2.37(3H, s), 5.67(2H, s), 6.67(1H, d, J=8 Hz), 8.06(1H, dd, J=8, 2 Hz), 8.34(1H, d, J=2 Hz), 9.75(1H, s).

PREPARATION EXAMPLE 28-2

In the same manner as in the aforementioned Preparation Example 15-2, methyl (E)-3-(4-chloro-1-(2-chloro-4-nitrobenzyl)-2-methylimidazol-5-yl)-2-propenate (297 mg) was obtained as pale-yellow crystals from 4-chloro-1-(2-chloro-4-nitrobenzyl)-2-methylimidazole-5-carbaldehyde (285 mg) and methyl (triphenylphosphoranylidene)acetate (546 mg).

$^1$H-NMR(CDCl$_3$): 2.35(3H, s), 3.74(3H, s), 5.29(2H, s), 6.52(1H, d, J=15 Hz), 6.65(1H, d, J=8 Hz), 7.27(1H, d, J=2 Hz), 8.08(1H, d, J=8, 2 Hz), 8.36(1H, d, J=2 Hz).

PREPARATION EXAMPLE 28-3

In the same manner as in the aforementioned Preparation Example 15-4, (E)-3-(4-chloro-1-(2-chloro-4-nitrobenzyl)-2-methylimidazol-5-yl)-2-propenic acid (233 mg) was obtained as pale-orange crystals from methyl (E)-3-(4-chloro-1-(2-chloro-4-nitrobenzyl)-2-methylimidazol-5-yl)-2-propenate (275 mg).

$^1$H-NMR(DMSO-d$_6$): 2.32(3H, s), 5.56(2H, s), 6.28(1H, d, J=15 Hz) 6.77(1H, d, J=8 Hz), 7.22(1H, d, J=15 Hz), 8.16(1H, dd, J=8, 2 Hz), 8.41(1H, d, J=2 Hz).

PREPARATION EXAMPLE 29-1

In the same manner as in the aforementioned Preparation Example 15-1, (E)-4-chloro-1-(2-chloro-4-(2-phenylethenyl)benzyl)-2-methylimidazole-5-carbaldehyde was obtained as orange crystals (471 mg) from 5-chloro-2-methylimidazole-4-carbaldehyde (209 mg) and (E)-2-chloro-4-(2-phenylethenyl)benzyl bromide (489 mg).

$^1$H-NMR(CDCl$_3$): 2.34(3H, s), 5.64(2H, s), 6.50(1H, d, J=8 Hz), 6.99(1H, d, J=16 Hz), 7.10(1H, d, J=16 Hz), 7.25–7.42(4H, m), 7.50(2H, d, J=8 Hz), 7.58(2H, s), 9.78 (1H, s). Mass(ESI): m/z 371(M+1).

PREPARATION EXAMPLE 29-2

In the same manner as in the aforementioned Preparation Example 15-2, methyl (2E)-3-(4-chloro-1-(2-chloro-4-((E)-2-phenylethenyl)benzyl)-2-methylimidazol-5-yl)-2-propenate was obtained as yellow amorphous (433 mg) from (E)-4-chloro-1-(2-chloro-4-(2-phenylethenyl)benzyl)-2-methylimidazole-5-carbaldehyde (390 mg).

$^1$H-NMR(CDCl$_3$): 2.36(3H, s), 3.74(3H, s), 5.22(2H, s), 6.45(1H, d, J=8 Hz), 6.51(1H, d, J=16 Hz), 6.99(1H, d, J=16 Hz), 7.12(1H, d, J=16 Hz), 7.26–7.41(5H, m), 7.50(2H, d, J=8 Hz), 7.60(1H, s). Mass(ESI): m/z 427(M+1).

PREPARATION EXAMPLE 29-3

In the same manner as in the aforementioned Preparation Example 15-4, (2E)-3-(4-chloro-1-(2-chloro-4-((E)-2-phenylethenyl)benzyl)-2-methylimidazol-5-yl)-2-propenic acid was obtained as colorless crystals (326 mg) from methyl (2E)-3-(4-chloro-1-(2-chloro-4-((E)-2-phenylethenyl)benzyl)-2-ethylimidazol-5-yl)-2-propenate (418 mg).

$^1$H-NMR(DMSO-d$_6$): 2.34(3H, s), 5.41(2H, s), 6.26(1H, d, J=16 Hz), 6.53(1H, d, J=8 Hz), 7.18–7.44(6H, m), 7.51(1H, d, J=8 Hz), 7.60(2H, d, J=8 Hz), 7.84(1H, s).

PREPARATION EXAMPLE 30-1

In the same manner as in the aforementioned Preparation Example 15-1, 1-(1-bromo-2-naphthyl)-4-chloro-2-methylimidazole-5-carbaldehyde (379 mg) was obtained as pale-yellow crystals from 4-chloro-2-methylimidazole-5-carbaldehyde (200 mg) and 1-bromo-2-(bromomethyl)naphthalene (457 mg).

$^1$H-NMR(CDCl$_3$): 2.32(3H, s), 5.88(2H, s), 6.58(1H, d, J=8 Hz), 7.56(1H, t, J=8 Hz), 7.65(1H, t, J=8 Hz), 7.73(1H, d, J=8 Hz), 7.82(1H, d, J=8 Hz), 8.35(1H, d, J=8 Hz), 9.82(1H, s).

PREPARATION EXAMPLE 30-2

In the same manner as in the aforementioned Preparation Example 15-2, methyl (E)-3-(1-(1-bromo-2-naphthyl)-4-chloro-2-methylimidazol-5-yl)-2-propenate (413 mg) was obtained as pale-yellow crystals from 1-(1-bromo-2-naphthyl)-4-chloro-2-methylimidazole-5-carbaldehyde (386 mg) and methyl (triphenylphosphoranylidene)acetate (603 mg).

$^1$H-NMR(CDCl$_3$): 2.36(3H, s), 3.70(3H, s), 5.44(2H, s), 6.50(1H, d, J=8 Hz), 6.53(1H, d, J=2 Hz), 7.37(1H, d, J=15 Hz), 7.57(1H, t, J=8 Hz), 7.67(1H, t, J=8 Hz), 7.75(1H, d, J=8 Hz), 7.83(1H, d, J=8 Hz), 8.35(1H, d, J=8 Hz).

PREPARATION EXAMPLE 30-3

In the same manner as in the aforementioned Preparation Example 15-4, (E)-3-(1-(1-bromo-2-naphthyl)-4-chloro-2-methylimidazol-5-yl)-2-propenic acid (389 mg) was obtained as colorless crystals from methyl (E)-3-(1-(1-bromo-2-naphthyl)-4-chloro-2-methylimidazol-5-yl)-2-propenate (393 mg).

$^1$H-NMR(DMSO-d$_6$): 2.37(3H, s), 5.61(2H, s), 6.24(1H, d, J=15 Hz), 6.58(1H, d, J=8 Hz), 7.24(1H, d, J=15 Hz), 7.65(1H, t, J=8 Hz), 7.76(1H, t, J=8 Hz), 7.97(2H, d, J=8 Hz), 8.29(1H, d, J=8 Hz).

PREPARATION EXAMPLE 31-1

In the same manner as in Preparation Example 15-1, 4-chloro-1-((3-chloro-5-(trifluoromethyl)pyridin-2-yl)methyl)-2-methylimidazole-5-carbaldehyde was obtained as a yellow oil (440 mg) from 5-chloro-2-methylimidazole-4-carbaldehyde (271 mg) and 3-chloro-2-chloromethyl-5-(trifluoromethyl)pyridine (474 mg).

$^1$H-NMR(CDCl$_3$): 2.38(3H,s), 5.76(2H, s), 7.97(1H, s), 8.58(1H, s), 9.66(1H, s). MS(ESI): m/z 336(M−1).

PREPARATION EXAMPLE 31-2

In the same manner as in Preparation Example 15-2, methyl (E)-3-(4-chloro-1-((3-chloro-5-(trifluoromethyl)pyridin-2-yl)methyl)-2-methylimidazol-5-yl)-2-propenate was obtained as a yellow oil (342 mg) from 4-chloro-1-((3-chloro-5-(trifluoromethyl)pyridin-2-yl)methyl)-2-methylimidazole-5-carbaldehyde (430 mg).

$^1$H-NMR(CDCl$_3$): 2.38(3H, s), 2.75(3H, s), 5.39(2H, s), 6.54(1H, d, J=16 Hz), 7.34(1H, d, J=16 Hz), 8.00(1H, s), 8.66(1H, s). MS(ESI): m/z 392(M−1).

PREPARATION EXAMPLE 31-3

In the same manner as in Preparation Example 15-4, (E)-3-(4-chloro-1-((3-chloro-5-(trifluoromethyl)pyridin-2-yl)methyl)-2-methylimidazol-5-yl)-2-propenic acid (240 mg) was obtained from methyl (E)-3-(4-chloro-1-((3-chloro-5-(trifluoromethyl)pyridin-2-yl)methyl)-2-methylimidazol-5-yl)-2-propenate (335 mg).

$^1$H-NMR(DMSO-d$_6$): 2.28(3H, s), 5.68(2H, s), 6.28(1H, d, J=16 Hz), 7.26(1H, d, J=16 Hz), 8.60(1H, s), 8.89(1H, s). MS(ESI): m/z 38.0(M+1).

PREPARATION EXAMPLE 32-1

3-(4-(N,N-bis-(tert-Butoxycarbonyl)amino)-2-chlorobenzyl)-5-chloro-2-methylimidazole-4-carbaldehyde (844 mg) was obtained as white amorphous from 5-chloro-2-methylimidazole-4-carbaldehyde (340 mg) and 4-(N,N-bis-(tert-butoxycarbonyl)amino)-2-chlorobenzyl bromide (1.19 g).

$^1$H-NMR(CDCl$_3$): 1.42(18H, s), 2.30(3H, s), 5.65(2H, s), 6.52(1H, d, J=8 Hz), 6.99(1H, dd, J=8, 2 Hz), 7.26(1H, d, J=2 Hz), 9.76(1H, s).

PREPARATION EXAMPLE 32-2

Methyl (E)-3-(1-(4-(N,N-bis-(tert-butoxycarbonyl)amino)-2-chlorobenzyl)-4-chloro-2-methylimidazol-5-yl)-2-propenate (902 mg) was obtained as white amorphous from 3-(4-(N,N-bis-(tert-butoxycarbonyl)amino)-2-chlorobenzyl)-5-chloro-2-methylimidazole-4-carbaldehyde (834 mg).

$^1$H-NMR(CDCl$_3$): 1.42(18H, s), 2.34(3H, s), 3.72(3H, s), 5.23(2H, s), 6.45(1H, d, J=16 Hz), 6.48(1H, d, J=8 Hz), 7.01(1H, dd, J=8, 2 Hz), 7.30(1H, d, J=2 Hz), 7.33(1H, d, J=16 Hz). MS(ESI): m/z 541(M+1)

PREPARATION EXAMPLE 32-3

Methyl (E)-3-(1-(4-(N,N-bis-(tert-butoxycarbonyl)amino)-2-chlorobenzyl)-4-chloro-2-methylimidazol-5-yl)-2-propenate (882 mg) was dissolved in dioxane (8.8 ml), and 1N aqueous sodium hydroxide solution (5.0 ml) was added. The mixture was stirred at 80° C. for 5.5 hr. To the reaction mixture was added 1N aqueous sodium hydroxide solution (3.0 ml) and the mixture was stirred at 80° C. for 18 hr and 1N aqueous sodium hydroxide solution (1.0 ml) was added again. The reaction mixture was stirred at 80° C. for 2 hr and with refluxing for 3 hr, and neutralized under ice-cooling. The precipitate was collected by filtration and washed with water to give (E)-3-(1-(4-(tert-butoxycarbonyl)amino)-2-chlorobenzyl)-4-chloro-2-methylimidazol-5-yl)-2-propenic acid (452 mg) as a white powder.

$^1$H-NMR(DMSO-d$_6$): 1.45(18H, s), 2.31 (3H, s), 5.28 (2H, s), 6.22(1H, d, J=16 Hz), 6.46(1H, d, J=8 Hz), 7.18(1H, d, J=16 Hz), 7.28(1H, dd, J=8, 2 Hz), 7.71(1H, d, J=2 Hz), 9.64(1H, s). MS(ESI): m/z 427(M+1)

PREPARATION EXAMPLE 33-1

2-Ethylimidazole (1.0 g) was dissolved in dry ethanol (10 ml), and bromine (1.2 ml) was added dropwise under ice-cooling. The reaction mixture was stirred at the same temperature for 3 hr and at room temperature for 3 hr, and left standing overnight at room temperature. After neutralizing with 5N aqueous sodium hydroxide solution, sodium nitrite (1.4 g) and water (10 ml) were added and the mixture was refluxed under heating for 10 hr. The reaction mixture was partitioned between chloroform and water and the aqueous layer was extracted twice with chloroform. The organic layers were combined, dried over magnesium sulfate and concentrated to dryness under reduced pressure. The residue was purified by silica gel column chromatography (chloroform/methanol=98:2) to give 4-bromo-2-ethylimidazole (1.02 g) as a pale-yellow solid.

$^1$H-NMR(CDCl$_3$): 1.32(3H, t, J=6 Hz), 2.75(2H, q, J=6 Hz), 6.89(1H, s). MS(ESI): m/z 176(M+1)

PREPARATION EXAMPLE 33-2

4-Bromo-2-ethylimidazole (24.4 g) was dissolved in ethanol (244 ml), and 1N aqueous sodium hydroxide solution (105 ml) and 37% formalin (15.6 ml) were added. The mixture was stirred at room temperature for 15 hr. The reaction mixture was neutralized under ice-cooling and concentrated to dryness under reduced pressure. The residue was extracted with chloroform-methanol (4/1) and insoluble matter was filtered off. The residue was concentrated to dryness under reduced pressure. The residue was purified by silica gel column chromatography (chloroform/methanol=49:1–19:1) to give 4-bromo-2-ethyl-5-(hydroxymethyl)imidazole (18.9 g) as a yellow powder.

$^1$H-NMR(DMSO-d$_6$): 1.16(3H, t, J=6 Hz), 2.55(2H, q, J=6 Hz), 4.30(2H, d, J=4 Hz), 5.14(1H, t, J=4 Hz).

PREPARATION EXAMPLE 33-3

4-Bromo-2-ethyl-5-(hydroxymethyl)imidazole (18.9 g) was dissolved in dry dimethylformamide (189 ml), and manganese dioxide (80.1 g) was added. The mixture was stirred at room temperature for 5 hr and left standing overnight. The reaction mixture was filtered through celite and insoluble matter was washed with chloroform. The filtrate and washing were combined and concentrated to dryness under reduced pressure. The residue was washed with water to give 5-bromo-2-ethylimidazole-4-carbaldehyde (12.9 g) as a brown powder.

$^1$H-NMR(CDCl$_3$): 1.37(3H, t, J=6 Hz), 2.86(2H, q, J=6 Hz), 9.58(1H, s).

PREPARATION EXAMPLE 33-4

In the same manner as in Preparation Example 1-4,5-chloro-2-ethylimidazole-4-carbaldehyde was obtained as orange crystals (6.6 g) from 5-bromo-2-ethylimidazole-4-carbaldehyde (12 g).

$^1$H-NMR(DMSO-d$_6$): 1.20(3H, t, J=7 Hz), 2.66(2H, q, J=7 Hz), 9.59 (1H, s). Mass(ESI): m/z 157(M−1).

PREPARATION EXAMPLE 33-5

In the same manner as in Preparation Example 15-1,4-chloro-1-(2-chloro-4-(n-pentyloxy)benzyl)-2-ethylimidazole-5-carbaldehyde was obtained as a pale-yellow oil (260 mg) from 5-chloro-2-ethylimidazole- 4-carbaldehyde (130 mg) and 2-chloro-4-(1-pentyloxy)benzyl bromide (335 mg).

$^1$H-NMR(CDCl$_3$): 0.92(3H, t, J=7 Hz), 1.25(3H, t, J=7 Hz), 1.30–1.49(4H, m), 1.70–1.83(2H, m), 2.59(2H, q, J-7 Hz), 3.90(2H, t, J=7 Hz), 5.57(2H, s), 6.43(1H, d, J=8 Hz), 6.68(1H, dd, J=8, 2 Hz), 6.95(1H, d, J=2 Hz), 9.77(1H, s). Mass(ESI): m/z 369(M−1).

PREPARATION EXAMPLE 33-6

In the same manner as in Preparation Example 15-2, methyl (E)-3-(4-chloro-1-(2-chloro-4-(1-pentyloxy)benzyl)-2-ethylimidazol-5-yl)-2-propenate was obtained as a yellow solid (265 mg) from 4-chloro-1-(2-chloro-4-(1-pentyloxy)benzyl)-2-ethylimidazole-5-carbaldehyde(254 mg) and methyl (triphenylphosphoranylidene)acetate (354 mg).

$^1$H-NMR(CDCl$_3$): 0.93(3H, t, J=7 Hz), 1.27(3H, t, J=7 Hz), 1.31–1.49(4H, m), 1.71–1.83(2H, m), 2.61(2H, q, J=7 Hz), 3.74(3H, s), 3.90(2H, q, J=7 Hz), 5.16(2H, s), 6.35(1H, d, J=8 Hz), 6.49(1H, d, J=15 Hz), 6.70(1H, dd, J=8, 2 Hz), 6.98(1H, d, J=2 Hz), 7.34(1H, d, J=15 Hz). Mass(ESI): m/z 427(M+1).

PREPARATION EXAMPLE 33-7

In the same manner as in Preparation Example 15-4, (E)-3-(4-chloro-1-(2-chloro-4-(1-pentyloxy)benzyl)-2-ethylimidazol-5-yl)-2-propenic acid was obtained as colorless crystals (178 mg) from methyl (E)-3-(4-chloro-1-(2-chloro-4-(1-pentyloxy)benzyl)-2-ethylimidazol-5-yl)-2-propenate (254 mg).

$^1$H-NMR(DMSO-d$_6$): 0.88(3H, t, J=7 Hz), 1.14(3H, t, J=7 Hz), 1.25–1.44(4H, m), 1.63–1.75(2H, m), 2.65(2H, q, J=7 Hz), 3.95(2H, q, J=7 Hz), 5.31(2H, s), 6.27(1H, d, J=15 Hz), 6.40(1H, d, J=8 Hz), 6.67(1H, dd, J=8, 2 Hz), 7.13(1H, d, J=2 Hz), 7.23(1H, d, J=15 Hz). Mass(ESI): m/z 409(M−1).

PREPARATION EXAMPLE 34-1

In the same manner as in Preparation Example 15-1,1-(4-bromo-2-chlorobenzyl)-4-chloro-2-ethylimidazole-5-carbaldehyde was obtained as a pale-yellow solid (2.86 g) from 5-chloro-2-ethylimidazole-4-carbaldehyde (1.5 g) and 4-bromo-2-chlorobenzyl bromide (3.77 g).

$^1$H-NMR(CDCl$_3$): 1.28(3H, t, J=7 Hz), 2.58(2H, q, J=7 Hz), 5.56(2H, s), 6.35(1H, d, J=8 Hz), 7.31(1H, dd, J=8, 1 Hz), 7.60(1H, d, J=1 Hz), 9.76(1H, s). Mass(ESI): m/z 363(M+1).

PREPARATION EXAMPLE 34-2

In the same manner as in Preparation Example 15-2, methyl (E)-3-(1-(4-bromo-2-chlorobenzyl)-4-chloro-2-ethylimidazol-5-yl)-2-propenate was obtained as a colorless solid (1.06 g) from 1-(4-bromo-2-chlorobenzyl)-4-chloro-2-ethylimidazole-5-carbaldehyde (1.0 g) and methyl (triphenylphosphoranylidene)acetate (1.39 g).

$^1$H-NMR(CDCl$_3$): 1.28(3H, t, J=7 Hz), 2.59(2H, q, J=7 Hz), 3.75(3H, s), 5.16(2H, s), 6.32(1H, d, J=8 Hz), 6.50(1H, d, J=15 Hz), 7.29(1H, d, J=15 Hz), 7.34(1H, dd, J=8, 1 Hz), 7.63(1H, d, J=1 Hz). Mass(ESI): m/z 419(M+1).

PREPARATION EXAMPLE 34-3

In the same manner as in Preparation Example 15-4, (E)-3-(1-(4-bromo-2-chlorobenzyl)-4-chloro-2-ethylimidazol-5-yl)-2-propenic acid was obtained as a colorless solid (228 mg) from methyl (E)-3-(1-(4-bromo-2-chlorobenzyl)-4-chloro-2-ethylimidazol-5-yl)-2-propenate (260 mg).

$^1$H-NMR(DMSO-d$_6$): 1.14(3H, t, J=7 Hz), 2.65(2H, q, J=7 Hz), 5.38(2H, s), 6.36(1H, d, J=15 Hz), 6.43(1H, d, J=8 Hz), 7.20(1H, d, J=15 Hz), 7.52(1H, dd, J=8, 1 Hz), 7.87 (1H, d, J=1 Hz). Mass(ESI): m/z 403(M+1).

PREPARATION EXAMPLE 35-1

In the same manner as in Preparation Example 15-1,4-chloro-1-(2-chloro-4-iodobenzyl)-2-ethylimidazole-4-carbaldehyde was obtained as a pale-yellow gum (2.68 g) from 5-chloro-2-ethylimidazole-4-carbaldehyde (1.2 g) and 2-chloro-4-iodobenzyl bromide (3.76 g).

$^1$H-NMR(CDCl$_3$): 1.28(3H, t, J=7 Hz), 2.58(2H, q, J=7 Hz), 5.56(2H, s), 6.20(1H, d, J=8 Hz), 7.50(1H, dd, J=8, 1 Hz), 7.78(1H, d, J=1 Hz), 9.75(1H, s). Mass(ESI): m/z 409(M+1).

PREPARATION EXAMPLE 35-2

In the same manner as in Preparation Example 15-2, methyl (E)-3-(4-chloro-1-(2-chloro-4-iodobenzyl)-2-ethylimidazol-5-yl)-2-propenate was obtained as pale-yellow crystals (2.53 g) from 4-chloro-1-(2-chloro-4-iodobenzyl)-2-ethylimidazole-5-carbaldehyde (2.65 g) and methyl (triphenylphosphoranylidene)acetate (3.25 g).

$^1$H-NMR(CDCl$_3$): 1.28(3H, t, J=7 Hz), 2.59(2H, q, J=7 Hz), 3.75(3H, s), 5.15(2H, s), 6.16(1H, d, J=8 Hz), 6.49(1H, d, J=15 Hz), 7.27(1H, d, J=15 Hz), 7.51(1H, dd, J=8, 1 Hz), 7.81(1H, d, J=1 Hz). Mass(ESI): m/z 465(M+1).

PREPARATION EXAMPLE 35-3

In the same manner as in Preparation Example 17-1, methyl (E)-3-(4-chloro-1-(2-chloro-4-(phenylethynyl)benzyl)-2-ethylimidazol-5-yl)-2-propenic acid was obtained as gray crystals (522 mg) from methyl (E)-3-(4-chloro-1-(2-chloro-4-iodobenzyl)-2-ethylimidazol-5-yl)-2-propenate (600 mg) and phenylacetylene (439 mg).

$^1$H-NMR(CDCl$_3$): 1.28(3H, t, J=7 Hz), 2.62(2H, q, J=7 Hz), 3.75(3H, s), 5.23(2H, s), 6.44(1H, d, J=8 Hz), 6.50(1H, d, J=15 Hz), 7.28–7.40(4H, m), 7.47–7.55(2H, m), 7.63(1H, d, J=1 Hz). Mass(ESI): m/z 439(M+1).

PREPARATION EXAMPLE 35-4

In the same manner as in Preparation Example 15-4, (E)-3-(4-chloro-1-(2-chloro-4-(phenylacetinyl)benzyl)-2-ethylimidazol-5-yl)-2-propenic acid was obtained as gray crystals (410 mg) from methyl (E)-3-(4-chloro-1-(2-chloro-4-(phenylethynyl)benzyl)-2-ethylimidazol-5-yl)-2-propenate (500 mg).

$^1$H-NMR(DMSO-d$_6$): 1.15(3H, t, J=7 Hz), 2.67(2H, q, J=7 Hz), 5.46(2H, s), 6.27(1H, d, J=15 Hz), 6.54(1H, d, J=8 Hz), 7.23(1H, d, J=15 Hz), 7.40–7.60(6H, m), 7.79(1H, d, J=1 Hz). Mass(ESI): m/z 423(M−1).

PREPARATION EXAMPLE 36-1

A suspension of methyl (E)-3-(4-chloro-1-(2-chloro-4-iodobenzyl)-2-ethylimidazol-5-yl)-2-propenate (600 mg), palladium acetate (600 mg) and tri-o-tolylphosphine (39 mg) in anhydrous triethylamine (5.4 ml) was stirred at room temperature in a nitrogen atmosphere. Ten min. later, styrene (672 mg) was added and the reaction mixture was heated to 100° C. After heating for 2 hr, the mixture was ice-cooled. Water was added and the mixture was extracted with chloroform. The organic layer was washed with saturated brine, dried over anhydrous magnesium sulfate, and filtrated. The filtrate was concentrated, and the residue was applied to flash silica gel chromatography (silica gel, 150 ml). Elution with hexane:ethyl acetate=10:1–7:1–5:1–4:1 gave a pale-yellow gum (435 mg). This was crystallized from isopropyl ether to give methyl (E)-3-(4-chloro-1-(2-chloro-4-((E)-2-phenylethenyl)benzyl)-2-ethylimidazol-5-yl)-2-propenate as pale-yellow crystals (405 mg).

$^1$H-NMR(CDCl$_3$): 1.29(3H, t, J=7 Hz), 2.63(2H, q, J=7 Hz), 3.74(3H, s), 5.23(2H, s), 6.43(1H, d, J=8 Hz), 6.51(1H, d, J=15 Hz), 6.99(1H, d, J=15 Hz), 7.21(1H, d, J=15 Hz), 7.24–7.41(5H, m), 7.51(2H, d, J=8 Hz), 7.60(1H, s). Mass (ESI): m/z 441(M+1).

PREPARATION EXAMPLE 36-2

In the same manner as in Preparation Example 15-4, (E)-3-(4-chloro-1-(2-chloro-4-((E)-2-phenylethenyl)benzyl)-2-ethylimidazol-5-yl)-2-propenic acid was obtained as pale-yellow crystals (363 mg) from methyl (E)-3-(4-chloro-1-(2-chloro-4-((E)-2-phenylethenyl)benzyl)-2-ethylimidazol-5-yl)-2-propenate (400 mg).

$^1$H-NMR(DMSO-d$_6$): 1.16(3H, t, J=7 Hz), 2.68(2H, q, J=7 Hz), 5.42(2H, s), 6.27(1H, d, J=15 Hz), 6.50(1H, d, J=8 Hz), 7.28–7.44(6H, m), 7.52(1H, dd, J=8, 1 Hz), 7.60(2H, d, J=8 Hz), 7.83(1H, d, J=1 Hz). Mass(ESI): m/z 425(M−1).

PREPARATION EXAMPLE 37-1

In the same manner as in Preparation Example 33-2, 2,4-dimethyl-5-(hydroxymethyl)imidazole (4.74 g) was obtained as a pale-yellow oil from 2,4-dimethylimidazole (2.6 g).

$^1$H-NMR(DMSO-d$_6$): 2.20(3H, s), 2.50(3H, s), 4.41(2H, s)

PREPARATION EXAMPLE 37-2

In the same manner as in Preparation Example 33-3, a crude purified product of 2,4-dimethylimidazole-5-carbaldehyde (3.00 g) was obtained as a yellow solid from 2,4-dimethyl-5-(hydroxymethyl)imidazole (4.10 g). Mass (ESI): m/z 123(M−H)$^−$

PREPARATION EXAMPLE 37-3

In the same manner as in Preparation Example 15-1,1-(4-bromo-2-chlorobenzyl)-2,4-dimethyl-1H-imidazole-5-carbaldehyde (481 mg) was obtained as pale-yellow crystals and 1-(4-bromo-2-chlorobenzyl)-2,5-dimethyl-1H-imidazole-4-carbaldehyde (587 mg) as a pale-yellow oil from 2,4-dimethylimidazole-5-carbaldehyde (587 mg) and 4-bromo-2-chlorobenzylmethanesulfonate (1.70 g).

1-(4-bromo-2-chlorobenzyl)-2,4-dimethyl-1H-imidazole-5-carbaldehyde $^1$H-NMR(CDCl$_3$): 2.31(3H, s), 2.52(3H, s), 5.54(2H, s), 6.31(1H, d, J=8 Hz), 7.27(1H, dd, J=8, 2 Hz), 7.58(1H, d, J=2 Hz), 9.75(1H, s)

1-(4-bromo-2-chlorobenzyl)-2,5-dimethyl-1H-imidazole-4-carbaldehyde $^1$H-NMR(CDCl$_3$): 2.33(3H, s), 2.43(3H, s), 5.07(2H, s), 6.23(1H, d, J=8 Hz), 7.34(1H, dd, J=8, 2 Hz), 7.63(1H, d, J=2 Hz), 9.75(1H, s)

PREPARATION EXAMPLE 37-4

In the same manner as in Preparation Example 15-2, a crude purified product of methyl (E)-3-(1-(4-bromo-2-chlorobenzyl)-2,4-dimethylimidazol-5-yl)-2-propenate (554 mg) was obtained as colorless crystals from 1-(4-bromo-2-chlorobenzyl)-2,4-dimethyl-1H-imidazole-5-carbaldehyde (453 mg) and methyl (triphenylphosphoranylidene)acetate (1.25 g).

$^1$H-NMR(CDCl$_3$): 2.32(3H, s), 2.42(3H, s), 3.73(3H, s), 5.12(2H, s), 5.89(1H, d, J=16 Hz), 6.29(1H, d, J=8 Hz), 7.30(1H, dd, J=8, 2 Hz), 7.37–7.70(2H, m)

PREPARATION EXAMPLE 37-5

In the same manner as in Preparation Example 15-4, (E)-3-(1-(4-bromo-2-chlorobenzyl)-2,4-dimethylimidazol-5-yl)-2-propenic acid (158 mg) was obtained as colorless crystals from methyl (E)-3-(1-(4-bromo-2-chlorobenzyl)-2,4-dimethylimidazol-5-yl)-2-propenate (554 mg).

$^1$H-NMR(DMSO-d$_6$): 2.26(3H, s), 2.28(3H, s), 5.28(2H, s), 5.75(1H, d, J=14 Hz), 6.32(1H, d, J=8 Hz), 7.27(1H, d, J=14 Hz), 7.52(1H, dd, J=8, 2 Hz), 7.85(1H, d, J=2 Hz)

PREPARATION EXAMPLE 38-1

In the same manner as in Preparation Example 15-1,4-bromo-1-(2-chloro-4-(1-pentyloxy)benzyl)-2-methyl-1H-imidazole-5-carbaldehyde (9.11 g) was obtained as a pale-yellow oil from 4-bromo-2-methylimidazole-5-carbaldehyde (5.00 g) and 2-chloro-4-(1-pentyloxy) benzylbromide (9.26 g).

$^1$H-NMR(CDCl$_3$): 0.92(3H, t, J=7 Hz), 1.30–1.45(4H, m), 1.70–1.80(2H, m), 2.33(3H, s), 3.90(2H, t, J=7 Hz), 5.58(2H, s), 6.44(1H, d, J=8 Hz), 6.70(1H, dd, J=8, 2 Hz), 6.95(1H, d, J=2 Hz), 9.71(1H, s)

PREPARATION EXAMPLE 38-2

In the same manner as in Preparation Example 15-2, methyl (E)-3-(4-bromo-1-(2-chloro-4-(1-pentyloxy)benzyl)-2-methylimidazol-5-yl)-2-propenate (488 mg) was obtained as colorless crystals from 4-bromo-1-(2-chloro-4-(1-pentyloxy)benzyl)-2-methyl-1H-imidazole-5-carbaldehyde (479 mg) and methyl (triphenylphosphoranylidene) acetate (481 mg).

$^1$H-NMR(CDCl$_3$): 0.93(3H, t, J=7 Hz), 1.33–1.45(4H, m), 1.72–1.80(2H, m), 2.35(3H, s), 3.75(3H, s), 3.92(2H, t, J=7 Hz), 5.17(2H, s), 6.36(1H, d, J=8 Hz), 6.52(1H, d, J=15 Hz), 6.71(1H, dd, J=8, 2 Hz), 6.99(1H, d, J=2 Hz), 7.35(1H, d, J=15 Hz)

PREPARATION EXAMPLE 38-3

In the same manner as in Preparation Example 15-4, (E)-3-(4-bromo-1-(2-chloro-4-(1-pentyloxy)benzyl)-2-methylimidazol-5-yl)-2-propenic acid (447 mg) was obtained as a colorless powder from methyl (E)-3-(4-bromo-1-(2-chloro-4-(1-pentyloxy)benzyl)-2-methylimidazol-5-yl)-2-propenate (462 mg).

$^1$H-NMR(DMSO-d$_6$): 0.88(3H, t, J=7 Hz), 1.25–1.42(4H, m), 1.62–1.72(2H, m), 2.33(3H, s), 3.96(2H, t, J=7 Hz), 5.31(2H, s), 6.29(1H, d, J=15 Hz), 6.42(1H, d, J=8 Hz), 6.88(1H, dd, J=8, 2 Hz), 7.13(1H, d, J=2 Hz), 7.22(1H, d, J=15 Hz)

PREPARATION EXAMPLE 39-1

Lithium chloride (180 mg) was suspended in 1,4-dioxane (10 ml), and 4-bromo-1-(2-chloro-4-(1-pentyloxy)benzyl)-2-methyl-1H-imidazole-5-carbaldehyde (707 mg), vinyltributyltin (617 mg) and tetrakis(triphenylphosphine)palladium(0) (102 mg) were added. The mixture was refluxed under heating for 12 hr. Water was added to the reaction mixture and the mixture was extracted with ethyl acetate. The organic layer was washed with saturated brine, dried over anhydrous magnesium sulfate and concentrated under reduced pressure. The residue was applied to silica gel column chromatography and eluted with hexane/ethyl acetate=5/1. The objective fraction was concentrated under reduced pressure to give 1-(2-chloro-4-(1-pentyloxy)benzyl)-4-ethenyl-2-methyl-1H-imidazole-5-carbaldehyde(538 mg) as a pale-yellow gum.

$^1$H-NMR (CDCl$_3$): 0.92(3H, t, J=7 Hz), 1.30–1.47(4H, m), 1.70–1.80(2H, m), 2.34(3H, s), 3.90(2H, t, J=7 Hz), 5.54(1H, dd, J=8, 2 Hz), 5.56(2H, s), 6.26(1H, dd, J=15, 2 Hz), 6.40(1H, d, J=8 Hz), 6.67(1H, dd, J=8, 2 Hz), 6.95–7.05(2H, m), 9.90(1H, s)

PREPARATION EXAMPLE 39-2

1-(2-Chloro-4-(1-pentyloxy)benzyl)-4-ethenyl-2-methyl-1H-imidazole-5-carbaldehyde (575 mg) was dissolved in 1,4-dioxane (6 ml) and palladium carbon (50 mg) was added. The mixture was stirred under a hydrogen atmosphere for 1.5 hr. The reaction mixture was filtered through celite. Water was added to the filtrate and extracted with ethyl acetate. The organic layer was washed with brine, dried over anhydrous magnesium sulfate, and concentrated under reduced pressure. The residue was applied to silica gel column chromatography and eluted with chloroform/ethyl acetate=2/1. The objective fraction was concentrated under reduced pressure to give 1-(2-chloro-4-(1-pentyloxy)benzyl)-4-ethyl- 2-methyl-1H-imidazole-5-carbaldehyde (283 mg) as a black brown oil.

$^1$H-NMR(CDCl$_3$): 0.92(3H, t, J=7 Hz), 1.35(3H, t, J=7 Hz), 1.33–1.48(4H, m), 1.72–1.80(2H, m), 2.31(3H, s), 2.87(2H, q, J=7 Hz), 3.90(2H, t, J=7 Hz), 5.55(2H, s), 6.38(1H, d, J=8 Hz), 6.67(1H, dd, J=8, 2 Hz), 6.94(1H, d, J=2 Hz), 9.77(1H, s)

PREPARATION EXAMPLE 39-3

In the same manner as in Preparation Example 15-2, methyl (E)-3-(1-(2-chloro-4-(1-pentyloxy)benzyl)-4-ethyl-2-methylimidazol-5-yl)-2-propenate (273 mg) was obtained as pale-yellow crystals from 1-(2-chloro-4-(1-pentyloxy) benzyl)-4-ethyl-2-methyl-1H-imidazole-5-carbaldehyde (265 mg) and methyl (triphenylphosphoranylidene)acetate (940 mg).

$^1$H-NMR(CDCl$_3$): 0.93(3H, t, J=7 Hz), 1.31(3H, t, J=7 Hz), 1.32–1.47(4H, m), 1.70–1.81(2H, m), 2.34(3H, s), 2.75(2H, q, J=7 Hz), 3.73(3H, s), 3.91(2H, t, J=7 Hz), 5.14(2H, s), 5.86(1H, d, J=15 Hz), 6.32(1H, d, J=8 Hz), 6.68(1H, dd, J=8, 2 Hz), 6.98(1H, d, J=2 Hz), 7.45(1H, d, J=15 Hz)

PREPARATION EXAMPLE 39-4

In the same manner as in Preparation Example 15-4, (E)-3-(1-(2-chloro-4-(1-pentyloxy)benzyl)-4-ethyl-2-methylimidazol-5-yl)-2-propenic acid (222 mg) was obtained as a colorless powder from methyl (E)-3-(1-(2-chloro-4-(1-pentyloxy)benzyl)-4-ethyl-2-methylimidazol-5-yl)-2-propenate (253 mg).
$^1$H-NMR(DMSO-d$_6$): 0.88(3H, t, J=7 Hz), 1.19(3H, t, J=7 Hz), 1.28–1.42(4H, m), 1.63–1.73(2H, m), 2.28(3H, s), 2.62(2H, q, J=7 Hz), 3.95(2H, t, J=7 Hz), 5.21(2H, s), 5.72(1H, d, J=15 Hz), 6.28(1H, d, J=8 Hz), 6.87(1H, dd, J=8, 2 Hz), 7.12(1H, d, J=2 Hz), 7.29(1H, d, J=15 Hz)

PREPARATION EXAMPLE 40-1

4-Bromo-1-(2-chloro-4-(1-pentyloxy)benzyl)-2-methyl-1H-imidazole-5-carbaldehyde (4.00 g) was dissolved in a mixed solvent of methanol (20 ml) and 1,4-dioxane (20 ml), and palladium carbon (400 mg) and potassium acetate (1.08 g) were added. The reaction mixture was stirred under a hydrogen atmosphere for 3 hr. The reaction mixture was filtered through celite and the filtrate was concentrated under reduced pressure. Water was added to the residue and extracted with ethyl acetate. The organic layer was washed with saturated brine, dried over anhydrous magnesium sulfate, and concentrated under reduced pressure. The residue was applied to silica gel column chromatography and eluted with hexane/ethyl acetate=1/2. The objective fraction was concentrated under reduced pressure to give 1-(2-chloro-4-(1-pentyloxy)benzyl)-2-methyl-1H-imidazole-5-carbaldehyde (3.10 g) as a pale-yellow oil.
$^1$H-NMR(CDCl$_3$): 0.92(3H, t, J=7 Hz), 1.33–1.47(4H, m), 1.72–1.82(2H, m), 2.35(3H, s), 3.90(2H, t, J=7 Hz), 5.59(2H, s), 6.37(1H, d, J=8 Hz), 6.67(1H, dd, J=8, 2 Hz), 6.95(1H, d, J=2 Hz), 7.78(1H, s), 9.68(1H, s)

PREPARATION EXAMPLE 40-2

In the same manner as in Preparation Example 42-1 to be mentioned later, a crude purified product of ethyl 2-benzyl-3-(1-(2-chloro-4-(1-pentyloxy)benzyl)-2-methylimidazol-5-yl)-3-hydroxypropanate was obtained as a brown oil from 1-(2-chloro-4-(1-pentyloxy)benzyl)-2-methyl-1H-imidazole-5-carbaldehyde (500 mg) and ethyl 3-phenyl propionate (361 mg).

PREPARATION EXAMPLE 40-3

In the same manner as in Preparation Example 42-2 to be mentioned later, ethyl (E)-2-benzyl-3-(1-(2-chloro-4-(1-pentyloxy)benzyl)-2-methylimidazol-5-yl)-2-propenate (405 mg) was obtained as a pale-yellow oil from the crude purified product of ethyl 2-benzyl-3-(1-(2-chloro-4-(1-pentyloxy)benzyl)-2-methylimidazol-5-yl)-3-hydroxypropanate.
$^1$H-NMR(CDCl$_3$): 0.93(3H, t, J=7 Hz), 1.19(3H, t, J=7 Hz), 1.32–1.47(4H, m), 1.70–1.82(2H, m), 2.36(3H, s), 3.92(2H, t, J=7 Hz), 3.97(2H, s), 4.14(2H, q, J=7 Hz), 5.17(2H, s), 6.32(1H, d, J=8 Hz), 6.69(1H, dd, J=8, 2 Hz), 6.98(1H, d, J=2 Hz), 7.13–7.28(6H, m), 7.46(1H, s)

PREPARATION EXAMPLE 40-4

In the same manner as in Preparation Example 15-4, (E)-2-benzyl-3-(1-(2-chloro-4-(1-pentyloxy)benzyl)-2-methylimidazol-5-yl)-2-propenic acid (308 mg) was obtained as a pale-yellow powder from ethyl (E)-2-benzyl-3-(1-(2-chloro-4-(1-pentyloxy)benzyl)-2-methylimidazol-5-yl)-2-propenate (385 mg).
$^1$H-NMR(DMSO-d$_6$): 0.88(3H, t, J=7 Hz), 1.27–1.43(4H, m), 1.65–1.74(2H, m), 2.29(3H, s), 3.86(2H, s), 3.96(2H, t, J=7 Hz), 5.26(2H, s), 6.31(1H, d, J=8 Hz), 6.85(1H, dd, J=8, 2 Hz), 7.07–7.30(7H, m), 7.43(1H, s)

PREPARATION EXAMPLE 41-1

In the same manner as in Preparation Example 42-1, a crude purified product of ethyl 3-(1-(2-chloro-4-(1-pentyloxy)benzyl)-2-ethylimidazol-5-yl)-3-hydroxy-2-(1-pentyl)propanate was obtained as a brown oil from 1-(2-chloro-4-(1-pentyloxy)benzyl)-2-methyl-1H-imidazole-5-carbaldehyde (500 mg) and ethyl n-heptanate (321 mg).

PREPARATION EXAMPLE 41-2

In the same manner as in Preparation Example 42-2, ethyl (E)-3-(1-(2-chloro-4-(1-pentyloxy)benzyl)-2-methylimidazol-5-yl)-2-(1-pentyl)-2-propenate (425 mg) was obtained as a pale-yellow oil from the crude purified product of ethyl 3-(1-(2-chloro-4-(1-pentyloxy)benzyl)-2-methylimidazol-5-yl)-3-hydroxy-2-(1-pentyl)propanate.
$^1$H-NMR(CDCl$_3$): 0.87–0.94(6H, m), 1.27(3H, t, J=7 Hz), 1.32–1.55(10H, m), 1.72–1.82(2H, m), 2.37(3H, s), 2.54(2H, t, J=7 Hz), 3.90(2H, t, J=7 Hz), 4.18(2H, q, J=7 Hz), 5.14(2H, s), 6.31(1H, d, J=8 Hz), 6.67(1H, dd, J=8, 2 Hz), 6.96(1H, d, J=2 Hz), 7.19(1H, s), 7.31(1H, s)

PREPARATION EXAMPLE 41-3

In the same manner as in Preparation Example 15-4, (E)-3-(1-(2-chloro-4-(1-pentyloxy)benzyl)-2-methylimidazol-5-yl)-2-(1-pentyl)-2-propenic acid (305 mg) was obtained as a pale-yellow powder from ethyl (E)-3-(1-(2-chloro-4-(1-pentyloxy)benzyl)-2-methylimidazol-5-yl)-2-(1-pentyl)-2-propenate (405 mg).
$^1$H-NMR(DMSO-d$_6$): 0.85–0.87(6H, m), 1.20–1.38(10H, m), 1.62–1.72(2H, m), 2.30(3H, s), 2.42(2H, t, J=7 Hz), 3.94(2H, t, J=7 Hz), 5.21(2H, s), 6.28(1H, d, J=8 Hz), 6.85(1H, dd, J=8, 2 Hz), 7.10(1H, d, J=2 Hz), 7.13(1H, s), 7.22(1H, s)

PREPARATION EXAMPLE 42-1

Diisopropylamine (237 mg) was dissolved in tetrahydrofuran (3 ml), and a solution (1.53 ml) of 1.53M n-butyl lithium in hexane was added under a nitrogen atmosphere while cooling on a dry ice—acetone bath. The mixture was stirred on an ice water bath and a solution of methyl 3-(3-pyridyl)propionate (335 mg) in tetrahydrofuran (1 ml) was added while cooling on a dry ice—acetone bath. The mixture was stirred on a dry ice—acetone bath for 1 hr and a solution of 1-(2-chloro-4-(1-pentyloxy)benzyl)-2-methyl-1H-imidazole-5-carbaldehyde (500 mg) in tetrahydrofuran (1 ml) was added. The mixture was stirred on a dry ice—acetone bath for 1 hr and saturated aqueous ammonium chloride solution was added. The mixture was extracted with ethyl acetate, and the organic layer was washed with saturated brine, dried by the addition of anhydrous magnesium sulfate and concentrated under reduced pressure to give a crude purified product of methyl 3-(1-(2-chloro-4-(1-pentyloxy)benzyl)-2-methylimidazol-5-yl)-3-hydroxy-2-(3-pyridylmethyl)propanate as a brown oil.

PREPARATION EXAMPLE 42-2

The crude purified product of methyl 3-(1-(2-chloro-4-(1-pentyloxy)benzyl)-2-methylimidazol-5-yl)-3-hydroxy-2-(3-pyridylmethyl)propanate was dissolved in dichloromethane (8 ml), and acetic anhydride (0.88 ml) and 4-dimethylaminopyridine (76 mg) were added. The mixture was stirred at room temperature for 14 hr and saturated aqueous sodium hydrogencarbonate solution was added, which was followed by stirring the mixture for 15 min. The reacton mixture was extracted with ethyl acetate, and the organic layer was washed with saturated brine, dried over anhydrous magnesium sulfate, and concentrated under reduced pressure. The residue was dissolved in toluene (8 ml), and 1,8-diazabicyclo[5,4,0]undec-7-ene (0.58 ml) was added. The mixture was heated on an oil bath at 100° C. for 4 hr and saturated aqueous ammonium chloride solution was added, which was followed by extraction with ethyl acetate. The organic layer was washed with saturated brine, dried over anhydrous magnesium sulfate, and concentrated under reduced pressure. The residue was applied to silica gel column chromatography and eluted with chloroform/methanol=100/1. The objective fraction was concentrated under reduced pressure to give methyl (E)-3-(1-(2-chloro-4-(1-pentyloxy)benzyl)-2-methylimidazol-5-yl)-2-(3-pyridylmethyl)-2-propenate (713 mg) as a pale-yellow oil.

$^1$H-NMR(CDCl$_3$): 0.93(3H, t, J=7 Hz), 1.32–1.48(4H, m), 1.72–1.82(2H, m), 2.36(3H, s), 3.70(3H, s), 3.92(2H, t, J=7 Hz), 3.98(2H, s), 5.18(2H, s), 6.30(1H, d, J=8 Hz), 6.69(1H, dd, J=8, 2 Hz), 6.98(1H, d, J=2 Hz), 7.18(1H, dd, J=8, 5 Hz), 7.24(1H, s), 7.44(1H, d, J=8 Hz), 7.51(1H, s), 8.44–8.46(2H, m)

PREPARATION EXAMPLE 42-3

In the same manner as in Preparation Example 15-4, (E)-3-(1-(2-chloro-4-(1-pentyloxy)benzyl)-2-methylimidazol-5-yl)-2-(3-pyridylmethyl)-2-propenic acid (502 mg) was obtained as a brown powder from methyl (E)-3-(1-(2-chloro-4-(1-pentyloxy)benzyl)-2-methylimidazol-5-yl)-2-(3-pyridylmethyl)-2-propenate (695 mg).

$^1$H-NMR(DMSO-d$_6$): 0.88(3H, t, J=7 Hz), 1.27–1.44(4H, m), 1.65–1.74(2H, m), 2.31(3H, s), 3.87(2H, s), 3.96(2H, t, J=7 Hz), 5.27(2H, s), 6.32(1H, d, J=8 Hz), 6.34(1H, dd, J=8, 2 Hz), 7.12(1H, d, J=2 Hz), 7.19(1H, s), 7.27(1H, dd, J=8, 5 Hz), 7.41–7.44(2H, m), 8.36–8.40(2H, m)

PREPARATION EXAMPLE 43-1

In the same manner as in Preparation Example 42-1, a crude purified product of ethyl 3-(1-(2-chloro-4-(1-pentyloxy)benzyl)-2-methylimidazol-5-yl)-3-hydroxy-2-methylpropanate was obtained as a brown oil from 1-(2-chloro-4-(1-pentyloxy)benzyl)-2-methyl-1H-imidazole-5-carbaldehyde (441 mg) and ethyl n-propionate (190 mg).

PREPARATION EXAMPLE 43-2

In the same manner as in Preparation Example 42-2, ethyl (E)-3-(1-(2-chloro-4-(1-pentyloxy)benzyl)-2-methylimidazol-5-yl)-2-methyl-2-propenate (449 mg) was obtained as a pale-yellow oil from the crude purified product of ethyl 3-(1-(2-chloro-4-(1-pentyloxy)benzyl)-2-methylimidazol-5-yl)-3-hydroxy-2-methylpropanate.

$^1$H-NMR(CDCl$_3$): 0.92(3H, t, J=7 Hz), 1.28(3H, t, J=7 Hz), 1.33–1.47(4H, m), 1.72–1.81(2H, m), 2.12(3H, s), 2.38(3H, s), 3.90(2H, t, J=7 Hz), 4.18(2H, q, J=7 Hz), 5.15(2H, s), 6.30(1H, d, J=2 Hz), 6.67(1H, dd, J=8, 2 Hz), 6.96(1H, d, J=2 Hz), 7.26(1H, s), 7.34(1H, s)

PREPARATION EXAMPLE 43-3

In the same manner as in Preparation Example 15-4, (E)-3-(1-(2-chloro-4-(1-pentyloxy)benzyl)-2-methylimidazol-5-yl)-2-methyl-2-propenic acid (253 mg) was obtained as colorless crystals from ethyl (E)-3-(1-(2-chloro-4-(1-pentyloxy)benzyl)-2-methylimidazol-5-yl)-2-methyl-2-propenate (432 mg).

$^1$H-NMR(DMSO-d$_6$): 1.09(3H, t, J=7 Hz), 1.47–1.64(4H, m), 1.85–1.95(2H, m), 2.21(3H, s), 2.52(3H, s), 4.16(2H, t, J=7 Hz), 5.44(2H, s), 6.48(1H, d, J=8 Hz), 7.06(1H, dd, J=8, 2 Hz), 7.32(1H, d, J=2 Hz), 7.41(1H, s), 7.53(1H, s)

PREPARATION EXAMPLE 44-1

In the same manner as in Preparation Example 42-1, a crude purified product of ethyl 3-(4-chloro-1-(2-chloro-4-(1-pentyloxy)benzyl)-2-methylimidazol-5-yl)-3-hydroxy-2-methylpropanate was obtained as a brown oil from 4-chloro-1-(2-chloro-4-(1-pentyloxy)benzyl)-2-methyl-1H-imidazole-5-carbaldehyde (441 mg) and ethyl n-propionate (400 mg).

PREPARATION EXAMPLE 44-2

In the same manner as in Preparation Example 42-2, ethyl (E)-3-(4-chloro-1-(2-chloro-4-(1-pentyloxy)benzyl)-2-methylimidazol-5-yl)-2-methyl-2-propenate (261 mg) was obtained as a pale-yellow oil from the crude purified product of ethyl 3-(4-chloro-1-(2-chloro-4-(1-pentyloxy)benzyl)-2-methylimidazol-5-yl)-3-hydroxy-2-methylpropanate.

$^1$H-NMR(CDCl$_3$): 0.92(3H, t, J=7 Hz), 1.30(3H, t, J=7 Hz), 1.32–1.47(4H, m), 1.70–1.80(2H, m), 1.97(3H, s), 2.31(3H, s), 3.92(2H, t, J=7 Hz), 4.21(2H, q, J=7 Hz), 5.02(2H, s), 6.42(1H, d, J=8 Hz), 6.72(1H, dd, J=8, 2 Hz), 6.95(1H, d, J=2 Hz), 7.06(1H, s)

PREPARATION EXAMPLE 44-3

In the same manner as in Preparation Example 15-4, (E)-3-(4-chloro-1-(2-chloro-4-(1-pentyloxy)benzyl)-2-methylimidazol-5-yl)-2-methyl-2-propenic acid (140 mg) was obtained as colorless crystals from ethyl (E)-3-(4-chloro-1-(2-chloro-4-(1-pentyloxy)benzyl)-2-methylimidazol-5-yl)-2-methyl-2-propenate (250 mg).

$^1$H-NMR(DMSO-d$_6$): 0.88(3H, t, J=7 Hz), 1.25–1.40(4H, m), 1.62–1.72(2H, m), 1.76(3H, s), 2.27(3H, s), 3.95(2H, t, J=7 Hz), 5.12(2H, s), 6.52(1H, d, J=8 Hz), 6.86(1H, dd, J=8, 2 Hz), 7.01(1H, s), 7.06(1H, d, J=2 Hz)

PREPARATION EXAMPLE 45

4-Chloro-1-(2-chloro-4-(1-pentyloxy)benzyl)-2-methyl-1H-imidazole-5-carbaldehyde (400 mg) was dissolved in t-butanol (8 ml), and 2-methyl-2-butene (355 mg) and aqueous sodium dihydrogenphosphate (135 mg) solution (2 ml) were added. To this reaction mixture was added sodium chlorite (356 mg) over 2 min and the mixture was stirred at room temperature for 24 hr. 1N Hydrochloric acid was added under ice-cooling to adjust to pH 4. Water (20 ml) was added and the precipitated crystals were collected by filtration. The crystals were dried by heating under reduced pressure to give 4-chloro-1-(2-chloro-4-(1-pentyloxy)benzyl)-2-methyl-1H-imidazole-5-carboxylic acid (387 mg) as colorless crystals.

$^1$H-NMR(DMSO-$d_6$): 0.88(3H, t, J=7 Hz), 1.27–1.42(4H, m), 1.65–1.75(2H, m), 2.25(3H, s), 3.95(2H, t, J=7 Hz), 5.51(2H, s), 6.32(1H, d, J=8 Hz), 6.86(1H, dd, J=8, 2 Hz), 7.09(1H, d, J=2 Hz)

PREPARATION EXAMPLE 46

4-Chloro-1-(2-chloro-4-(1-pentyloxy)benzyl)-2-methyl-1H-imidazole-5-carbaldehyde (1.05 g) was dissolved in ethanol (10 ml), and sodium borohydride (168 mg) was added under ice-cooling. The mixture was stirred at room temperature for 3 hr. Water was added to the reaction mixture and the mixture was extracted with ethyl acetate. The organic layer was washed with saturated brine, dried over anhydrous magnesium sulfate, and concentrated under reduced pressure. To the residue was added hexane (10 ml) and the precipitated crystals were collected by filtration and dried by heating under reduced pressure to give 4-chloro-1-(2-chloro-4-(1-pentyloxy)benzyl)-5-hydroxymethyl-2-methyl-1H-imidazole (786 mg) as colorless crystals.

$^1$H-NMR(CDCl$_3$): 0.93(3H, t, J=7 Hz), 1.30–1.48(4H, m), 1.72–1.85(2H, m), 2.26(3H, s), 3.91(2H, t, J=7 Hz), 4.50(2H, s), 5.18(2H, s), 6.40(1H, d, J=8 Hz), 6.70(1H, dd, J=8, 2 Hz), 6.96(1H, d, J=2 Hz)

PREPARATION EXAMPLE 47-1

In the same manner as in Preparation Example 9,4-chloro-5-chloromethyl-1-(2-chloro-4-(1-pentyloxy)benzyl)-2-methyl-1H-imidazole (707 mg) was obtained as a brown oil from 4-chloro-1-(2-chloro-4-(1-pentyloxy)benzyl)-5-hydroxymethyl-2-methyl-1H imidazole (611 mg).

$^1$H-NMR(CDCl$_3$): 0.93(3H, t, J=7 Hz), 1.32–1.48(4H, m), 1.73–1.82(2H, m), 2.33(3H, s), 3.92(2H, t, J=7 Hz), 4.48(2H, s), 5.17(2H, s), 6.46(1H, d, J=8 Hz), 6.73(1H, dd, J=8, 2 Hz), 6.97(1H, d, J=2 Hz)

PREPARATION EXAMPLE 47-2

A solution of 4-chloro-5-chloromethyl-1-(2-chloro-4-(1-pentyloxy)benzyl)-2-methyl-1H-imidazole (340 mg) in acetonitrile (3 ml) was added gradually to a mixed solvent of 28% aqueous ammonia (6 ml) and acetonitrile (6 ml) under ice-cooling. The reaction mixture was stirred at room temperature for 1 hr. Saturated aqueous sodium hydrogencarbonate solution was added and the mixture was extracted with ethyl acetate. The organic layer was washed with saturated brine, dried over anhydrous magnesium sulfate, and concentrated under reduced pressure. The residue was applied to silica gel column chromatography and eluted with chloroform/methanol=100/1. The objective fraction was concentrated under reduced pressure to give 5-aminomethyl-4-chloro-1-(2-chloro-4-(1-pentyloxy)benzyl)-2-methyl-1H-imidazole (82 mg) as a pale-brown oil.

$^1$H-NMR(CDCl$_3$): 0.93(3H, t, J=7 Hz), 1.32–1.48(4H, m), 1.73–1.83(2H, m), 2.26(3H, s), 3.70(2H, s), 3.91(2H, t, J=7 Hz), 5.19(2H, s), 6.37(1H, d, J=8 Hz), 6.70(1H, dd, J=8, 2 Hz), 6.96(1H, d, J=2 Hz)

PREPARATION EXAMPLE 48

In the same manner as in Preparation Example 47-2,5-(N-methylamino)methyl-4-chloro-1-(2-chloro-4-(1-pentyloxy)benzyl)-2-methyl-1H-imidazole (85 mg) was obtained as a pale-brown oil from 4-chloro-5-chloromethyl-1-(2-chloro-4-(1-pentyloxy)benzyl)-2-methyl-1H-imidazole (340 mg).

$^1$H-NMR(CDCl$_3$): 0.93(3H, t, J=7 Hz), 1.30–1.45(4H, m), 1.72–1.82(2H, m), 2.25(3H, s), 2.36(3H,s), 3.56(2H, s), 3.91(2H, t, J=7 Hz), 5.19(2H, s), 6.36(1H, d, J=8 Hz), 6.69(1H, dd, J=8, 2 Hz), 6.95(1H, d, J=2 Hz)

PREPARATION EXAMPLE 49-1

4,5-Dibromo-2-ethylimidazole (451.3 g) was dissolved in N,N-dimethylformamide (2.25 L), and potassium carbonate (368 g) was added. (Chloromethyl)methyl ether (200 g) was gradually added dropwise under ice-cooling and the mixture was stirred at room temperature for 2 hr. The reaction mixture was poured into ice-cooled brine and the mixture was extracted with ethyl acetate. The organic layer was washed successively with water and saturated brine, and dried over anhydrous magnesium sulfate. The solvent was evaporated under reduced pressure. Hexane was added to the residue and the mixture was heated and allowed to cool. The precipitated crystals were collected by filtration and dried by heating under reduced pressure to give 4,5-dibromo-2-ethyl-1-(methoxymethyl)imidazole (461.7 g) as brown crystals.

$^1$H-NMR(CDCl$_3$): 1.33(3H, t, J=7 Hz), 2.77(2H, q, J=7 Hz), 3.34(3H, s), 5.23(2H, s)

PREPARATION EXAMPLE 49-2

4,5-Dibromo-2-ethyl-1-(methoxymethyl)imidazole (461.1 g) was dissolved in tetrahydrofuran (2.3 L), and 1.57M n-butyllithium/hexane solution (1.084 L) was gradually added dropwise at −60° C. The reaction mixture was stirred at −60° C. for 30 min. and N,N-dimethylformamide (599 ml) was added dropwise at −60° C. The mixture was stirred at room temperature for 2 hr and poured into ice water. The reaction mixture was extracted with ethyl acetate, and the organic layer was washed successively with water and saturated brine and dried over anhydrous magnesium sulfate. The solvent was evaporated under reduced pressure to give 4-bromo-2-ethyl-1-(methoxymethyl)imidazole-5-carboxyaldehyde (366.2 g) as a brown oil.

$^1$H-NMR(CDCl$_3$): 1.37(3H, t, J=7 Hz), 2.80(2H, q, J=7 Hz), 3.35(3H, s), 5.69(2H, s), 9.72(1H, s)

PREPARATION EXAMPLE 49-3

4-Bromo-2-ethyl-1-(methoxymethyl)imidazole-5-carbaldehyde (365 g) was dissolved in 35% conc. hydrochloric acid (1.8 L), and the mixture was heated at 90° C. for 20 hr. The solvent was evaporated under reduced pressure, and sodium hydrogencarbonate was added to the residue under ice-cooling until the mixture assumed weak alkalinity. The mixture was extracted with chloroform, and the organic layer was dried over anhydrous magnesium sulfate. The solvent was evaporated under reduced pressure and diisopropyl ether was added to the residue. The mixture was heated and allowed to cool. The precipitated crystals were collected by filtration and dried by heating under reduced pressure to give 4-chloro-2-ethylimidazole-5-carbaldehyde (211.5 g) as brown crystals.

$^1$H-NMR(CDCl$_3$): 1.37(3H, t, J=7 Hz), 2.85(2H, q, J=7 Hz), 9.63(1H, s), 11.30(1H, brs)

EXAMPLE 1

To a suspension of (E)-3-(4-chloro-1-(2-chloro-4-(2-furyl)benzyl)-2-methylimidazol-5-yl)-2-propenic acid (155 mg) in N,N-dimethylformamide (0.8 ml) was added 1,1'-carbonyldiimidazole (101 mg) at room temperature, and the mixture was stirred for 1 hr. Thereto were added (4-methylbenzene)sulfonamide (106 mg) and 1,8-diazabicyclo[5.4.0]-7-undecene (96 mg), and the mixture was stirred at 50° C. for 5 hr. The reaction mixture was ice-cooled and 1N hydrochloric acid (1.7 ml) was added dropwise to neutralize the solution. Water (4 ml) was added and the precipitate was collected by filtration. This crude product was recrystallized from acetone—water to give (E)-3-(4-chloro-1-(2-chloro-4-(2-furyl)benzyl)-2-methylimidazol-5-yl)-N-((4-methylbenzene)-sulfonyl)-2-propenamide (152 mg) as a pale-yellow powder.

$^1$H-NMR(CDCl$_3$): 2.34(3H, s), 2.40(3H, s), 5.17(2H, s), 6.38(1H, d, J=8 Hz), 6.49(1H, dd, J=3 and 2 Hz), 6.53(1H, d, J=16 Hz), 6.68(1H, d, J=3 Hz), 7.31(2H, d, J=8 Hz), 7.35(1H, d, J=16 Hz), 7.43(1H, dd, J=8 and 2 Hz), 7.49(1H, d, J=2 Hz), 7.74(1H, d, J=2 Hz), 7.92(2H, d, J=8 Hz). Mass(ESI): m/e 528(M−H)−. m.p. 242–243° C.

EXAMPLE 2

In the same manner as in Example 1, (2E)-3-(4-chloro-1-(2-chloro-4-(2-furyl)benzyl)-2-methylimidazol-5-yl)-N-(((E)-2-phenylethenyl)sulfonyl)-2-propenamide (159 mg) was obtained as a pale-yellow powder from (E)-3-(4-chloro-1-(2-chloro-4-(2-furyl)benzyl)-2-methylimidazol-5-yl)-2-propenic acid (148 mg) and (E)-(2-phenylethene)sulfonamide (108 mg).

$^1$H-NMR(DMSO-d$_6$): 2.31(3H, s), 5.39(2H, s), 6.55(1H, d, J=8 Hz), 6.61(1H, dd, J=3 and 2 Hz), 6.69(1H, d, J=16 Hz), 7.06(1H, d, J=3 Hz), 7.26(1H, d, J=16 Hz), 7.35–7.50 (4H, m), 7.56(1H, d, J=16 Hz), 7.59(1H, dd, J=8 and 2 Hz), 7.67–7.77(2H, m), 7.78(1H, d, J=2 Hz), 7.86(1H, d, J=2 Hz), 12.07(1H, br s). Mass(ESI): m/e 540(M−H)−. m.p. 227–228° C.

EXAMPLE 3

In the same manner as in Example 1, (E)-3-(4-chloro-1-(2-chloro-4-(2-thienyl)benzyl)-2-methylimidazol-5-yl)-N-((4-methylbenzene)sulfonyl)-2-propenamide was obtained as colorless crystals (80 mg) from (E)-3-(4-chloro-1-(2-chloro-4-(2-thienyl)benzyl)-2-methylimidazol-5-yl)-2-propenic acid (100 mg) and (4-methylbenzene)sulfonamide (65 mg).

$^1$H-NMR(CDCl$_3$): 2.34(3H, s), 2.40(3H, s), 5.16(2H, s), 6.37(1H, d, J=8 Hz), 6.54(1H, d, J=16 Hz), 7.06–7.11(1H, m), 7.26–7.40(6H, m), 7.65(1H, d, J=2 Hz), 7.92(2H, d, J=8 Hz). Mass(ESI): m/z 544(M−1). m.p. 235–237° C.

EXAMPLE 4

In the same manner as in Example 1, (2E)-3-(4-chloro-1-(2-chloro-4-(2-thienyl)benzyl)-2-methylimidazol-5-yl)-N-(((E)-2-phenylethenyl)sulfonyl)-2-propenamide was obtained as colorless crystals (105 mg) from (E)-3-(4-chloro-1-(2-chloro-4-(2-thienyl)benzyl)-2-methylimidazol-5-yl)-2-propenic acid (100 mg) and (E)-(2-phenylethene)sulfonamide (70 mg).

$^1$H-NMR(DMSO-d$_6$): 2.32(3H, s), 5.39(2H, s), 6.52(1H, d, J=8 Hz), 6.69(1H, d, J=16 Hz), 7.11–7.17(1H, m), 7.26 (1H, d, J=16 Hz), 7.36–7.49(4H, m), 7.50–7.63(4H, m), 7.72(2H, dd, J=2, 8 Hz), 7.84(1H, d, J=2 Hz). Mass(ESI): m/z 556(M−1). m.p. 246–248° C.

EXAMPLE 5

In the same manner as in Example 1, (E)-3-(4-chloro-1-(2-chloro-4-(phenylethynyl)benzyl)-2-methylimidazol-5-yl)-N-((4-methylbenzene)sulfonyl)-2-propenamide was obtained as thin yellow crystals (123 mg) from (E)-3-(4-chloro-1-(2-chloro-4(phenylethynyl)benzyl)- 2-methylimidazol-5-yl)-2-propenic acid (130 mg) and (4-methylbenzene)sulfonamide (81 mg).

$^1$H-NMR(CDCl$_3$): 2.32(3H, s), 2.41(3H, s), 5.17(2H, s), 6.34(1H, d, J=8 Hz), 6.56(1H, d, J=16 Hz), 7.27–7.40(7H, m), 7.48–7.55(2H, m), 7.60(1H, d, J=2 Hz), 7.93(2H, d, J=8 Hz). Mass(ESI): m/z 562(M−1). m.p. 239–241° C.

EXAMPLE 6

In the same manner as in Example 1, (2E)-3-(4-chloro-1-(2-chloro-4-(phenylethynyl)benzyl)-2-methylimidazol-5-yl)-N-(((E)-2-phenylethenyl)sulfonyl)-2-propenamide was obtained as thin ocher crystals (101 mg) from (E)-3-(4-chloro-1-(2-chloro-4-(phenylethynyl)benzyl)-2-methylimidazol-5-yl)-2-propenic acid (130 mg) and (E)-(2-phenylethene)sulfonamide (87 mg).

$^1$H-NMR(CDCl$_3$): 2.34(3H, s), 5.20(2H, s), 6.39(1H, d, J=8 Hz), 6.61(1H, d, J=16 Hz), 7.05(1H, d, J=16 Hz), 7.30(1H, dd, J=2, 8 Hz), 7.33–7.44(7H, m), 7.46–7.55(4H, m), 7.60(1H, d, J=2 Hz), 7.71(1H, d, J=16 Hz). Mass(ESI): m/z 574(M−1). m.p. 220–222° C.

EXAMPLE 7

In the same manner as in Example 1, (E)-3-(1-(4-bromo-2-chlorobenzyl)-4-chloro-2-methylimidazol-5-yl)-N-((4-methylbenzene)sulfonyl)-2-propenamide (162 mg) was obtained as colorless crystals from (E)-3-(1-(4-bromo-2-chlorobenzyl)-4-chloro-2-methylimidazol-5-yl)-2-propenic acid (150 mg) and (4-methylbenzene)sulfonamide (99 mg).

$^1$H-NMR(CDCl$_3$): 2.31(3H, s), 2.43(3H, s), 5.10(2H, s), 6.23(1H, d, J=8 Hz), 6.58(1H, d, J=15 Hz), 7.25–7.33(4H, m), 7.58(1H, d, J=2 Hz), 7.92(2H, d, J=8 Hz). Mass(ESI): m/z 542(M−H)−. m.p. 233–235° C.

EXAMPLE 8

In the same manner as in Example 1, (E)-3-(1-(4-bromo-2-chlorobenzyl)-4-chloro-2-methylimidazol-5-yl)-N-(((E)-2-phenylethenyl)sulfonyl)-2-propenamide (172 mg) was obtained as colorless crystals from (E)-3-(1-(4-bromo-2-chlorobenzyl)-4-chloro-2-methylimidazol-5-yl)-2-propenic acid (168 mg) and (E)(2-phenylethene)sulfonamide (118 mg).

$^1$H-NMR(CDCl$_3$-CD$_3$OD): 2.32(3H, s), 5.15(2H, s), 6.28 (1H, d, J=8 Hz), 6.70(1H, d, J=15 Hz), 7.08(1H, d, J=15 Hz), 7.31–7.42(5H, m), 7.49–7.53(2H, m), 7.62(1H, d, J=2 Hz), 7.69(1H, d, J=15 Hz). Mass(ESI): m/z 554(M−H)−. m.p. 250–251° C.

EXAMPLE 9

In the same manner as in Example 1, (E)-3-[4-chloro-1-(2-chloro-4-phenylbenzyl)-2-methylimidazol-5-yl]-N-(1-pentanesulfonyl)-2-propenamide (134 mg) was obtained as colorless crystals from (E)-3-[4-chloro-1-(2-chloro-4-phenylbenzyl)-2-methylimidazol-5-yl]-2-propenic acid (150 mg).

$^1$H-NMR(CDCl$_3$): 0.87(3H, t, J=8 Hz), 1.24–1.45(4H, m), 1.75–1.89(2H, m), 2.40(3H, s), 3.38–3.47(2H, m), 5.26 (2H, s), 6.50 (1H, d, J=8 Hz), 6.57(1H, d, J=15 Hz), 7.35–7.58(7H, m), 7.68(1H, d, J=2 Hz), 8.18(1H, br s). Mass(ESI): m/z 520(M+1). m.p. 203–204° C.

EXAMPLE 10

In the same manner as in Example 1, (E)-N-benzenesulfonyl-3-[4-chloro-1-(2-chloro-4-phenylbenzyl)-2-methylimidazol-5-yl]-2-propenamide (141 mg) was obtained as colorless crystals from (E)-3-[4-chloro-1-(2-chloro-4-phenylbenzyl)-2-methylimidazol-5-yl]-2-propenic acid (150 mg).

$^1$H-NMR(CDCl$_3$): 2.36(3H, s), 5.20(2H, s), 6.43(1H, d, J=8 Hz), 6.57(1H, d, J=15 Hz), 7.31–7.55(9H, m), 7.59(1H, d, J=8 Hz), 7.64(1H, d, J=2 Hz), 8.05(2H, d, J=8 Hz), 8.54(1H, br s). Mass(ESI): m/z 526(M+1). m.p. 245–247° C.

EXAMPLE 11

In the same manner as in Example 1, (E)-3-[4-chloro-1-(2-chloro-4-phenylbenzyl)-2-methylimidazol-5-yl]-N-((4-methylbenzene)sulfonyl)-2-propenamide (137 mg) was obtained as colorless crystals from (E)-3-[4-chloro-1-(2-chloro-4-phenylbenzyl)-2-methylimidazol-5-yl]-2-propenic acid (150 mg).

$^1$H-NMR(CDCl$_3$): 2.35(3H, s), 2.40(3H, s), 5.19(2H, s), 6.43(1H, d, J=8 Hz), 6.57(1H, d, J=15 Hz), 7.24–7.55(8H, m), 7.65(1H, d, J=1 Hz), 7.92(2H, d, J=8 Hz), 8.41(1H, br s). Mass(ESI): m/z 540(M+1). m.p. 229–232° C.

EXAMPLE 12

In the same manner as in Example 1, (E)-3-(4-chloro-1-(2-chloro-4-phenylbenzyl)-2-methylimidazol-5-yl)-N-(((E)-2-phenylethenyl)sulfonyl)-2-propenamide (132 mg) was obtained as colorless crystals from (E)-3-(4-chloro-1-(2-chloro-4-phenylbenzyl)-2-methylimidazol-5-yl)-2-propenic acid (150 mg) and (E)-(2-phenylethene)sulfonamide (106 mg).

$^1$H-NMR(CDCl$_3$): 2.37(3H, s), 5.22(2H, s), 6.47(1H, d, J=8 Hz), 6.57(1H, d, J=15 Hz), 7.03(1H, d, J=15 Hz), 7.37–7.54(12H, m), 7.65(1H, s), 7.71(1H, d, J=15 Hz). Mass(ESI): m/z 554(M+H)+. m.p. 240–241° C.

EXAMPLE 13

In the same manner as in Example 1, (E)-3-(4-chloro-1-(2-chloro-4-phenylbenzyl)-2-methylimidazol-5-yl)-N-((5-chloro-2-thienyl)sulfonyl)-2-propenamide (126 mg) was obtained as colorless crystals from (E)-3-(4-chloro-1-(2-chloro-4-phenylbenzyl)-2-methylimidazol-5-yl)-2-propenic acid (150 mg) and 5-chlorothiophene-2-sulfonamide (115 mg).

$^1$H-NMR(CDCl$_3$): 2.37(3H, s), 5.21(2H, s), 6.46(1H, d, J=8 Hz), 6.60(1H, d, J=15 Hz), 6.90(1H, d, J=4 Hz), 7.37–7.53(7H, m), 7.64–7.66(2H, m). Mass(ESI): m/z 566 (M+H)+. m.p. 229–233° C.

EXAMPLE 14

In the same manner as in Example 1, (E)-N-((5-bromo-2-thienyl)sulfonyl)-3-(4-chloro-1-(2-chloro-4-phenylbenzyl)-2-methylimidazol-5-yl)-2-propenamide (155 mg) was obtained as colorless crystals from (E)-3-(4-chloro-1-(2-chloro-4-phenylbenzyl)-2-methylimidazol-5-yl)-2-propenic acid (150 mg) and 5-bromothiophene-2-sulfonamide (141 mg).

$^1$H-NMR(CDCl$_3$): 2.37(3H, s), 5.21(2H, s), 6.46(1H, d, J=8 Hz), 6.59(1H, d, J=15 Hz), 7.04(1H, d, J=4 Hz), 7.36–7.55(7H, m), 7.61(1H, d, J=4 Hz), 7.66(1H, d, J=2 Hz). Mass(ESI): m/z 612(M+H)+. m.p. 234–235° C.

EXAMPLE 15

In the same manner as in Example 1, (E)-3-(4-chloro-1-(2-chloro-4-(1-propoxy)benzyl)-2-methylimidazol-5-yl)-N-((4-methylbenzene)sulfonyl)-2-propenamide (155 mg) was obtained as colorless crystals from (E)-3-(4-chloro-1-(2-chloro-4-(1-propoxy)benzyl)-2-methylimidazol-5-yl)-2-propenic acid (145 mg) and (4-methylbenzene)sulfonamide (96 mg).

$^1$H-NMR(CDCl$_3$-CD$_3$OD): 1.02(3H, t, J=7 Hz), 1.73–1.85(2H, m), 2.30(3H, s), 2.41(3H, s), 3.88(2H, t, J=7 Hz), 5.10(2H, s), 6.27(1H, d, J=8 Hz), 6.64(1H, d, J=15 Hz), 6.68(1H, dd, J=8, 2 Hz), 6.97(1H, d, J=2 Hz), 7.27–7.33(3H, m), 7.92(2H, d, J=8 Hz). Mass(ESI): m/z 520(M−H)−. m.p. 226–228° C.

EXAMPLE 16

In the same manner as in Example 1, (E)-3-(4-chloro-1-(2-chloro-4-(1-propoxy)benzyl)-2-methylimidazol-5-yl)-N-(((E)-2-phenylethenyl)sulfonyl)-2-propenamide (164 mg) was obtained as colorless crystals from (E)-3-(4-chloro-1-(2-chloro-4-(1-propoxy)benzyl)-2-methylimidazol-5-yl)-2-propenic acid (143 mg) and (E)-(2-phenylethene)sulfonamide (106 mg).

$^1$H-NMR(CDCl$_3$-CD$_3$OD): 1.02(3H, t, J=7 Hz), 1.73–1.85(2H, m), 2.32(3H, s), 3.88(2H, t, J=7 Hz), 5.15 (2H, s), 6.33(1H, d, J=8 Hz), 6.69(1H, d, J=15 Hz), 6.70(1H, dd, J=8, 2 Hz), 6.98(1H, d, J=2 Hz), 7.09(1H, d, J=15 Hz), 7.35–7.42(4H, m), 7.50–7.54(2H, m), 7.68(1H, d, J=15 Hz). Mass(ESI): m/z 532(M−H)−. m.p. 199–201° C.

EXAMPLE 17

In the same manner as in Example 1, (E)-3-(4-chloro-1-(2-chloro-4-(1-pentyloxy)benzyl)-2-methylimidazol-5-yl)-N-((4-methylbenzene)sulfonyl)-2-propenamide was obtained as colorless crystals (60 mg) from (E)-3-(4-chloro-1-(2-chloro-4-(1-pentyloxy)benzyl)-2-methylimidazol-5-yl)-2-propenic acid (100 mg) and (4-methylbenzene)sulfonamide (65 mg).

$^1$H-NMR(CDCl$_3$): 0.93(3H, t, J=7 Hz), 1.30–1.50(4H, m), 1.70–1.84(2H, m), 2.32(3H, s), 2.42(3H, s), 3.90(2H, t, J=7 Hz), 5.09(2H, s), 6.27(1H, d, J=8 Hz), 6.53(1H, d, J=16

Hz), 6.67(1H, dd, J=2, 8 Hz), 6.96(1H, d, J=2 Hz), 7.28–7.39(3H, m), 7.93(2H, d, J=8 Hz). Mass(ESI): m/z 548(M−1). m.p. 195–197° C.

EXAMPLE 18

In the same manner as in Example 1, (E)-3-(4-chloro-1-(2-chloro-4-(1-pentyloxy)benzyl)-2-methylimidazol-5-yl)-N-(((E)-2-phenylethenyl)sulfonyl)-2-propenamide was obtained as colorless crystals (84 mg) from (E)-3-(4-chloro-1-(2-chloro-4-(1-pentyloxy)benzyl)-2-methylimidazol-5-yl)-2-propenic acid (100 mg) and (E)-(2-phenylethene)sulfonamide (69 mg).

$^1$H-NMR(CDCl$_3$): 0.92(3H, t, J=7 Hz), 1.30–1.49(4H, m), 1.69–1.72(2H, m), 2.34(3H, s), 3.90(2H, t, J=7 Hz), 5.13(2H, s), 6.32(1H, d, J=8 Hz), 6.56(1H, d, J=16 Hz), 6.68(1H, dd, J=2, 8 Hz), 6.96(1H, d, J=2 Hz), 7.06(1H, d, J=16 Hz), 7.35–7.56(6H, m), 7.72(1H, d, J=16 Hz). Mass(ESI): m/z 560(M−1). m.p. 196–199° C.

EXAMPLE 19

In the same manner as in Example 1, (E)-3-(4-chloro-1-(2-chloro-4-((cyclopentyl)methyloxy)benzyl)-2-methylimidazol-5-yl)-N-(1-pentanesulfonyl)-2-propenamide (82 mg) was obtained as a white powder from (E)-3-(4-chloro-1-(2-chloro-4-((cyclopentyl)-methyloxy)benzyl)-2-methylimidazol-5-yl)-2-propenic acid (164 mg) and 1-pentanesulfonamide (90 mg).

$^1$H-NMR(CDCl$_3$): 0.90(3H, t, J=7 Hz), 1.25–1.92(14H, m), 2.34(1H, sept, J=7 Hz), 2.37(3H, s), 3.38–3.50(2H, m), 3.80(2H, d, J=7 Hz), 5.16(2H, s), 6.34(1H, d, J=8 Hz), 6.51(1H, d, J=15 Hz), 6.72(1H, dd, J=8 and 2 Hz), 7.00(1H, d, J=2 Hz), 7.44(1H, d, J=16 Hz). Mass(ESI): m/e 540 (M−H)−. m.p. 177–178° C.

EXAMPLE 20

In the same manner as in Example 1, (E)-3-(4-chloro-1-(2-chloro-4-((cyclopentyl)methyloxy)benzyl)-2-methylimidazol-5-yl)-N-((4-methylbenzene)sulfonyl)-2-propenamide (135 mg) was obtained as a white powder from (E)-3-(4-chloro-1-(2-chloro-4-((cyclopentyl)methyloxy)benzyl)-2-methylimidazol-5-yl)-2-propenic acid (163 mg) and (4-methylbenzene)sulfonamide (106 mg).

$^1$H-NMR(CDCl$_3$): 1.25–1.92(8H, m), 2.32(3H, s), 2.33 (1H, sept, J=7 Hz), 2.42(3H, s), 3.78(2H, d, J=7 Hz), 5.09(2H, s), 6.27(1H, d, J=8 Hz), 6.52(1H, d, J=16 Hz), 6.68(1H, dd, J=8 and 2 Hz), 6.97(1H, d, J=2 Hz), 7.32(2H, d, J=8 Hz), 7.34(1H, d, J=16 Hz), 7.94(2H, d, J=8 Hz). Mass(ESI): m/e 560(M−H)−. m.p. 217–218° C.

EXAMPLE 21

In the same manner as in Example 1, (2E)-3-(4-chloro-1-(2-chloro-4-((cyclopentyl)methyloxy)benzyl)-2-methylimidazol-5-yl)-N-(((E)-2-phenylethenyl)sulfonyl)-2-propenamide (128 mg) was obtained as a white powder from (E)-3-(4-chloro-1-(2-chloro-4-((cyclopentyl)methyloxy)benzyl)-2-methylimidazol-5-yl)-2-propenic acid (164 mg) and (E)-(2-phenylethene)sulfonamide (99 mg).

$^1$H-NMR(CDCl$_3$): 1.23–1.92(8H, m), 2.32(1H, sept, J=7 Hz), 2.33(3H, s), 3.77(2H, d, J=7 Hz), 5.12(2H, s), 6.32(1H, d, J=8 Hz), 6.60(1H, d, J=16 Hz), 6.68(1H, dd, J=8 and 2 Hz), 6.96(1H, d, J=2 Hz), 7.08(1H, d, J=16 Hz), 7.33–7.56 (5H, m), 7.40(1H, d, J=16 Hz), 7.70(1H, d, J=16 Hz). Mass(ESI): m/e 572(M−H)−. m.p. 200–201° C.

EXAMPLE 22

In the same manner as in Example 1, (E)-3-(4-chloro-1-(2-chloro-4-((cyclohexyl)methyloxy)benzyl)-2-methylimidazol-5-yl)-N-((4-methylbenzene)sulfonyl)-2-propenamide was obtained as colorless crystals (61 mg) from (E)-3-(4-chloro-1-(2-chloro-4-((cyclohexyl)methyloxy)benzyl)-2-methylimidazol-5-yl)-2-propenic acid (85 mg) and (4-methylbenzene)sulfonamide (52 mg).

$^1$H-NMR(CDCl$_3$): 0.95–1.89(11H, m), 2.32(3H, s), 2.42 (3H, s), 3.70(2H, d, J=7 Hz), 5.10(2H, s), 6.22(1H, d, J=8 Hz), 6.50(1H, d, J=16 Hz), 6.67(1H, dd, J=2, 8 Hz), 6.97 (1H, d, J=2 Hz), 7.30–7.38(3H, m), 7.94(2H, d, J=8 Hz). Mass(ESI): m/z 574(M−1). m.p. 214–216° C.

EXAMPLE 23

In the same manner as in Example 1, (2E)-3-(4-chloro-1-(2-chloro-4-((cyclohexyl)methyloxy)benzyl)-2-methylimidazol-5-yl)-N-(((E)-2-phenylethenyl)sulfonyl)-2-propenamide was obtained as colorless crystals (63 mg) from (E)-3-(4-chloro-1-(2-chloro-4-((cyclohexyl)methyloxy)benzyl)-2-methylimidazol-5-yl)-2-propenic acid (85 mg) and (E)-(2-phenylethene)sulfonamide (55 mg).

$^1$H-NMR(CDCl$_3$): 0.95–1.37(6H, m), 1.65–1.88(5H, m), 2.35(3H, s), 3.70(2H, d, J=7 Hz), 5.13(2H, s), 6.31(1H, d, J=8 Hz), 6.54(1H, d, J=16 Hz), 6.68(1H, dd, J=2, 8 Hz), 6.98(1H, d, J=2 Hz), 7.06(1H, d, J=16 Hz), 7.37–7.45(4H, m), 7.49–7.54(2H, m), 7.72(1H, d, J=16 Hz). Mass(ESI): m/z 586(M−1). m.p. 210–212° C.

EXAMPLE 24

In the same manner as in Example 1, (E)-3-(1-(4-benzyloxy-2-chlorobenzyl)-4-chloro-2-methylimidazol-5-yl)-N-((4-methylbenzene)sulfonyl)-2-propenamide was obtained as colorless crystals (83 mg) from (E)-3-(1-(4-benzyloxy-2-chlorobenzyl)-4-chloro-2-methylimidazol-5-yl)-2-propenic acid (90 mg) and (4-methylbenzene)sulfonamide (55 mg).

$^1$H-NMR(CDCl$_3$): 2.32(3H, s), 2.42(3H, s), 5.03(2H, s), 5.10(2H, s), 6.29(1H, d, J=8 Hz), 6.51(1H, d, J=16 Hz), 6.75(1H, dd, J=2, 8 Hz), 7.06(1H, d, J=2 Hz), 7.29–7.44(8H, m), 7.95(2H, d, J=8 Hz). Mass (ESI): m/z 568 (M−1) m.p. 226–228° C.

EXAMPLE 25

In the same manner as in Example 1, (E)-3-(1-(4-benzyloxy-2-chlorobenzyl)-4-chloro-2-methylimidazol-5-yl)-N-(((E)-2-phenylethenyl)sulfonyl)-2-propenamide was obtained as colorless crystals (73 mg) from (E)-3-(1-(4-benzyloxy-2-chlorobenzyl)-4-chloro-2-methylimidazol-5-yl)-2-propenic acid (90 mg) and (E)-(2-phenylethene)sulfonamide (59 mg).

$^1$H-NMR(CDCl$_3$): 2.34(3H, s), 5.02(2H, s), 5.14(2H, s), 6.34(1H, d, J=8 Hz), 6.56(1H, d, J=16 Hz), 6.77(1H, dd, J=2, 8 Hz), 7.02–7.10(2H, m), 7.31–7.55(11H, m), 7.73(1H, d, J=16 Hz). Mass(ESI): m/z 580(M−1). m.p. 225–227° C.

EXAMPLE 26

In the same manner as in Example 1, (E)-3-(4-chloro-1-(2-chloro-4-(methylthio)benzyl)-2-methylimidazol-5-yl)-N-((4-methylbenzene)sulfonyl)-2-propenamide was obtained as colorless crystals (83 mg) from (E)-3-(4-chloro-1-(2- chloro-4-(methylthio)benzyl)-2-methylimidazol-5-yl)-2-propenic acid (90 mg) and (4-methylbenzene)sulfonamide (65 mg).

$^1$H-NMR(CDCl$_3$): 2.32(3H, s), 2.42(3H, s), 2.47(3H, s), 5.11(2H, s), 6.26(1H, d, J=8 Hz), 6.52(1H, d, J=16 Hz), 7.00(1H, dd, J=2, 8 Hz), 7.26–7.36(4H, m), 7.94(2H, d, J=8 Hz). Mass(ESI): m/z 508(M–1). m.p. 228–230° C.

EXAMPLE 27

In the same manner as in Example 1, (E)-3-(4-chloro-1-(2-chloro-4-(methylthio)benzyl)-2-methylimidazol-5-yl)-N-(((E)-2-phenylethenyl)sulfonyl)-2-propenamide was obtained as colorless crystals (97 mg) from (E)-3-(4-chloro-1-(2-chloro-4-(methylthio)benzyl)-2-methylimidazol-5-yl)-2-propenic acid (90 mg) and (E)-(2-phenylethene)sulfonamide (69 mg).

$^1$H-NMR(CDCl$_3$): 2.34(3H, s), 2.46(3H, s), 5.15(2H, s), 6.31(1H, d, J=8 Hz), 6.57(1H, d, J=16 Hz), 7.00(1H, d, J=2 Hz), 7.05(1H, d, J=16 Hz), 7.29(1H, d, J=2 Hz), 7.35–7.45 (4H, m), 7.49–7.55(2H, m), 7.72(1H, d, J=16 Hz). Mass (ESI): m/z 520(M–1). m.p. 237–238° C.

EXAMPLE 28

In the same manner as in Example 1, (E)-3-(4-chloro-1-(2-chloro-4-(trifluoromethyl)benzyl)-2-methylimidazol-5-yl)-N-((4-methylbenzene)sulfonyl)-2-propenamide was obtained as thin yellow crystals (14 mg) from (E)-3-(4-chloro-1-(2-chloro-4-(trifluoromethyl)benzyl)-2-methylimidazol-5-yl)-2-propenic acid (30 mg) and (4-methylbenzene)sulfonamide (20 mg).

$^1$H-NMR(CDCl$_3$): 2.33(3H, s), 2.42(3H, s), 5.20(2H, s), 6.48(1H, d, J=8 Hz), 6.60(1H, d, J=16 Hz), 7.23–7.35(3H, m), 7.44(1H, d, J=8 Hz), 7.72(1H, s), 7.92(2H, d, J=8 Hz). Mass(ESI): m/z 530(M–1). m.p. 223–225° C.

EXAMPLE 29

In the same manner as in Example 1, (E)-3-(4-chloro-1-(2-chloro-4-(trifluoromethyl)benzyl)-2-methylimidazol-5-yl)-N-(((E)-2-phenylethenyl)sulfonyl)-2-propenamide was obtained as colorless crystals (90 mg) from (E)-3-(4-chloro-1-(2-chloro-4-(trifluoromethyl)benzyl)-2-methylimidazol-5-yl)-2-propenic acid (100 mg) and (E)-(2-phenylethene)sulfonamide (72 mg).

$^1$H-NMR(DMSO-d$_6$): 2.30(3H, s), 5.48(2H, s), 6.63–6.75 (2H, m), 7.24(1H, d, J=16 Hz), 7.37–7.51(4H, m), 7.57(1H, d, J=16 Hz), 7.66(1H, d, J=8 Hz), 7.73(2H, d, J=8 Hz), 7.99(1H, s). Mass(ESI): m/z 542(M–1). m.p. 261–263° C.

EXAMPLE 30

In the same manner as in Example 1, (E)-3-(4-chloro-1-(2-chloro-4-(phenoxymethyl)benzyl)-2-methylimidazol-5-yl)-N-((4-methylbenzene)sulfonyl)-2-propenamide (207 mg) was obtained as a white powder from (E)-3-(4-chloro-1-(2-chloro-4-(phenoxymethyl)benzyl)-2-methylimidazol-5-yl)-2-propenic acid (191 mg) and (4-methylbenzene)sulfonamide (118 mg).

$^1$H-NMR(CDCl$_3$): 2.32(3H, s), 2.42(3H, s), 5.02(2H, s), 5.16(2H, s), 6.38(1H, d, J=8 Hz), 6.54(1H, d, J=15 Hz), 6.89–7.04(3H, m), 7.18–7.38(6H, m), 7.54(1H, d, J=2 Hz), 7.93(2H, d, J=8 Hz). Mass(ESI): m/e 568(M–H)–. m.p. 236–237° C.

EXAMPLE 31

In the same manner as in Example 1, (E)-3-(4-chloro-1-(2-chloro-4-(phenoxymethyl)benzyl)-2-methylimidazol-5-yl)-N-(((E)-2-phenylethenyl)sulfonyl)-2-propenamide (219 mg) was obtained as a white powder from (E)-3-(4-chloro-1-(2-chloro-4-(phenoxymethyl)benzyl)-2-methylimidazol-5-yl)-2-propenic acid (189 mg) and (E)-(2-phenylethene)sulfonamide (128 mg).

$^1$H-NMR(CDCl$_3$): 2.30(3H, s), 5.07(2H, s), 5.39(2H, s), 6.50(1H, d, J=8 Hz), 6.70(1H, d, J=16 Hz), 6.88–7.02(3H, m), 7.22(1H, d, J=16 Hz), 7.26–7.48(7H, m), 7.56(1H, d, J=16 Hz), 7.62(1H, d, J=2 Hz), 7.68–7.80(2H, m), 12.08 (1H, br s). Mass(ESI): m/e 580(M–H)–. m.p. 202–203° C.

EXAMPLE 32

In the same manner as in Example 1, (E)-3-(4-chloro-1-(2-chloro-4-nitrobenzyl)-2-methylimidazol-5-yl)-N-((4-methylbenzene)sulfonyl)-2-propenamide (63 mg) was obtained as pale-yellow crystals from (E)-3-(4-chloro-1-(2-chloro-4-nitrobenzyl)-2-methylimidazol-5-yl)-2-propenic acid (105 mg) and (4-methylbenzene)sulfonamide (76 mg).

$^1$H-NMR(CDCl$_3$-CD$_3$OD): 2.32(3H, s), 2.41(3H, s), 5.24 (2H, s), 6.55(1H, d, J=8 Hz), 6.68(1H, d, J=15 Hz), 7.22(1H, d, J=15 Hz), 7.30(2H, d, J=8 Hz), 7.90(2H, d, J=8 Hz), 8.03(1H, dd, J=8, 2 Hz), 8.33(1H, d, J=2 Hz). Mass(ESI): m/z 507(M–H)–. m.p. 241–243° C.

EXAMPLE 33

In the same manner as in Example 1, (E)-3-(4-chloro-1-(2-chloro-4-nitrobenzyl)-2-methylimidazol-5-yl)-N-(((E)-2-phenylethenyl)sulfonyl)-2-propenamide (78 mg) was obtained as pale-yellow crystals from (E)-3-(4-chloro-1-(2-chloro-4-nitrobenzyl)-2-methylimidazol-5-yl)-2-propenic acid (105 mg) and (E)-(2-phenylethene)sulfonamide (81 mg).

$^1$H-NMR(CDCl$_3$-CD$_3$OD): 2.34(3H, s), 5.29(2H, s), 6.59 (1H, d, J=8 Hz), 6.73(1H, d, J=15 Hz), 7.06(1H, d, J=15 Hz), 7.30(1H, t, J=8 Hz), 7.37–7.45(3H, m), 7.50–7.52(2H, m), 7.68(1H, d, J=15 Hz), 8.05(1H, dd, J=8, 2 Hz), 8.34(1H, d, J=2 Hz). Mass(ESI): m/z 519(M–H)–. m.p. 199–201° C.

EXAMPLE 34

In the same manner as in Example 1, (E)-3-(4-chloro-1-(2-chloro-4-((E)-2-phenylethenyl)benzyl)-2-methylimidazol-5-yl)-N-((4-methylbenzene)sulfonyl)-2-propenamide was obtained as thin yellow crystals (81 mg) from (E)-3-(4-chloro-1-(2-chloro-4-((E)-2-phenylethenyl)benzyl)-2-methylimidazol-5-yl)-2-propenic acid (150 mg) and (4-methylbenzene)sulfonamide (93 mg).

$^1$H-NMR(CDCl$_3$): 2.33(3H, s), 2.39(3H, s), 5.15(2H, s), 6.35(1H, d, J=8 Hz), 6.54(1H, d, J=16 Hz), 6.97(1H, d, J=16 Hz), 7.08(1H, d, J=16 Hz), 7.21–7.41(7H, m), 7.50(2H, d, J=8 Hz), 7.55(1H, d, J=2 Hz), 7.92(1H, d, J=8 Hz). Mass (ESI): m/z 564(M–1). m.p. 237–239° C.

EXAMPLE 35

In the same manner as in Example 1, (E)-3-(4-chloro-1-(2-chloro-4-((E)-2-phenylethenyl)benzyl)-2-methylimidazol-5-yl)-N-(((E)-2-phenylethenyl)sulfonyl)-2-propenamide was obtained as colorless crystals (86 mg) from (E)-3-(4-chloro-1-(2-chloro-4-((E)-2-phenylethenyl)benzyl)-2-methylimidazol-5-yl)-2-propenic acid (150 mg) and (E)-(2-phenylethene)sulfonamide (100 mg).

$^1$H-NMR(CDCl$_3$): 2.36(3H, s), 5.20(2H, s), 6.40 (1H, d, J=8 Hz), 6.58(1H, d, J=16 Hz), 6.96(1H, d, J=16 Hz), 7.04(1H, d, J=16 Hz), 7.08(1H, d, J=16 Hz), 7.26–7.54(12H, m), 7.58(1H, d, J=2 Hz), 7.70(1H, d, J=16 Hz). Mass(ESI): m/z 576(M−1). m.p. 230–232° C.

EXAMPLE 36

In the same manner as in Example 1, (E)-3-(1-(1-bromo-2-naphthyl)-4-chloro-2-methylimidazol-5-yl)-N-((4-methylbenzene)-sulfonyl)-2-propenamide (182 mg) was obtained as colorless crystals from (E)-3-(1-(1-bromo-2-naphthyl)-4-chloro-2-methylimidazol-5-yl)-2-propenic acid (175 mg) and (430 methylbenzene)sulfonamide (111 mg).

$^1$H-NMR(CDCl$_3$): 2.30(3H, s), 2.38(3H, s), 5.33(2H, s), 6.42(1H, d, J=8 Hz), 6.52(1H, d, J=15 Hz), 7.23–7.26(2H, m), 7.37(1H, d, J=15 Hz), 7.57(1H, t, J=8 Hz), 7.65(1H, d, J=8 Hz), 7.70(1H, d, J=8 Hz), 7.80(1H, d, J=8 Hz), 7.88(2H, d, J=8 Hz), 8.31(1H, d, J=8 Hz), 8.69(1H, br s). Mass(ESI): m/z 558(M−H)−. m.p. 260–262° C.

EXAMPLE 37

In the same manner as in Example 1, (E)-3-(1-(1-bromo-2-naphthyl)-4-chloro-2-methylimidazol-5-yl)-N-(((E)-2-phenylethenyl)sulfonyl)- 2-propenamide (188 mg) was obtained as colorless crystals from (E)-3-(1-(1-bromo-2-naphthyl)-4-chloro-2-methylimidazol-5-yl)-2-propenic acid (175 mg) and (E)-(2-phenylethene)sulfonamide (119 mg).

$^1$H-NMR(DMSO-d$_6$): 2.33(3H, s), 5.59(2H, s), 6.56(1H, d, J=8 Hz) 6.70(1H, d, J=15 Hz), 7.27(1H, d, J=15 Hz), 7.37–7.48(4H, m), 7.53(1H, d, J=15 Hz), 7.64(1H, t, J=8 Hz), 7.69–7.75(3H, m), 7.94(2H, t, J=8 Hz), 8.26(1H, d, J=8 Hz). Mass(ESI): m/z 570(M−H)−. m.p. 264–265° C.

EXAMPLE 38

In the same manner as in Example 1, (E)-3-(4-chloro-1-(2-chloro-4-(1-pentyloxy)benzyl)-2-methylimidazol-5-yl)-N-(1-pentanesulfonyl)-2-propenamide (135 mg) was obtained as colorless crystals from (E)-3-(4-chloro-1-(2-chloro-4-(1-pentyloxy)benzyl)-2-methylimidazol-5-yl)-2-propenic acid (150 mg) and 1-pentanesulfonamide (86 mg). m.p. 175–176° C.

$^1$H-NMR(CDCl$_3$): 0.89(3H, t, J=6 Hz), 0.93(3H, t, J=6 Hz), 1.25–1.48(8H), 1.70–1.88(4H), 2.36(3H, s), 3.45(2H, t, J=6 Hz), 3.92(2H, t, J=6 Hz), 5.15(2H, s), 6.35(1H, d, J=8 Hz), 6.52(1H, d, J=16 Hz), 6.71(dd, J=8, 2 Hz), 6.99(1H, d, J=2 Hz), 7.44(1H, d, J=16 Hz), 8.03(1H, br. s). MS(ESI): m/z 529(M−1).

EXAMPLE 39

(E)-3-(4-Chloro-1-(2-chloro-4-(1-pentyloxy)benzyl)-2-methylimidazol-5-yl)-2-propenic acid (150 mg) was dissolved in N,N-dimethylformamide (1.5 ml) and carbonyldiimidazole was added. The mixture was stirred at room temperature for 3 hr. To the reaction mixture was added (E)-1-penten-1-ylsulfonamide sodium salt (97 mg), and the mixture was stirred at room temperature for 3 hr and left standing for one day. The reaction mixture was diluted with water (1.5 ml) and adjusted to pH 4 with 1N hydrochloric acid under ice-cooling. The precipitated powder was collected by filtration and washed with water. The resulting white powder was suspended in ethanol (0.75 ml) and heated. The mixture was stirred at room temperature for 30 min. The precipitate was collected by filtration, washed with ethanol and dissolved in N,N-dimethylformamide (0.75 ml) at 80° C. Water (0.25 ml) was added at the same temperature and the mixture was stirred at room temperature for 1 hr. The precipitated crystals were collected by filtration, washed with N,N-dimethylformamide—water (1:1) and then with water to give (E)-3-(4-chloro-1-(2-chloro-4-(1-pentyloxy) benzyl)-2-methylimidazol-5-yl)-N-((E)-1-penten-1-ylsulfonyl)-2-propenamide (160 mg) as colorless crystals.

$^1$H-NMR(CDCl$_3$): 0.92(3H, t, J=6 Hz), 0.94(3H, t, J=6 Hz), 1.30–1.60(6H), 1.78(2H, m), 2.25(2H, q, J=6 Hz), 2.35(3H, s), 3.92(2H, t, J=6 Hz), 5.15(2H, s), 6.33(1H, d, J=8 Hz), 6.49(1H, d, J=16 Hz), 6.54(1H, d, J=16 Hz), 6.70(dd, J=8, 2 Hz), 6.99(1H, d, J=2 Hz), 7.04(1H, dt, J=16, 6 Hz), 7.41(1H, d, J=16 Hz), 8.00(1H, br. s). MS(ESI): m/z 528(M−1).

EXAMPLE 40

In the same manner as in Example 1, (E)-N-(1-butanesulfonyl)-3-(4-chloro-1-(2-chloro-4-(1-pentyloxy)benzyl)-2-methylimidazol-5-yl)-2-propenamide (132 mg) was obtained as colorless crystals from (E)-3-(4-chloro-1-(2-chloro-4-(1-pentyloxy)benzyl)-2-methylimidazol-5-yl)-2-propenic acid (150 mg) and 1-butanesulfonamide (78 mg). m.p. 182–183° C.

$^1$H-NMR(CDCl$_3$): 0.93(3H, t, J=6 Hz), 0.94(3H, t, J=6 Hz), 1.30–1.53(6H), 1.70–1.87(4H), 2.36(3H, s), 3.45(2H, t, J=6 Hz), 3.92(2H, t, J=6 Hz), 5.15(2H, s), 6.35(1H, d, J=8 Hz), 6.54(1H, d, J=16 Hz), 6.71(1H, dd, J=8, 2 Hz), 6.99 (1H, d, J=2 Hz), 7.44(1H, d, J=16 Hz), 8.17(1H, br. s). MS(ESI): m/z 515(M−1).

EXAMPLE 41

In the same manner as in Example 1, (E)-3-(4-chloro-1-(2-chloro-4-((E)-2-phenylethenyl)benzyl)-2-methylimidazol-5-yl)-N-(1-pentanesulfonyl)-2-propenamide was obtained as colorless crystals (116 mg) from (E)-3-(4-chloro-1-(2-chloro-4-((E)-2-phenylethenyl)benzyl)-2-methylimidazol-5-yl)-2-propenic acid (140 mg) and 1-pentanesulfonamide (77 mg).

$^1$H-NMR(CDCl$_3$): 0.87(3H, t, J=7 Hz), 1.24–1.45(4H, m), 1.75–1.88(2H, m), 2.38(3H, s), 3.39–3.46(2H, m), 5.22 (2H, s), 6.42(1H, d, J=8 Hz), 6.54(1H, d, J=16 Hz), 7.00(1H, d, J=16 Hz), 7.12(1H, d, J=16 Hz), 7.27–7.54(7H, m), 7.60(1H, d, J=1 Hz). MS(ESI): m/z 544(M−1). m.p. 215–216° C.

EXAMPLE 42

In the same manner as in Example 1, (E)-3-(4-chloro-1-(2-chloro- 4-((E)-2-phenylethenyl)benzyl)-2-methylimidazol-5-yl)-N-((E)-1-penten-1-ylsulfonyl)-2-propenamide was obtained as colorless crystals (117 mg) from (E)-3-(4-chloro-1-(2-chloro-4-((E)-(2-phenylethenyl))benzyl)-2-methylimidazol-5-yl)-(E)-2-propenic acid (150 mg) and (E)-1-penten-1-ylsulfonamide (81 mg).

$^1$H-NMR(CDCl$_3$): 0.92(3H, t, J=7 Hz), 1.43–1.57(2H, m), 2.14–2.30(2H, m), 2.37(3H, s), 5.21(2H, s), 6.40(1H, d, J=8 Hz), 6.48(1H, d, J=16 Hz), 6.57(1H, d, J=16 Hz), 6.95–7.15(3H, m), 7.26–7.55(7H, m), 7.60(1H, d, J=1 Hz). MS(ESI): m/z 542(M−1). m.p. 226–228° C.

EXAMPLE 43

In the same manner as in Example 1, (E)-N-(1-butane-sulfonyl)-3-(4-chloro-1-(2-chloro-4-((E)-2-phenylethenyl)benzyl)-2-methylimidazol-5-yl)-2-propenamide (148 mg) was obtained as colorless crystals from (E)-3-(4-chloro-1-(2-chloro-4-((E)-2-phenylethenyl)benzyl)-2-methylimidazol-5-yl)-2-propenic acid (150 mg) and 1-butanesulfonamide (75 mg). m.p. 213–214° C.

$^1$H-NMR(CDCl$_3$): 0.92(3H, t, J=6 Hz), 1.44(2H, m), 1.80(2H, m), 2.48(3H, s), 3.44(2H, t, J=6 Hz), 5.22(2H, s), 6.42(1H, d, J=8 Hz), 6.59(1H, d, J=16 Hz), 7.00(1H, d, J=16 Hz), 7.11(1H, d, J=16 Hz), 7.25–7.55(7H), 7.60(1H, d, J=2 Hz), 8.40(1H, br. s). MS(ESI): m/z 531(M−1).

EXAMPLE 44

In the same manner as in Example 1, (E)-3-(4-chloro-1-(2-chloro-4-(phenylethynyl)benzyl-2-methylimidazol-5-yl)-N-(1-pentanesulfonyl)-2-propenamide was obtained as colorless crystals (100 mg) from (E)-3-(4-chloro-1-(2-chloro-4-(phenylethynyl)-benzyl)-2-methylimidazol-5-yl)-2-propenic acid (135 mg) and 1-pentanesulfonamide (74 mg).

$^1$H-NMR(CDCl$_3$): 0.89(3H, t, J=7 Hz), 1.25–1.47(4H, m), 1.75–1.90(2H, m), 2.38(3H, s), 3.40–3.47(2H, m), 5.23 (2H, s), 6.42(1H, d, J=8 Hz), 6.55(1H, d, J=16 Hz), 7.31–7.40(3H, m), 7.42(1H, d, J=16 Hz), 7.48–7.55(2H, m), 7.63(1H, d, J=1 Hz), 7.87(1H, s). MS(ESI): m/z 542(M−1). m.p. 207–209° C.

EXAMPLE 45

In the same manner as in Example 1, (E)-3-(4-chloro-1-(2-chloro-4-(phenylethynyl)benzyl)-2-methylimidazol-5-yl)-N-((E)-1-penten-1-ylsulfonyl)-2-propenamide was obtained as colorless crystals (84 mg) from (E)-3-(4-chloro-1-(2-chloro-4-(phenylethynyl)benzyl)-2-methylimidazol-5-yl)-2-propenic acid (125 mg) and (E)-1-penten-1-ylsulfonamide (68 mg).

$^1$H-NMR(CDCl$_3$) 0.93(3H, t, J=7 Hz), 1.45–1.57(2H, m), 2.20–2.30(2H, m), 2.36(3H, s), 5.22(2H, s), 6.40(1H, d, J=8 Hz), 6.48(1H, d, J=16 Hz), 6.57(1H, d, J=16 Hz), 6.98–7.10 (1H, m), 7.30–7.43(4H, m), 7.48–7.55(2H, m), 7.63(1H, d, J=1 Hz), 7.87(1H, s). MS(ESI): m/z 540(M−1). m.p. 207–210° C.

EXAMPLE 46

In the same manner as in Example 1, (E)-N-(1-butane-sulfonyl)-3-(4-chloro-1-(2-chloro-4-(2-phenylethynyl)benzyl)-2-methylimidazol-5-yl)-2-propenamide (79 mg) was obtained as colorless crystals from (E)-3-(4-chloro-1-(2-chloro-4-(2-phenylethynyl)benzyl)-2-methylimidazol-5-yl)-2-propenic acid (87 mg) and 1-butanesulfonamide (44 mg). m.p. 217–218° C.

$^1$H-NMR(CDCl$_3$): 0.94(3H, t, J=6 Hz), 1.45(2H, m), 1.80(2H, m), 2.47(3H, s), 3.44(2H, t, J=6 Hz), 5.23(2H, s), 6.42(1H, d, J=8 Hz), 6.56(1H, d, J=16 Hz), 7.30–7.55(7H), 7.62(1H, d, J=2 Hz), 8.14(1H, br. s). MS(ESI): m/z 529(M−1).

EXAMPLE 47

In the same manner as in Example 1, (E)-3-(4-chloro-1-((3-chloro-5-(trifluoromethyl)pyridin-2-yl)methyl)-2-methylimidazol-5-yl)-N-((E)-2-phenylethenylsulfonyl)-2-propenamide was obtained as pale-yellow crystals (60 mg) from (E)-3-(4-chloro-1-((3-chloro-5-(trifluoromethyl)pyridin-2-yl)methyl)-2-methylimidazol-5-yl)-2-propenic acid (120 mg) and (E)-(2-phenylethene)sulfonamide (87 mg).

$^1$H-NMR(DMSO-d$_6$): 2.26(3H, s), 5.65(2H, s), 6.66(1H, d, J=16 Hz), 7.27(1H, d, J=16 Hz), 7.38–7.48(4H, m), 7.57(1H, d, J=16 Hz), 7.70–7.78(2H, m), 8.56(1H, d, J=1 Hz), 8.85(1H, s). MS(ESI): m/z 545(M+1). m.p. 249–252° C.

EXAMPLE 48

In the same manner as in Example 1, (E)-3-(4-chloro-1-((3-chloro-5-(trifluoromethyl)pyridin-2-yl)methyl)-2-methylimidazol-5-yl)-N-((4-methylbenzene)sulfonyl)-2-propenamide was obtained as pale-yellow crystals (38 mg) from (E)-3-(4-chloro-1-((3-chloro-5-(trifluoromethyl)pyridin-2-yl)methyl)-2-methylimidazol-5-yl)-2-propenic acid (100 mg) and (4-methylbenzene)sulfonamide (68 mg).

$^1$H-NMR(CDCl$_3$): 2.34(3H, s), 2.42(3H, s), 5.33(2H, s), 5.62(1H, d, J=16 Hz), 7.26–7.36(3H, m), 7.94(2H, d, J=8 Hz), 8.60(2H, s). MS(ESI): m/z 533(M+1). m.p. 239–241° C.

EXAMPLE 49

In the same manner as in Example 1, (E)-3-(1-(4-(tert-butoxycarbonylamino)-2-chlorobenzyl)-4-chloro-2-methylimidazol-5-yl)-N-(1-pentanesulfonyl)-2-propenamide was obtained as colorless crystals (64 mg) from (E)-3-(1-(4-(tert-butoxycarbonylamino)-2-chlorobenzyl)-4-chloro-2-methylimidazol-5-yl)-2-propenic acid (150 mg) and 1-pentanesulfonamide (80 mg).

$^1$H-NMR(CDCl$_3$): 0.89(3H, t, J=7 Hz), 1.28–1.46(4H, m), 1.51(9H, s), 1.75–1.89(2H, m), 2.36(3H, s), 3.40–3.48 (2H, m), 5.16(2H, s), 6.35(1H, d, J=8 Hz), 6.50(1H, d, J=16 Hz), 6.55(1H, s), 7.03(1H, dd, J=1, 8 Hz), 7.43(1H, d, J=16 Hz). MS(ESI): m/z 557(M−1). m.p. 202–204° C.

EXAMPLE 50

In the same manner as in Example 1, (E)-3-(1-(4-(tert-butoxycarbonylamino)-2-chlorobenzyl)-4-chloro-2-methylimidazol-5-yl)-N-((E)-1-penten-1-ylsulfonyl)-2-propenamide was obtained as colorless crystals (59 mg) from (E)-3-(1-(4-(tert-butoxycarbonylamino)-2-chlorobenzyl)-4-chloro-2-methylimidazol-5-yl)-2-propenic acid (130 mg) and (E)-1-penten-1-ylsulfonamide (68 mg).

$^1$H-NMR(DMSO-d$_6$): 0.84(3H, t, J=7 Hz), 1.35–1.49(2H, m), 1.46(9H, s), 2.15–2.25(2H, m), 2.31(3H, s), 5.30(2H, s), 6.47(1H, d, J=8 Hz), 6.65(1H, d, J=16 Hz), 6.67(1H, d, J=16 Hz), 6.75–6.86(1H, m), 7.24(1H, d, J=16 Hz), 7.29(1H, dd, J=1, 8 Hz), 7.71(1H, s). MS(ESI): m/z 555(M−1). m.p. 209–210° C.

EXAMPLE 51

In the same manner as in Example 1, (E)-3-(1-(4-(tert-butoxycarbonylamino)-2-chlorobenzyl)-4-chloro-2-methylimidazol-5-yl)-N-(((E)-2-phenylethenyl)sulfonyl)-2-propenamide was obtained as a pale-yellow powder (81 mg) from (E)-3-(1-(4-(tert-butoxycarbonylamino)-2-chlorobenzyl)-4-chloro-2-methylimidazol-5-yl)-2-propenic acid (200 mg) and (E)-(2-phenylethene)sulfonamide (129 mg).

$^1$H-NMR(DMSO-d$_6$): 1.46(9H, s), 2.29(3H, s), 5.29(2H, s), 6.46(1H, d, J=8 Hz), 6.68(1H, d, J=16 Hz), 7.20–7.30

(2H, m), 7.39–7.50(4H, m), 7.58(1H, d, J=16 Hz), 7.67–7.80 (2H, m). MS(ESI): m/z 589(M−1).

EXAMPLE 52

In the same manner as in Example 1, (E)-3-(4-chloro-1-(2-chloro-4-(n-pentyloxy)benzyl)-2-ethylimidazol-5-yl)-N-((E)-2-phenylethenesulfonyl)-2-propenamide was obtained as colorless crystals (139 mg) from (E)-3-(4-chloro-1-(2-chloro-4-(1-pentyloxy)benzyl)-2-ethylimidazol-5-yl)-2-propenic acid (160 mg) and (E)-2-phenylethenesulfonamide (107 mg). m.p. 174–175° C.

$^1$H-NMR(CDCl$_3$): 0.92(3H, t, J=7 Hz), 1.26(3H, t, J=7 Hz), 1.31–1.48(4H, m), 1.69–1.82(2H, m), 2.61(2H, q, J=7 Hz), 3.90(2H, q, J=7 Hz), 5.14(2H, s), 6.30(1H, d, J=8 Hz), 6.56(1H, d, J=15 Hz), 6.67(1H, dd, J=8, 2 Hz), 6.97(1H, d, J=2 Hz), 7.06(1H, d, J=15 Hz), 7.36–7.55(6H, m), 7.72(1H, d, J=15 Hz).

EXAMPLE 53

In the same manner as in Example 1, (E)-3-(1-(4-bromo-2-chlorobenzyl)-4-chloro-2-ethylimidazol-5-yl)-N-((E)-2-phenylethenesulfonyl)-2-propenamide was obtained as colorless crystals (175 mg) from (E)-3-(1-(4-bromo-2-chlorobenzyl)-4-chloro-2-ethylimidazol-5-yl)-2-propenic acid (200 mg) and (E)-2-phenylethenesulfonamide (136 mg). m.p. 209–210° C.

$^1$H-NMR(CDCl$_3$): 1.27(3H, t, J=7 Hz), 2.59(2H, q, J=7 Hz), 5.14(2H, s), 6.28(1H, d, J=8 Hz), 6.62(1H, d, J=15 Hz), 7.05(1H, d, J=15 Hz), 7.24–7.55(6H, m), 7.60(1H, d, J=1 Hz), 7.72(1H, d, J=15 Hz), 8.34(1H, s). Mass(ESI): m/z 568(M−1).

EXAMPLE 54

In the same manner as in Example 1, (E)-3-(4-chloro-1-(2-chloro-4-(phenylethynyl)benzyl)-2-ethylimidazol-5-yl)-N-((E)-2-phenylethenesulfonyl)-2-propenamide was obtained as pale-yellow crystals (120 mg) from (E)-3-(4-chloro-1-(2-chloro-4-(phenylethynyl)benzyl)-2-ethylimidazol-5-yl)-2-propenic acid (170 mg) and (E)-2-phenylethenesulfonamide (109 mg). m.p. 233–234° C.

$^1$H-NMR(CDCl$_3$): 1.27(3H, t, J=7 Hz), 2.61(2H, q, J=7 Hz), 5.21(2H, s), 6.38(1H, d, J=8 Hz), 6.60(1H, d, J=15 Hz), 7.05(1H, d, J=15 Hz), 7.30(1H, dd, J=8, 1 Hz), 7.43–7.55 (11H, m), 7.59(1H, d, J=1 Hz), 7.71(1H, d, J=15 Hz). Mass(ESI): m/z 588(M−1).

EXAMPLE 55

In the same manner as in Example 1, (E)-3-(4-chloro-1-(2-chloro-4-(phenylethynyl)benzyl)-2-ethylimidazol-5-yl)-N-((4-methylbenzene)sulfonyl)-2-propenamide was obtained as colorless crystals (161 mg) from (E)-3-(4-chloro-1-(2-chloro-4-(phenylethynyl)benzyl)-2-ethylimidazol-5-yl)-2-propenic acid (170 mg) and 4-(methylbenzene) sulfonamide (103 mg). m.p. 250–252° C.

$^1$H-NMR(CDCl$_3$): 1.26(3H, t, J=7 Hz), 2.58(2H, q, J=7 Hz), 5.17(2H, s), 6.33(1H, d, J=8 Hz), 6.56(1H, d, J=15 Hz), 7.25–7.40(7H, m), 7.48–7.55(2H, m), 7.58(1H, d, J=1 Hz), 7.92(1H, d, J=8 Hz), 8.41(1H, br s) Mass(ESI): m/z 576 (M−1).

EXAMPLE 56

In the same manner as in Example 1, (E)-N-(1-butanesulfonyl)-3-(4-chloro-1-(2-chloro-4-(phenylethynyl)benzyl)-2-ethylimidazol-5-yl)-2-propenamide was obtained as colorless crystals (107 mg) from (E)-3-(4-chloro-1-(2-chloro-4-(phenylethynyl)benzyl)-2-ethylimidazol-5-yl)-2-propenic acid (130 mg) and 1-butanesulfonamide (63 mg).

$^1$H-NMR(CDCl$_3$): 0.93(3H, t, J=7 Hz), 1.29(3H, t, J=7 Hz), 1.38–1.53(2H, m), 1.75–1.86(2H, m), 2.63(2H, d, J=7 Hz), 3.40–3.49(2H, m), 5.24(2H, s), 6.41(1H, d, J=8 Hz), 6.56(1H, d, J=16 Hz), 7.30–7.40(4H, m), 7.43(1H, d, J=16 Hz), 7.47–7.55(2H, m), 7.63(1H, d, J=1 Hz). MS(ESI): m/z 542(M−1). m.p. 165–167° C.

EXAMPLE 57

In the same manner as in Example 1, (E)-3-(4-chloro-1-(2-chloro-4-(phenylethynyl)benzyl)-2-ethylimidazol-5-yl)-N-(1-pentanesulfonyl)-2-propenamide was obtained as colorless crystals (93 mg) from (E)-3-(4-chloro-1-(2-chloro-4-(phenylethynyl)benzyl)-2-ethylimidazol-5-yl)-2-propenic acid (130 mg) and 1-pentanesulfonamide (69 mg).

$^1$H-NMR(CDCl$_3$): 0.88(3H, t, J=7 Hz), 1.29(3H, t, J=7 Hz), 1.24–1.46(4H, m), 1.75–1.88(2H, m), 2.63(2H, d, J=7 Hz), 3.38–3.47(2H, m), 5.24(2H, s), 6.40(1H, d, J=8 Hz), 6.56(1H, d, J=16 Hz), 7.30– 7.40(4H, m), 7.43(1H, d, J=16 Hz), 7.48–7.55(2H, m), 7.62(1H, d, J=1 Hz). MS(ESI): m/z 556(M−1). m.p. 161–163° C.

EXAMPLE 58

In the same manner as in Example 39, (E)-3-(4-chloro-1-(2-chloro-4-(phenylethynyl)benzyl)-2-ethylimidazol-5-yl)-N-((E)-1-penten-1-ylsulfonyl)-2-propenamide was obtained as colorless crystals (106 mg) from (E)-3-(4-chloro-1-(2-chloro-4-(phenylethynyl)benzyl)-2-ethylimidazol-5-yl)-2-propenic acid (130 mg) and (E)-1-penten-1-ylsulfonamide sodium salt (78 mg).

$^1$H-NMR(CDCl$_3$): 0.93(3H, t, J=7 Hz), 1.28(3H, t, J=7 Hz), 1.45–1.55(2H, m), 2.19–2.30(2H, m), 2.62(2H, d, J=7 Hz), 5.22(2H, s), 6.40(1H, d, J=8 Hz), 6.48(1H, d, J=16 Hz), 6.58(1H, d, J=16 Hz), 6.98–7.10(1H, m), 7.29–7.45(5H, m), 7.47–7.56(2H, m), 7.62(1H, d, J=1 Hz). MS(ESI): m/z 554(M−1). m.p. 173–175° C.

EXAMPLE 59

In the same manner as in Example 1, (E)-3-(4-chloro-1-(2-chloro-4-((E)-2-phenylethenyl)benzyl)-2-ethylimidazol-5-yl)-N-((E)-2-phenylethenesulfonyl)-2-propenamide was obtained as colorless crystals (180 mg) from (E)-3-(4-chloro-1-(2-chloro-4-((E)-2-phenylethenyl)benzyl)-2-ethylimidazol-5-yl)-2-propenic acid (170 mg) and (E)-2-phenylethenesulfonamide (109 mg). m.p. 218–220° C.

$^1$H-NMR(CDCl$_3$-CD$_3$OD): 1.25(3H, t, J=7 Hz), 2.62(2H, q, J=7 Hz), 5.22(2H, s), 6.38(1H, d, J=8 Hz), 6.90(1H, d, J=15 Hz), 6.98(1H, d, J=15 Hz), 7.04–7.14(2H, m), 7.24–7.44(7H, m), 7.46–7.53(4H, m), 7.58(1H, d, J=1 Hz), 7.68(1H, d, J=15 Hz). Mass(ESI): m/z 425(M−1).

EXAMPLE 60

In the same manner as in Example 1, (E)-3-(4-chloro-1-(2-chloro-4-((E)-2-phenylethenyl)benzyl)-2-ethylimidazol-5-yl)-N-(4-methylbenzenesulfonyl)-2-propenamide was obtained as colorless crystals (153 mg) from (E)-3-(4- chloro-1-(2-chloro-4-((E)-2-phenylethenyl)benzyl)-2-ethylimidazol-5-yl)-2-propenic acid (170 mg) and 4-(methylbenzene)sulfonamide (102 mg). m.p. 250–252° C.
$^1$H-NMR(CDCl$_3$): 1.24(3H, t, J=7 Hz), 2.60(2H, q, J=7 Hz), 5.16(2H, s), 6.34(1H, d, J=8 Hz), 6.54(1H, d, J=15 Hz), 6.96(1H, d, J=15 Hz), 7.19(1H, d, J=15 Hz), 7.21–7.41(7H, m), 7.50(2H, d, J=8 Hz), 7.56(1H, s), 7.92(2H, d, J=8 Hz), 8.47(1H, br s). Mass(ESI): m/z 580(M−1).

EXAMPLE 61

In the same manner as in Example 1, (E)-N-(1-butanesulfonyl)-3-(4-chloro-1-(2-chloro-4-((E)-2-phenylethenyl)benzyl)-2-ethylimidazol-5-yl)-2-propenamide was obtained as colorless crystals (146 mg) from (E)-3-(4-chloro-1-(2-chloro-4-((E)-2-phenylethenyl)benzyl)-2-ethylimidazol-5-yl)-2-propenic acid (150 mg) and 1-butanesulfonamide (72 mg).
$^1$H-NMR(CDCl$_3$): 0.92(3H, t, J=7 Hz), 1.30(3H, t, J=7 Hz), 1.35–1.55(2H, m), 1.74–1.85(2H, m), 2.65(2H, d, J=7 Hz), 3.39–3.48(2H, m), 5.23(2H, s), 6.41(1H, d, J=8 Hz), 6.55(1H, d, J=16 Hz), 6.99(1H, d, J=16 Hz), 7.11(1H, d, J=16 Hz), 7.27–7.62(8H, m). MS(ESI): m/z 544(M−1). m.p. 210–213° C.

EXAMPLE 62

In the same manner as in Example 1, (E)-3-(4-chloro-1-(2-chloro-4-((E)-2-phenylethenyl)benzyl)-2-ethylimidazol-5-yl)-N-(1-pentanesulfonyl)-2-propenamide was obtained as colorless crystals (138 mg) from (E)-3-(4-chloro-1-(2-chloro-4-((E)-2-phenylethenyl)benzyl)-2-ethylimidazol-5-yl)-2-propenic acid (150 mg) and 1-pentanesulfonamide (80 mg).
$^1$H-NMR(CDCl$_3$): 0.87(3H, t, J=7 Hz), 1.23–1.45(4H, m), 1.30(3H, t, J=7 Hz), 1.75–1.88(2H, m), 2.65(2H, d, J=7 Hz), 3.38–3.46(2H, m), 5.23(2H, s), 6.40(1H, d, J=8 Hz), 6.55(1H, d, J=16 Hz), 6.98(1H, d, J=16 Hz), 7.11(1H, d, J=16 Hz), 7.26–7.66(8H, m). MS(ESI): m/z 558(M−1). m.p. 197–200° C.

EXAMPLE 63

In the same manner as in Example 1, (E)-3-(4-chloro-1-(2-chloro-4-((E)-2-phenylethenyl)benzyl)-2-ethylimidazol-5-yl)-N-((E)-1-penten-1-ylsulfonyl)-2-propenamide was obtained as colorless crystals (109 mg) from (E)-3-(4-chloro-1-(2-chloro-4-((E)-2-phenylethenyl)benzyl)-2-ethylimidazol-5-yl)-2-propenic acid (150 mg) and (E)-1-penten-1-ylsulfonamide (79 mg).
$^1$H-NMR(CDCl$_3$): 0.92(3H, t, J=7 Hz), 1.29(3H, t, J=7 Hz), 1.43–1.56(2H, m), 2.18–2.28(2H, m), 2.63(2H, d, J=7 Hz), 5.21(2H, s), 6.40(1H, d, J=8 Hz), 6.48(1H, d, J=16 Hz), 6.57(1H, d, J=16 Hz), 6.95–7.15(3H, m), 7.25–7.61(8H, m). MS(ESI): m/z 556(M−1). m.p. 197–200° C.

EXAMPLE 64

In the same manner as in Example 1, (E)-3-(1-(4-bromo-2-chlorobenzyl)-2,4-dimethylimidazol-5-yl)-N-((E)-2-phenylethenesulfonyl)-2-propenamide (150 mg) was obtained as a colorless powder from (E)-3-(1-(4-bromo-2-chlorobenzyl)-2,4-dimethylimidazol-5-yl)-2-propenic acid (140 mg) and (E)-2-phenylethenesulfonamide (104 mg).
$^1$H-NMR(CDCl$_3$-CD$_3$OD): 2.29(3H, s), 2.40(3H, s), 5.12(2H, s), 6.04(1H, d, J=15 Hz), 6.23(1H, d, J=8 Hz), 7.08(1H, d, J=15 Hz), 7.28(1H, dd, J=8, 2 Hz), 7.45–7.53(6H, m), 7.61(1H, d, J=2 Hz), 7.67(1H, d, J=16 Hz) Mass(ESI): m/z 534(M−H)$^-$ m.p. 251–253° C.

EXAMPLE 65

In the same manner as in Example 1, (E)-3-(4-bromo-1-(2-chloro-4-(1-pentyloxy)benzyl)-2-methylimidazol-5-yl)-N-((E)-2-phenylethenesulfonyl)-2-propenamide (218 mg) was obtained as colorless crystals from (E)-3-(4-bromo-1-(2-chloro-4-(1-pentyloxy)benzyl)-2-methylimidazol-5-yl)-2-propenic acid (200 mg) and (E)-2-phenylethenesulfonamide (124 mg).
$^1$H-NMR(CDCl$_3$): 0.92(3H, t, J=7 Hz), 1.32–1.47(4H, m), 1.72–1.81(2H, m), 2.35(3H, s), 3.90(2H, t, J=7 Hz), 5.14(2H, s), 6.32(1H, d, J=8 Hz), 6.63(1H, d, J=15 Hz), 6.68(1H, dd, J=8, 2 Hz), 6.97(1H, d, J=2 Hz), 7.06(1H, d, J=15 Hz), 7.42–7.45(4H, m), 7.50–7.53(2H, m), 7.72(1H, d, J=15 Hz) Mass(ESI): m/z 606(M−H)$^-$ m.p. 208–209° C.

EXAMPLE 66

In the same manner as in Example 1, (E)-3-(1-(2-chloro-4-(1-pentyloxy)benzyl)-4-ethyl-2-methylimidazol-5-yl)-N-((E)-2-phenylethenesulfonyl)-2-propenamide (102 mg) was obtained as a colorless powder from (E)-3-(1-(2-chloro-4-(1-pentyloxy)benzyl)-4-ethyl-2-methylimidazol-5-yl)-2-propenic acid (150 mg) and (E)-2-phenylethenesulfonamide (105 mg).
$^1$H-NMR(CDCl$_3$): 0.92(3H, t, J=7 Hz), 1.26(3H, t, J=7 Hz), 1.32–1.45(4H, m), 1.70–1.80(2H, m), 2.33(3H, s), 2.72(2H, q, J=7 Hz), 3.89(2H, t, J=7 Hz), 5.11(2H, s), 5.84(1H, d, J=15 Hz), 6.30(1H, d, J=8 Hz), 6.67(1H, dd, J=8, 2 Hz), 6.96(1H, d, J=2 Hz), 7.06(1H, d, J=15 Hz), 7.36–7.44(3H, m), 7.46–7.59(3H, m), 7.68(1H, d, J=15 Hz) Mass(ESI): m/z 554(M−H)$^-$

EXAMPLE 67

In the same manner as in Example 1, (E)-2-benzyl-3-(1-(2-chloro-4-(1-pentyloxy)benzyl)-2-methylimidazol-5-yl)-N-((E)-2-phenylethenesulfonyl)-2-propenamide (138 mg) was obtained as colorless crystals from (E)-2-benzyl-3-(1-(2-chloro-4-(1-pentyloxy)benzyl)-2-methylimidazol-5-yl)-2-propenic acid (200 mg) and (E)-2-phenylethenesulfonamide (121 mg).
$^1$H-NMR(CDCl$_3$): 0.93(3H, t, J=7 Hz), 1.32–1.47(4H, m), 1.72–1.82(2H, m), 2.35(3H, s), 3.90(2H, t, J=7 Hz), 3.96(2H, s), 5.15(2H, s), 6.30(1H, d, J=8 Hz), 6.67(1H, dd, J=8, 2 Hz), 6.92–6.98(2H, m), 7.12(2H, d, J=8 Hz), 7.20–7.32(5H, m), 7.35–7.45(5H, m), 7.58(1H, d, J=8 Hz) Mass(ESI): m/z 616(M−H)$^-$ m.p. 171–172° C.

EXAMPLE 68

In the same manner as in Example 1, (E)-3-(1-(2-chloro-4-(1-pentyloxy)benzyl)-2-methylimidazol-5-yl)-2-(1-pentyl)-N-((E)-2-phenylethenesulfonyl)-2-propenamide (123 mg) was obtained as colorless crystals from (E)-3-(1-(2-chloro-4-(1-pentyloxy)benzyl)-2-methylimidazol-5-yl)-2-(1-pentyl)-2-propenic acid (200 mg) and (E)-2-phenylethenesulfonamide (127 mg).
$^1$H-NMR(CDCl$_3$): 0.88(3H, t, J=7 Hz), 0.92(3H, t, J=7 Hz), 1.25–1.55(10H, m), 1.70–1.80(2H, m), 2.37(3H, s), 2.48(2H, t, J=7 Hz), 3.89(2H, t, J=7 Hz), 5.12(2H, s), 6.32(1H, d, J=8 Hz), 6.67(1H, dd, J=8, 2 Hz), 6.95–6.97(2H, m), 7.12(1H, d, J=15 Hz), 7.27(1H, d, J=9 Hz), 7.37–7.47

(3H, m), 7.50–7.53(2H, m), 7.72(1H, d, J=15 Hz) Mass (ESI): m/z 596(M−H)⁻ m.p. 168–169° C.

EXAMPLE 69

In the same manner as in Example 1, (E)-3-(1-(2-chloro-4-(1-pentyloxy)benzyl)-2-methylimidazol-5-yl)-2-((3-pyridyl)methyl)-N-((E)-2-phenylethenesulfonyl)-2-propenamide (139 mg) was obtained as colorless crystals from (E)-3-(1-(2-chloro-4-(1-pentyloxy)benzyl)-2-methylimidazol-5-yl)-2-(3-pyridyl)methyl-2-propenic acid (230 mg) and (E)-2-phenylethenesulfonamide (139 mg).

$^1$H-NMR(CDCl$_3$): 0.94(3H, t, J=7 Hz), 1.32–1.48(4H, m), 1.72–1.82(2H, m), 2.38(3H, s), 3.86(2H, t, J=7 Hz), 3.97(2H, s), 5.00(2H, s), 6.37(1H, d, J=8 Hz), 6.61(1H, d, J=8, 2 Hz), 6.92(1H, d, J=2 Hz), 6.95(1H, s), 6.98(1H, d, J=15 Hz), 7.18–7.27(2H, m), 7.32–7.45(5H, m), 7.56–7.63 (2H, m), 8.09(1H, s), 8.48(1H, d, J=5 Hz) Mass(ESI): m/z 617(M−H)⁻ m.p. 156–158° C.

EXAMPLE 70

In the same manner as in Example 1, (E)-3-(1-(2-chloro-4-(1-pentyloxy)benzyl)-2-methylimidazol-5-yl)-2-methyl-N-((E)-2-phenylethenesulfonyl)-2-propenamide (183 mg) was obtained as colorless crystals from (E)-3-(1-(2-chloro-4-(1-pentyloxy)benzyl)-2-methylimidazol-5-yl)-2-methyl-2-propenic acid (200 mg) and (E)-2-phenylethenesulfonamide (146 mg).

$^1$H-NMR(CDCl$_3$): 0.92(3H, t, J=7 Hz), 1.30–1.47(4H, m), 1.71–1.80(2H, m), 2.12(3H, s), 2.36(3H, s), 3.89(2H, t, J=7 Hz), 5.13(2H, s), 6.29(1H, d, J=8 Hz), 6.66(1H, dd, J=8, 2 Hz), 7.08–7.15(2H, m), 7.33(1H, s), 7.36–7.47(3H, m), 7.49–7.53(2H, m), 7.70(1H, d, J=15 Hz) Mass(ESI): m/z 540(M−H)⁻ m.p. 143–145° C.

EXAMPLE 71

In the same manner as in Example 1, (E)-3-(4-chloro-1-(2-chloro-4-(1-pentyloxy)benzyl)-2-methylimidazol-5-yl)-2-methyl-N-((E)-2-phenylethenesulfonyl)-2-propenamide (90 mg) was obtained as colorless crystals from (E)-3-(4-chloro-1-(2-chloro-4-(1-pentyloxy)benzyl)-2-methylimidazol-5-yl)-2-methyl-2-propenic acid (120 mg) and (E)-2-phenylethenesulfonamide (80 mg).

$^1$H-NMR(CDCl$_3$): 0.93(3H, t, J=7 Hz), 1.32–1.48(4H, m), 1.72–1.82(2H, m), 1.99(3H, s), 2.31(3H, s), 3.91(2H, t, J=7 Hz), 5.00(2H, s), 6.40(1H, d, J=2 Hz), 6.70(1H, dd, J=8, 2 Hz), 6.92–6.94(2H, m), 7.11(1H, d, J=15 Hz), 7.38–7.45 (3H, m), 7.52–7.55(2H, m), 7.73(1H, d, J=15 Hz), 8.32(1H, br s) Mass(ESI): m/z 574(M−H)⁻ m.p. 156–157° C.

EXAMPLE 72

In the same manner as in Example 1,4-chloro-1-(2-chloro-4-(1-pentyloxy)benzyl)-2-methyl-5-((E)-2-phenylethenesulfonyl-carbamoyl)-1H-imidazole (108 mg) was obtained as colorless crystals from 4-chloro-1-(2-chloro-4-(1-pentyloxy)benzyl)-2-methyl-1H-imidazole-5-carboxylic acid (200 mg) and (E)-2-phenylethenesulfonamide (148 mg).

$^1$H-NMR(CDCl$_3$): 0.91(3H, t, J=7 Hz), 1.28–1.37(4H, m), 1.60–1.70(2H, m), 2.02(3H, s), 3.62(2H, t, J=7 Hz), 5.32(2H, s), 6.32(1H, d, J=8 Hz), 6.44(1H, d, J=8 Hz), 6.58–6.64(2H, m), 7.05–7.20(6H, m) Mass(ESI): m/z 534 (M−H)⁻ m.p. 107–110° C.

EXAMPLE 73

4-Chloro-1-(2-chloro-4-(1-pentyloxy)benzyl)-5-hydroxymethyl-2-methyl-1H-imidazole (150 mg) was dissolved in 1,4-dioxane (1.5 ml) and p-toluenesulfonyl isocyanate (99 mg) was added at room temperature. The reaction mixture was stirred at room temperature for 1 hr and concentrated under reduced pressure. To the residue was added ethanol (5 ml) and the precipitated crystals were collected by filtration. The crystals were dissolved in ethyl acetate (2 ml), and hexane (13 ml) was added on an oil bath at 70° C. The mixture was allowed to cool and the precipitated crystals were collected by filtration. The crystals were dried by heating under reduced pressure to give (4-chloro-1-(2-chloro-4-(1-pentyloxy)benzyl)-2-methyl-1H-imidazol-5-yl)methyl N-(4-methylbenzenesulfonyl)carbamate (176 mg) as colorless crystals.

$^1$H-NMR(CDCl$_3$): 0.93(3H, t, J=7 Hz), 1.32–1.50(4H, m), 1.73–1.83(2H, m), 2.29(3H, s), 2.45(3H, s), 3.93(2H, t, J=7 Hz), 4.93(2H, s), 5.02(2H, s), 6.31(1H, d, J=8 Hz), 6.68(1H, dd, J=8, 2 Hz), 6.94(1H, d, J=2 Hz), 7.32(2H, d, J=8 Hz), 7.95(2H, d, J=8 Hz) Mass(ESI): m/z 552(M−H)⁻ m.p. 109–111° C.

EXAMPLE 74

In the same manner as in Example 73, 4-chloro-1-(2-chloro-4-(1-pentyloxy)benzyl)-5-((3-(4-methylbenzenesulfonyl)-ureidomethyl)-2-methyl-1H-imidazole (41 mg) was obtained as colorless crystals from 5-aminomethyl-4-chloro-1-(2-chloro-4-(1-pentyloxy)benzyl)-2-methyl-1H-imidazole (70 mg) and p-toluenesulfonyl isocyanate (43 mg).

$^1$H-NMR(CDCl$_3$): 0.92(3H, t, J=7 Hz), 1.30–1.47(4H, m), 1.70–1.80(2H, m), 2.34(3H, s), 2.43(3H, s), 3.90(2H, t, J=7 Hz), 4.24(2H, d, J=7 Hz), 5.06(2H, s), 6.25(1H, d, J=8 Hz), 6.65–6.68(2H, m), 6.93(1H, d, J=2 Hz), 7.28(2H, d, J=8 Hz), 7.68(2H, d, J=8 Hz) Mass(ESI): m/z 551(M−H)⁻ m.p. 165–166° C.

EXAMPLE 75

In the same manner as in Example 73, 4-chloro-1-(2-chloro-4-(1-pentyloxy)benzyl)-5-((3-(4-methylbenzenesulfonyl)-1-methylureido)methyl)-2-methyl-1H-imidazole (60 mg) was obtained as a colorless powder from 5-(N-methylamino)methyl-4-chloro-1-(2-chloro-4-(1-pentyloxy) benzyl)-2-methyl-1H-imidazole (70 mg) and p-toluenesulfonyl isocyanate (41 mg).

$^1$H-NMR(CDCl$_3$): 0.93(3H, t, J=7 Hz), 1.30–1.48(4H, m), 1.72–1.82(2H, m), 2.09(3H, s), 2.38(3H, s), 2.72(3H, s), 3.88(2H, t, J=7 Hz), 4.41(2H, s), 4.99(2H, s), 6.15(1H, d, J=8 Hz), 6.61(1H, dd, J=8, 2 Hz), 6.82(1H, d, J=2 Hz), 7.13(2H, d, J=8 Hz), 7.70(2H, d, J=8 Hz) Mass(ESI): m/z 565(M−H)⁻

EXAMPLE 76

(E)-3-(4-Chloro-1-(2-chloro-4-(phenylethenyl)benzyl)-2-ethylimidazol-5-yl)-N-((E)-1-penten-1-yl)sulfonyl-2-propenamide (853 mg) was suspended in ethanol (7 ml), and 1N aqueous sodium hydroxide solution (1.53 ml) was added. The solvent was evaporated under reduced pressure. To the residue was added ethyl acetate (17 ml), and the mixture was heated and filtrated while it was hot. The filtrate was allowed to cool and the precipitated powder was collected by filtration and dried by heating under reduced pressure to give (E)-3-(4-chloro-1-(2-chloro-4-(phenylethynyl)benzyl)-2-ethylimidazol-5-yl)-N-((E)-1-penten-1-yl)sulfonyl)-2-propenamide sodium salt (737 mg) as a colorless powder.

IR (KBr): 2958, 2227, 2202, 1635, 1552, 1498, 1460, 1383, 1335, 1296, 1263, 1238, 1101, 1066, 1049, 966, 866, 839 cm$^{-1}$ $^1$H-NMR(DESO-d$_6$): 0.85(3H, t, J=7 Hz), 1.13(3H, t, J=7 Hz), 1.30–1.43(2H, m), 2.02(2H, q, J=7 Hz), 2.57(2H, q, J=7 Hz), 5.34(2H, s), 6.20–6.30(2H, m), 6.47(1H, d, J=7 Hz), 6.55(1H, d, J=15 Hz), 6.93(1H, d, J=15 Hz), 7.41–7.45(3H, m), 7.48(1H, dd, J=8, 2 Hz), 7.54–7.58(2H, m), 7.78(1H, d, J=2 Hz) Mass(ESI): m/z 554(M−H)$^-$

INDUSTRIAL APPLICABILITY

The above-mentioned imidazole compounds and pharmaceutically acceptable salts thereof of the present invention are useful as pharmaceutical preparations which, based on the hypoglycemic action, are used for the prophylaxis and treatment of, for example, impaired glucose tolerance disorder, diabetes (e.g., type II diabetes), gestational diabetes, diabetic complications (e.g., diabetic gangrene, diabetic arthropathy, diabetic osteopenia, diabetic glomerulosclerosis, diabetic nephropathy, diabetic dermatopathy, diabetic neuropathy, diabetic cataract, diabetic retinopathy and the like), insulin resistance syndrome (e.g., insulin receptor abnormality, Rabson-Mendenhall syndrome, leprechaunism, Kobberling-Dunnigan syndrome, Seip syndrome, Lawrence syndrome, Cushing syndrome, acromegaly and the like), polycystic ovary syndrome, hyperlipidemia, atherosclerosis, cardiovascular diseases (e.g., stenocardia, cardiac failure and the like), hyperglycemia (e.g., those characterized by abnormal saccharometabolism such as eating disorders), pancreatitis, osteoporosis, hyperuricemia, hypertension, inflammatory bowel diseases, and skin disorders related to an anomaly of differentiation of epidermic cells; and which, based on the cGMP-PDE (particularly PDE-V) inhibitory action, smooth muscle relaxing action, bronchodilating action, vasodilating action, smooth muscle cell inhibitory action, allergy suppressing action and the like, are used for angina pectoris, hypertension, pulmonary hypertension, congestive heart failure, glomerulopathy (e.g., diabetic glomerulosclerosis), tubulointerstitial disorders (e.g., kidney diseases induced by FK506, cyclosporine and the like), renal failure, atherosclerosis, angiostenosis (e.g., after percutaneous arterioplasty), peripheral vascular diseases, cerebral apoplexy, chronic reversible obstructive impairment (e.g., bronchitis, asthma inclusive of chronic asthma and allergic asthma), autoimmune diseases, allergic rhinitis, urticaria, glaucoma, diseases characterized by impaired intestinal motility (e.g., irritable bowel syndrome), impotence (e.g., organic impotence, psychic impotence and the like), nephritis, cancer cachexia or restenosis after PTCA, cachexia (e.g., progressive weight loss due to lipolysis, myolysis, anemia, edema, anorexia and the like in chronic diseases such as cancer, tuberculosis, endocrine diseases and AIDS, and the like. A combination of a compound of formula (I) or pharmaceutically acceptable salts thereof and a retinoid is useful for treating disease states caused by uncontrolled cell proliferation, including cancer, restenosis and atherosclerosis.

This application is based on application Nos. 10-367362 and 11-228838 filed in Japan on Dec. 24, 1998 and Aug. 12, 1999, respectively, the contents of which are incorporated hereinto by reference.

What is claimed is:
1. An imidazole compound of the formula:

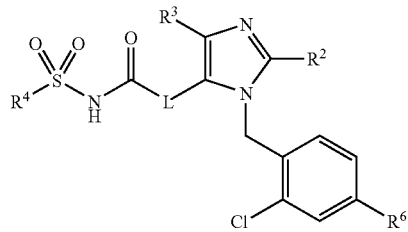

wherein
R$^2$ is a lower alkyl;
R$^3$ is chlorine;
R$^4$ is (1) a lower alkenyl optionally substituted by aryl or heterocyclic group, (2) aryl optionally substituted by lower alkenyl, (3) lower alkyl, or (4) heterocyclic group optionally substituted by halogen;
R$^6$ is lower alkenyl optionally substituted by phenyl, or lower alkynyl optionally substituted by phenyl; and
L is ethylene,
where aryl is defined as unsubstituted aryl or alkyl-substituted aryl, or a salt thereof.
2. The imidazole compound of claim 1 which is:
(5) (E)-3-(4-chloro-1-(2-chloro-4-(phenylethynyl)benzyl)-2-methylimidazol-5-yl)-N-((4-methylbenzene)sulfonyl)-2-propenamide,
(6) (2E)-3-(4-chloro-1-(2-4-(phenylethynyl)benzyl)-2-methylimidazol-5-yl)-N-(((E)-2-phenylethenyl)sulfonyl)-2-propenamide,
(34) (E)-3-(4-chloro-1-(2-chloro-4-((E)-2-phenylethenyl)benzyl)-2-methylimidazol-5-yl)-N-((4-methylbenzene)sulfonyl)-2-propenamide,
(35)(E)-3-(4-chloro-1'-(2-chloro-4-((E)-2-phenylethenyl)benzyl)-2-methylimidazol-5-yl)-N-(((E)-2-phenylethenyl)sulfonyl)-2-propenamide,
(41) (E)-3-(4-chloro-1-(2-chloro-4-((E)-2-phenylethenyl)benzyl)-2-methylimidazol-5-yl)-N-(1-pentanesulfonyl)-2-propenamide,
(42) (E)-3-(4-chloro-1-(2-chloro-4-((E)-2-phenylethenyl)benzyl)-2-methylimidazol-5-yl)-N-((E)-1-penten-1-ylsulfonyl)-2-propenamide,
(43) (E)-N-(1-butanesulfonyl)-3-(4-chloro-1-(2-chloro-4-((E)-2-phenylethenyl)benzyl)-2-methylimidazol-5-yl)-2-propenamide,
(44) (E)-3-(4-chloro-1-(2-chloro-4-(phenylethynyl)benzyl)-2-methylimidazol-5-yl)-N-(1-pentanesulfonyl)-2-propenamide,
(45) (E)-3-(4-chloro-1-(2-chloro-4-(phenylethynyl)benzyl)-2-methylimidazol-5-yl)-N-((E)-1-penten-1-ylsulfonyl)-2-propenamide,
(46) (E)-N-(1-butanesulfonyl)-3-(4-chloro-1-(2-chloro-4-(2-phenylethynyl)benzyl)-2-methylimidazol-5-yl)-2-propenamide,
(54) (E)-3-(4-chloro-1-(2-chloro-4-(phenylethynyl)benzyl)-2-ethylimidazol-5-yl)-N-((E)-2-phenylethenesulfonyl)-2-propenamide,
(55) (E)-3-(4-chloro-1-(2-chloro-4-phenylethynyl)benzyl)-2-ethylimidazol-5-yl)-N-((4-methylbenzene)sulfonyl)-2-propenamide,
(56) (E)-N-(1-butanesulfonyl)-3-(4-chloro-1-(2-chloro-4-(phenylethynyl)benzyl)-2-ethylimidazol-5-yl)-2-propenamide,

(57) (E)-3-(4-chloro-1-(2-chloro-4-(phenylethynyl)benzyl)-2-ethylimidazol-5-yl)-N-(1-pentanesulfonyl)-2-propenamide,

(58) (E)-3-(4-chloro-1-(2-chloro-4-(phenylethynyl)benzyl)-2-ethylimidazol-5-yl)-N-((E)-1-penten-1-ylsulfonyl)-2-propenamide,

(59) (E)-3-(4-chloro-1-(2-chloro-4-((E)-2-phenylethenyl)benzyl)-2-ethylimidazol-5-yl)-N-((E)-2-phenylethenesulfonyl)-2-propenamide,

(60) (E)-3-(4-chloro-1-(2-chloro-4-((E)-2-phenylethenyl)benzyl)-2-ethylimidazol-5-yl)-N-(4-methylbenzenesulfonyl)-2-propenamide,

(61) (E)-N-(1-butanesulfonyl)-3-(4-chloro-1-(2-chloro-4-((E)-2-phenylethenyl)benzyl)-2-ethylimidazol-5-yl)-2-propenamide,

(62) (E)-3-(4-chloro-1-(2-chloro-4-((E)-2-phenylethenyl)benzyl)-2-ethylimidazol-5-yl)-N-(1-pentanesulfonyl)-2-propenamide, or

(63) (E)-3-(4-chloro-1-(2-chloro-4-((E)-2-phenylethenyl)benzyl)-2-ethylimidazol-5-yl)-N-((E)-1-penten-1-ylsulfonyl)-2-propenamide, or a salt thereof.

3. The imidazole compound of claim 1, which is:

(E)-3-(4-chloro-1-(2-chloro-4-(phenylethynyl)benzyl)-2-methylimidazol-5-yl)-N-((4-methylbenzene)sulfonyl)-2-propenamide, (E)-3-(4-chloro-1-(2-chloro-4-(phenylethynyl)benzyl)-2-ethylimidazol-5-yl)-N-((4-methylbenzene)sulfonyl)-2-propenamide, (E)-3-(4-chloro-1-(2-chloro-4-(phenylethynyl)benzyl)-2-ethylimidazol-5-yl)-N-(1-pentanesulfonyl)-2-propenamide or (E)-3-(4-chloro-1-(2-chloro-4-(phenylethynyl)benzyl)-2-ethylimidazol-5-yl)-N-((E)-1-penten-1-ylsulfonyl)-2-propenamide, or a salt thereof.

4. A pharmaceutical composition containing the imidazole compound of claim 2, or a pharmaceutically acceptable salt thereof, in admixture with a pharmaceutically acceptable organic or inorganic excipient.

5. A pharmaceutical preparation containing the imidazole compound of claim 2, or a pharmaceutically acceptable salt thereof, in admixture with a pharmaceutically acceptable organic or inorganic excipient, which is used as an agent for the treatment of diabetes, polycystic ovary syndrome, atherosclerosis, hyperglycemia, or hypertension.

6. A method of treating a disease in a patient treatable with a pharmaceutical compound having hypoglycemic activity selected from the group consisting of diabetes, polycystic ovary syndrome, atherosclerosis, hyperglycemia, osteoporosis, and hypertension, which comprises administering to the patient the hypoglycemically active imidazole compound of claim 2 or a pharmaceutically acceptable salt thereof.

* * * * *

UNITED STATES PATENT AND TRADEMARK OFFICE
CERTIFICATE OF CORRECTION

PATENT NO. : 7,060,721 B1  Page 1 of 1
APPLICATION NO. : 09/869135
DATED : June 13, 2006
INVENTOR(S) : Oku et al.

It is certified that error appears in the above-identified patent and that said Letters Patent is hereby corrected as shown below:

On the title page, Item (73), the Assignee information is incorrect. Item (73) should read:

-- (73) Assignee:  Astellas Pharma Inc., Tokyo (JP) --

Signed and Sealed this

Sixth Day of January, 2009

JON W. DUDAS
*Director of the United States Patent and Trademark Office*